US010301681B2

(12) United States Patent
Skog et al.

(10) Patent No.: US 10,301,681 B2
(45) Date of Patent: May 28, 2019

(54) METHODS OF TREATING A SUBJECT WITH A HIGH GLEASON SCORE PROSTATE CANCER

(71) Applicant: Exosome Diagnostics, Inc., Cambridge, MA (US)

(72) Inventors: Johan Karl Olov Skog, Charlestown, MA (US); Mikkel Noerholm, Gauting (DE)

(73) Assignee: Exosome Diagnostics, Inc., Waltham, MA (US)

( * ) Notice: Subject to any disclaimer, the term of this patent is extended or adjusted under 35 U.S.C. 154(b) by 472 days.

(21) Appl. No.: 14/909,916

(22) PCT Filed: Aug. 6, 2014

(86) PCT No.: PCT/US2014/049946
§ 371 (c)(1),
(2) Date: Feb. 3, 2016

(87) PCT Pub. No.: WO2015/021158
PCT Pub. Date: Feb. 12, 2015

(65) Prior Publication Data
US 2016/0177401 A1    Jun. 23, 2016

Related U.S. Application Data

(60) Provisional application No. 61/862,630, filed on Aug. 6, 2013.

(51) Int. Cl.
*C12Q 1/6886* (2018.01)
*G01N 33/48* (2006.01)

(52) U.S. Cl.
CPC ...... *C12Q 1/6886* (2013.01); *C12Q 2600/112* (2013.01); *C12Q 2600/118* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 5,219,727 A | 6/1993 | Wang et al. |
| 5,538,871 A | 7/1996 | Nuovo et al. |
| 5,556,773 A | 9/1996 | Yourno |
| 5,582,981 A | 12/1996 | Toole et al. |
| 5,639,606 A | 6/1997 | Willey |
| 5,840,867 A | 11/1998 | Toole et al. |
| 6,004,755 A | 12/1999 | Wang |
| 6,525,154 B1 | 2/2003 | Shea et al. |
| 6,812,023 B1 | 11/2004 | Lamparski et al. |
| 6,893,837 B2 | 5/2005 | Slamon et al. |
| 6,899,863 B1 | 5/2005 | Dhellin et al. |
| 6,913,879 B1 | 7/2005 | Schena |
| 6,994,960 B1 | 2/2006 | Foote et al. |
| 7,074,563 B2 | 7/2006 | Köster |
| 7,186,512 B2 | 3/2007 | Martienssen et al. |
| 7,198,893 B1 | 4/2007 | Köster et al. |
| 7,198,923 B1 | 4/2007 | Abrignani et al. |
| 7,332,553 B2 | 2/2008 | Sellergren et al. |
| 7,364,848 B2 | 4/2008 | Van Beuningen et al. |
| 7,378,245 B2 | 5/2008 | Liu |
| 7,384,589 B2 | 6/2008 | Hart et al. |
| 2010/0196426 A1 | 8/2010 | Skog et al. |
| 2010/0298151 A1 | 11/2010 | Taylor et al. |
| 2011/0003704 A1 | 1/2011 | Skog et al. |
| 2011/0053157 A1 | 3/2011 | Skog et al. |

FOREIGN PATENT DOCUMENTS

| RU | 2348042 C1 | 2/2009 | |
| WO | WO 2003/023065 A1 | 3/2003 | |
| WO | WO 2003/050290 A2 | 6/2003 | |
| WO | WO 2006/066965 A2 | 6/2006 | |
| WO | WO 2006/113590 A2 | 10/2006 | |
| WO | WO 2009/100029 A1 | 8/2009 | |
| WO | WO 2011/009104 A1 | 1/2011 | |
| WO | WO 2011/031877 A1 | 3/2011 | |
| WO | WO 2011/031892 A1 | 3/2011 | |
| WO | WO 2013/028788 A1 | 2/2013 | |
| WO | WO-2013028788 A1 * | 2/2013 | ........... C12Q 1/6886 |
| WO | WO 2015/021158 A1 | 2/2015 | |

OTHER PUBLICATIONS

Sood et al. (PDEF in Prostate Cancer, 2012, vol. 72, No. 6. pp. 592-596: Pub. Date: Jul. 27, 2011). (Year: 2011).*
Abravaya, et al., "Detection of point mutations with a modified ligase chain reaction (Gap-LCR)." Nucleic Acids Research (1995); 23(4): 675-682.
Al-Nedawi, et al., "Intercellular transfer of the oncogenic receptor EGFRvIII by microvesicles derived from tumour cells." Nat Cell Biol. (2008); 10(5): 619-624.
Balzar, et al., "The biology of the 17-1A antigen (Ep-CAM)." J Mol Med. (1999); 77(10): 699-712.
Bossi et al., "Molecularly imprinted polymers for the recognition of proteins: The state of the art." Biosensors and Bioelectronics (2007); 22(6): 1131-1137.
Bussemakers, et al., "DD3::A New Prostate-specific Gene, Highly Overexpressed in Prostate Cancer." Cancer Research (1999) 59(23): 5975-5979.
Cadieux, et al., "Genome-wide Hypomethylation in Human Glioblastomas Associated with Specific Copy Number Alteration, Methylenetetrahydrofolate Reductase Allele Status, and Increased Proliferation." Cancer Research (2006); 66(17): 8469-8476.
Chen, et al., "Microfluidic isolation and transcriptome analysis of serum microvesicles." Lab Chip (2010); 10(4): 505-511.
Cheruvanky, et al., "Rapid isolation of urinary exosomal biomarkers using a nanomembrane ultrafiltration concentrator." Am J Physiol Renal Physiol. (2007); 292: F1657-F1661.

(Continued)

*Primary Examiner* — Pablo S Whaley
(74) *Attorney, Agent, or Firm* — Cooley LLP; Ivor R. Elrifi; Matthew Pavao

(57) ABSTRACT

The present invention relates generally to the field of biomarker analysis, particularly determining gene expression signatures from urine samples. The disclosure provides compositions, kits and methods for diagnosing a prostate disorder such as prostate cancer in a male subject.

7 Claims, 20 Drawing Sheets

Specification includes a Sequence Listing.

(56) References Cited

OTHER PUBLICATIONS

Cortez and Calin, "MicroRNA identification in plasma and serum: a new tool to diagnose and monitor diseases." Expert Opinion on Biological Therapy (2009); 9(6): 703-711.
Cotton, et al., "Reactivity of cytosine and thymine in single-base-pair mismatches with hydroxylamine and osmium tetroxide and its application to the study of mutations." Proc Natl Acad Sci U S A (1988); 85 (12): 4397-4401.
Cowell and Lo, "Application of Oligonucleotides Arrays for Coincident Comparative Genomic Hybridization, Ploidy Status and Loss of Heterozygosity Studies in Human Cancers." Methods in Molecular Biology (2009); 556 (5): 47-65.
Decision to Grant in European Patent Application No. 14752743.6 dated Feb. 20, 2018, 95 pages.
Deras, et al., "PCA3: A Molecular Urine Assay for Predicting Prostate Biopsy Outcome." The Journal of Urology (2008); 179(4): 1587-1592.
Diehl, et al. "Circulating mutant DNA to assess tumor dynamics." Nature Medicine (2008); 14: 985-990.
Fischer and Lerman, "[11] Two-dimensional electrophoretic separation of restriction enzyme fragments of DNA." Methods in Enzymology (1979); 68: 183-191.
Fischer and Lerman, "Length-independent separation of DNA restriction fragments in two-dimensional gel electrophoresis." Cell (1979); 16(1): 191-200.
Furusato, et al., "Mapping of TMPRSS2-ERG fusions in the context of multi-focal prostate cancer." Modern Pathology(2008); 21: 67-75.
Ghadersohi, et al., "Prostate-derived Ets transcription factor (PDEF) is a potential prognostic marker in patients with prostate cancer." The Prostate (2011); 71(11): 1178-1188.
Guatelli, et al., "Isothermal, in vitro amplification of nucleic acids by a multienzyme reaction modeled after retroviral replication." Proc Natl Acad Sci U S A (1990); 87: 1874-1878.
Hahn, "Molecular biology of double-minute chromosomes." BioEssays (1993); 15(7): 477-484.
Hessels, et al., "Detection of TMPRSS2-ERG Fusion Transcripts and Prostate Cancer Antigen 3 in Urinary Sediments May Improve Diagnosis of Prostate Cancer." Clinical Cancer Research (2007); 13(17): 5103-5108.
International Preliminary Report on Patentability for International Application No. PCT/US2014/049946, dated Feb. 9, 2016, 7 pages.
International Search Report and Written Opinion for International Application No. PCT/US2014/049946, dated Dec. 5, 2014, 11 pages.
Itadani, et al., "Can Systems Biology Understand Pathway Activation? Gene Expression Signatures as Surrogate Markers for Understanding the Complexity of Pathway Activation." Current Genomics (2008); 9(5): 349-360.
Johnson, et al., "Surface-immobilized peptide aptamers as probe molecules for protein detection." Anal Chem. (2008); 80(4): 978-983.
Kan and Dozy, "Antenatal diagnosis of sickle-cell anaemia by DNA analysis of amniotic-fluid cells." The Lancet (1978); 312(8096): 910-912.
Kan and Dozy, "Polymorphism of DNA sequence adjacent to human β-globin structural gene: relationship to sickle mutation." PNAS (1978); 75(11): 5631-5635,.
Kristensen and Hansen, "PCR-Based Methods for Detecting Single-Locus DNA Methylation Biomarkers in Cancer Diagnostics, Prognostics, and Response to Treatment." Clinical Chemistry (2009); 55(8): 1471-1483.
Kwoh, et al., "Transcription-based amplification system and detection of amplified human immunodeficiency virus type 1 with a bead-based sandwich hybridization format." Proc Natl Acad Sci U S A (1989); 86: 1173-1177.
Landegren, et al., "A ligase-mediated gene detection technique." Science (1988); 241(4869): 1077-1080.

Laxman, et al., "A First-Generation Multiplex Biomarker Analysis of Urine for the Early Detection of Prostate Cancer." Cancer Research (2008); 68(3): 645-649.
Laxman, et al., "Noninvasive Detection of TMPRSS2:ERG Fusion Transcripts in the Urine of Men with Prostate Cancer." Neoplasia (2006); 8(10): 885-888.
Li, et al., "Replacing PCR with COLD-PCR enriches variant DNA sequences and redefines the sensitivity of genetic testing." Nature Medicine (2008); 14(5): 579-584.
Li, et al., "BEAMing up for detection and quantification of rare sequence variants." Nat Methods. (2006); 3(2): 95-97.
Lipson, et al., "Quantification of the yeast transcriptome by single-molecule sequencing." Nature Biotechnology (2009); 27(7): 652-658.
Mattick, et al., "RNA regulation: a new genetics?" Nature Reviews Genetics (2004); 5: 316-323.
McKiernan, et al., "A novel urine exosome gene expression assay to predict high-grade prostate cancer at initial biopsy." JAMA Oncol. (2016); 2(7): 882-889.
Miele, et al., "Autocatalytic replication of a recombinant RNA." J Mol Biol. (1983); 171: 281-295.
Miranda, et al., "Nucleic acids within urinary exosomes/microvesicles are potential biomarkers for renal disease." Kidney International (2010); 78(2): 191-199.
Myers, et al., "Detection of single base substitutions by ribonuclease cleavage at mismatches in RNA:DNA duplexes." Science (1985); 230(4731): 1242-1246.
Nakazawa, et al., "UV and skin cancer: specific p53 gene mutation in normal skin as a biologically relevant exposure measurement." Proc Natl Acad Sci U S A. (1994); 91: 360-364.
Nguyen, et al., "A Panel of TMPRSS2:ERG Fusion Transcript Markers for Urine-Based Prostate Cancer Detection with High Specificity and Sensitivity." European Urology (2011); 59(3): 407-414.
Nilsson, et al., "Prostate cancer-derived urine exosomes: a novel approach to biomarkers for prostate cancer." British Journal of Cancer (2009); 100: 1603-1607.
Novakova, et al., "MicroRNA involvement in glioblastoma pathogenesis." Biochemical and Biophysical Research Communications (2009); 386(1): 1-5.
Orita, et al., "Detection of polymorphisms of human DNA by gel electrophoresis as single-strand conformation polymorphisms." PNAS (1989); 86(8): 2766-2770.
Orozco and Lewis, "Flow cytometric analysis of circulating microparticles in plasma." Cytometry A (2010); 77A(6): 502-514.
Palanisamy, et al., "Rearrangements of the RAF kinase pathway in prostate cancer, gastric cancer and melanoma." Nature Medicine (2010); 16(7): 793-798.
Parsons, et al., "An Integrated Genomic Analysis of Human Glioblastoma Multiforme." Science (2008); 321(5897): 1807-1812.
Petrovics, et al., "Frequent overexpression of ETS-related gene-1 (ERG1) in prostate cancer transcriptome." Oncogene (2005); 24: 3847-3852.
Raposo, et al., "B lymphocytes secrete antigen-presenting vesicles." Journal of Experimental Medicine (1996); 183: 1161-1172.
Rice, et al., "Evaluation of the ETS-Related Gene mRNA in Urine for the Detection of Prostate Cancer." Clinical Cancer Research (2010); 16(5): 1572-1576.
Rostad, et al., "TMPRSS2:ERG fusion transcripts in urine from prostate cancer patients correlate with a less favorable prognosis." APMIS (2009); 117(8): 575-582.
Salami, et al., "Combining urinary detection of TMPRSS2:ERG and PCA3 with serum PSA to predict diagnosis of prostate cancer." Urologic Oncology (2013); 31(5): 566-571.
Skog, et al., "Glioblastoma microvesicles transport RNA and proteins that promote tumour growth and provide diagnostic biomarkers." Nature Cell Biology (2008); 10(12): 1470-1476.
Sood, et al., "PDEF in Prostate Cancer." The Prostate (2012); 72(6): 592-596.
Steemers, et al., "Whole-genome genotyping with the single-base extension assay." Nature Methods (2006); 3: 31-33.
Taylor and Gercel-Taylor, "MicroRNA signatures of tumor-derived exosomes as diagnostic biomarkers of ovarian cancer." Gynecol Oncol. (2008); 110: 13-21.

(56) References Cited

OTHER PUBLICATIONS

Ting, et al., "Aberrant Overexpression of Satellite Repeats in Pancreatic and Other Epithelial Cancers." Science (2011); 331(6017): 593-596.
Tomlins, et al., "Recurrent Fusion of TMPRSS2 and ETS Transcription Factor Genes in Prostate Cancer." Science (2005); 310(5748): 644-648.
Tomlins, et al., "Urine TMPRSS2:ERG Fusion Transcript Stratifies Prostate Cancer Risk in Men with Elevated Serum PSA." Science Translational Medicine (2011); 3(94): 94ra72.
Velculescu, et al., "Serial Analysis of Gene Expression." Science (1995); 270(5235): 484-487.
Went, et al., "Frequent EpCam protein expression in human carcinomas." Hum Pathol. (2004); 35: 122-128.
Wong, et al., "Real-time PCR for mRNA quantitation." Biotechniques (2005); 39(1): 75-85.
Zhang, et al., "Survivin mediates resistance to antiandrogen therapy in prostate cancer." Oncogene (2005); 24: 2474-2482.

\* cited by examiner

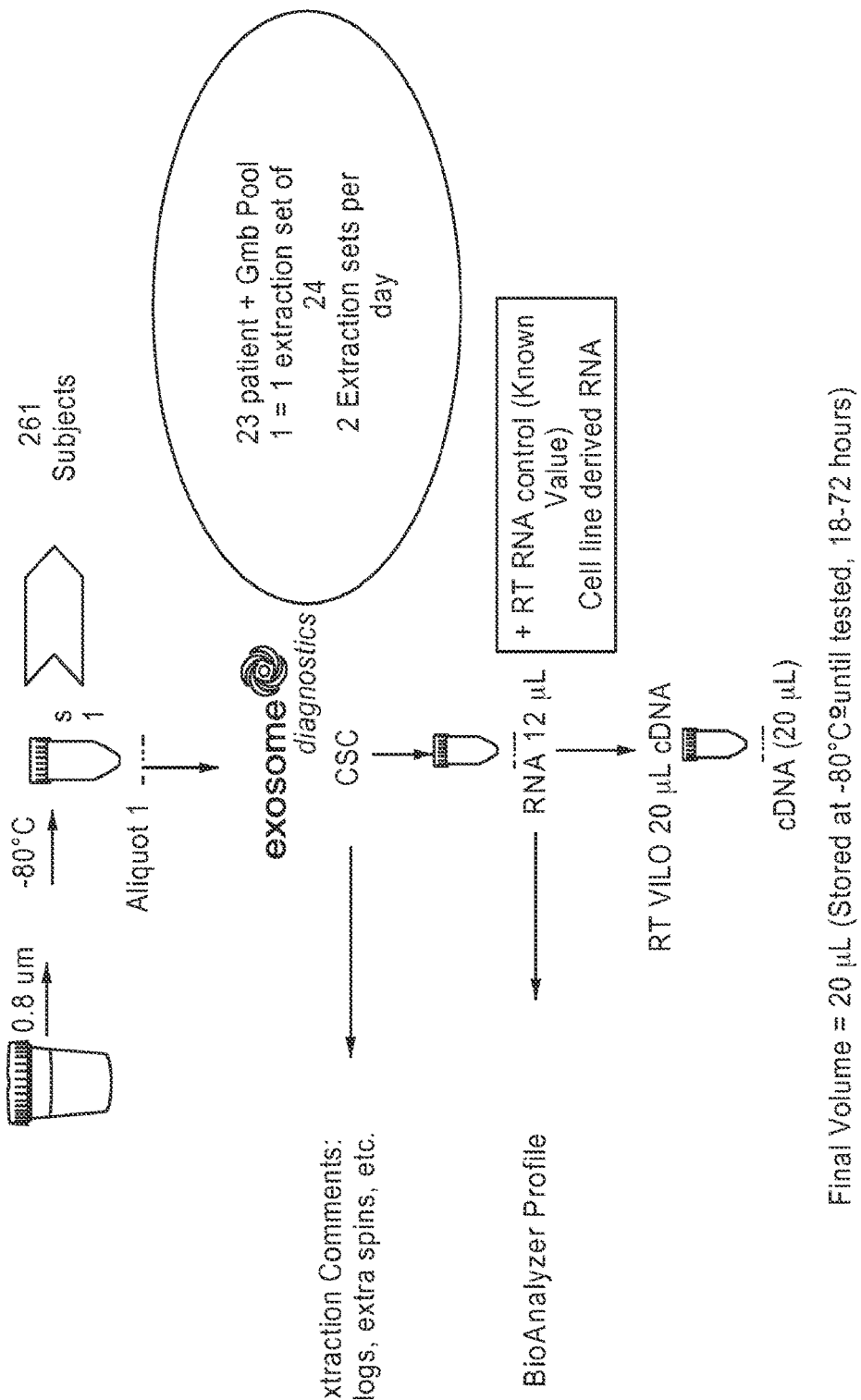

FIGURE 1B
Cohort 7 Workflow Day 2

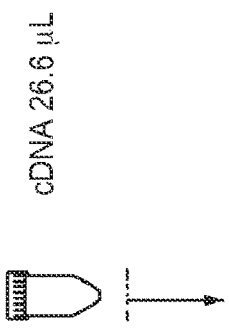

cDNA 26.6 μL

Qbeta.2, KLK3.2,
ERG.2, PCA3.2
2 μL per QPCR

Real Time qPCR

One gene assay per plate 48 samples
RNA RT control, Extraction Control and
cDNA Standard Curve on each Plate. Each
gene assayed on 1 Qiagen RGQ instrument
Standard Curve KLK3, ERG, PCA3 (10e5,
10e4, 10e3, 10e2, 50 down to 10
copies/reaction) in duplicate

Remaining patient
sample cDNA stored
at -80 °C

Additional testing or
genes TBD estimated
remaining reactions = 6

Samples excluded by decreasing Volume cut-off

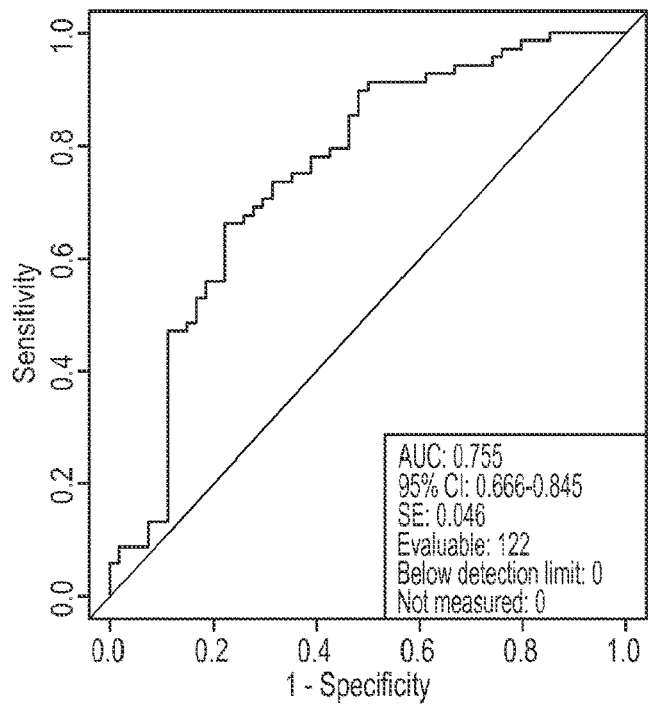

FIGURE 9
ROC ERGandPCA3 <= 20

AUC: 0.755
95% CI: 0.666-0.845
SE: 0.046
Evaluable: 122
Below detection limit: 0
Not measured: 0

FIGURE 10

| | | Model Cutoff | 4.7 | | | |
|---|---|---|---|---|---|---|
| | | | BX POS | BX NEG | | |
| Cohort | c5 | TEST POS | 61 | 31 | 66.3% | PPV |
| Equation | c5 | TEST NEG | 12 | 44 | 78.6% | NPV |
| | | | 83.6% SENS | 58.7% SPEC | | |

| | | Model Cutoff | 4.7 | | | |
|---|---|---|---|---|---|---|
| | | | BX POS | BX NEG | | |
| Cohort | c7; V=20 mL | TEST POS | 47 | 41 | 53.4% | PPV |
| Equation | c5 | TEST NEG | 7 | 27 | 79.4% | NPV |
| | | | 87.0% SENS | 39.7% SPEC | | |

| | | Model Cutoff | 4.7 | | | |
|---|---|---|---|---|---|---|
| | | | BX POS | BX NEG | | |
| Cohort | c7; V ≤40mL | TEST POS | 66 | 77 | 46.2% | PPV |
| Equation | c5 | TEST NEG | 12 | 34 | 73.9% | NPV |
| | | | 84.6% SENS | 30.6% SPEC | | |

| | | Model Cutoff | 4.7 | | | |
|---|---|---|---|---|---|---|
| | | | BX POS | BX NEG | | |
| Cohort | c7; V ≤100m | TEST POS | 79 | 100 | 44.1% | PPV |
| Equation | c5 | TEST NEG | 14 | 43 | 75.4% | NPV |
| | | | 84.9% SENS | 30.1% SPEC | | |

METHODS OF TREATING A SUBJECT WITH A HIGH GLEASON SCORE PROSTATE CANCER

RELATED APPLICATIONS

This application is a national stage application, filed under 35 U.S.C. § 371, of PCT Application No. PCT/US2014/049946, filed Aug. 6, 2014, which claims the benefit of U.S. Provisional Application No. 61/862,630, filed Aug. 6, 2013, the contents of which are incorporated herein by reference in their entirety.

INCORPORATION OF SEQUENCE LISTING

The contents of the text file named "EXOS016N01US_ST25.txt," which was created on Feb. 2, 2016 and is 56.0 KB in size, are hereby incorporated by reference in their entirety.

FIELD OF INVENTION

The present invention relates generally to the field of biomarker analysis, particularly determining gene expression signatures from urine samples.

BACKGROUND

Increasing knowledge of the genetic and epigenetic changes occurring in cancer cells provides an opportunity to detect, characterize, and monitor tumors by analyzing tumor-related nucleic acid sequences and profiles. These changes can be observed by detecting any of a variety of cancer-related biomarkers. Various molecular diagnostic assays are used to detect these biomarkers and produce valuable information for patients, doctors, clinicians and researchers. So far, these assays primarily have been performed on cancer cells derived from surgically removed tumor tissue or from tissue obtained by biopsy.

However, the ability to perform these tests using a bodily fluid sample is oftentimes more desirable than using a patient tissue sample. A less invasive approach using a bodily fluid sample has wide ranging implications in terms of patient welfare, the ability to conduct longitudinal disease monitoring, and the ability to obtain expression profiles even when tissue cells are not easily accessible, e.g., in the prostate gland. For these samples, the collection methods previously disclosed often required a digital rectal exam (DRE) or prostate massage to enable enough prostate-derived cellular fluid to enter the urine. Samples collected without DRE or prostate massage showed a lower detection rate of these biomarkers.

Accordingly, there exists a need for new, noninvasive methods of detecting biomarkers, for example, biomarkers in urinary microvesicles, to aid in diagnosis, prognosis, monitoring, or therapy selection for a disease or other medical condition of the prostate gland. In particular, there exists a need for noninvasive methods that do not require DRE or prostate massage prior to urine sample collection and do not require a sample preparation step involving isolation of a cellular pellet from urine samples.

SUMMARY OF THE INVENTION

The present invention provides methods of detecting one or more biomarkers in urine microvesicles to aid in diagnosis, prognosis, monitoring, or therapy selection for a disease such as, for example, cancer, particularly a disease or other medical condition of the prostate gland in a subject. The method includes obtaining a random urine sample from a subject; extracting mRNA from the sample, detecting the level of mRNA expression of PCA3 and ERG; and normalizing the level of mRNA expression of PCA3 and ERG to KLK3 or SPDEF. The method further comprises computing an output value for the normalized mRNA expression levels of PCA3 and ERG using a predetermined formula; and comparing the output value to a predetermined cutoff value that was determined using an ROC curve generated based on a combination of PCA3 and ERG to distinguish a subject at a high risk for cancer from a subject with a low risk for cancer. Furthermore, these methods allow for the identification of a subject at high risk of a high Gleason score (GS) prostate cancer (e.g., a Gleason score (GS)>6), as compared to a subject at low risk of a high GS prostate cancer. For example, subjects having an output value that is greater than, or in some embodiments, equal to, the predetermined cutoff value that was determined using an ROC curve generated based on a combination of PCA3 and ERG, are at high risk for a high GS prostate cancer, while subjects having an output value that is lower than the predetermined cutoff value are a low risk for a high GS prostate cancer. Thus, these methods are useful for distinguishing between subjects at high risk for a high GS prostate cancer from subjects at a low risk of a high GS prostate cancer.

The invention provides a method for diagnosis, prognosis, monitoring or therapy selection in a subject in need thereof, consisting of the steps of obtaining a random urine sample from the subject; extracting one or more mRNAs from the sample; detecting a level of expression of PCA3 and ERG mRNAs; normalizing the level of expression of PCA3 and ERG mRNAs to a reference gene; computing an output value by applying the normalized expression levels of PCA3 and ERG mRNAs to a predetermined formula; and comparing the output value to a predetermined cutoff value that was determined using an ROC curve generated based on a combination of PCA3 mRNA and ERG mRNA to distinguish a subject with a high risk of recurrence of cancer from a subject with a low risk of recurrence of cancer.

The methods of the disclosure use a urine sample from a male subject, e.g., a sample between 25-40 mL of first catch urine. The methods of the disclosure do not require a digital rectal exam (DRE), and preferably, the urine samples used in these methods are samples from patients who have not been subjected to DRE.

In some embodiments, the PSA level of the patient is detected. In some embodiments, the methods are used to analyze samples from patients in the PSA "gray zone" having a PSA level that is between 2-10 ng/mL. In some embodiments, the patient is a human male subject that is at least 50 years old.

In some embodiments, the patient sample is analyzed using the following algorithm:

$$EXO106\ Score = \left(\log_2 \frac{\max(1,\ ERG\ \text{copies})}{SPDEF\ \text{copies}} + \log_2 \frac{\max(1,\ PCA3\ \text{copies})}{SPDEF\ \text{copies}} + 16.92\right) * 1.83$$

In some embodiments, the EXO106 score is used to predict whether a patient is at a low risk of prostate cancer or a high risk of prostate cancer. For example, patients having an EXO106 score that is less than 10 as calculated using the algorithm above are identified as having a low risk of prostate cancer, and patients having an EXO106 score that is 10 or higher are identified as having a higher risk of prostate cancer.

In some embodiments, the EXO106 score is used to predict whether a patient is at a low risk of a high Gleason score (GS) prostate cancer or a high risk of a high GS prostate cancer. For example, patients having an EXO106 score that is less than 10 as calculated using the algorithm above are identified as having a low risk of a high GS prostate cancer, and patients having an EXO106 score that is 10 or higher are identified as having a higher risk of a high GS prostate cancer.

In some embodiments, the methods of the present invention further include isolating a microvesicle fraction from the random urine sample and extracting the nucleic acids from the microvesicle fraction.

In some embodiments, the method further comprises further includes detecting the level of expression of AMACR, BIRC5, HOXC6, and/or SPARCL1. In some embodiments, the method further comprises further includes detecting the level of expression of AMACR, BIRC5, HOXC6, and/or SPARCL1 and computing the output value based on the combination of PCA3, ERG, and AMACR, BIRC5, HOXC6, and/or SPARCL1.

In any of the foregoing methods, a known quantity of Q-beta particles is added to the urine sample prior to nucleic acid extraction. The expression level of the Q-beta target gene is detected and the detected expression level is compared to the known quantity of Q-beta particles.

The invention provides a method for diagnosis, prognosis, monitoring or therapy selection for a medical condition in a subject, comprising the steps of: (a) obtaining a microvesicle fraction from a urine sample from a subject; (b) extracting one or more nucleic acids from the microvesicle fraction; and (c) analyzing the extracted nucleic acids to detect the presence, absence or level of expression of PCA3 and ERG. These markers are detectable at a stable level in fresh urine samples, as well as urine samples that have been previously frozen and thawed. Preferably, the urine samples are 40 mL or 20 mL. More preferably, the urine samples are the first 40 mL voided from the bladder or the first 20 mL voided from the bladder. Detection of these markers is reproducible across samples from the same patient, as well as across samples from various patients.

The invention also provides a method further comprising the step of detecting a level of expression of a reference gene and determining a normalized, relative expression level of the biomarkers, wherein the relative expression level of the biomarkers is a ratio between the level of biomarker expression to the level of reference gene expression, and wherein the subject is identified as suffering from, or being at an increased risk for, a medical condition, such as cancer, when the relative expression level of the biomarker is greater than a cutoff level of biomarker expression. In some embodiments, the biomarker is at least ERG and PCA3. In some embodiments, the biomarker is at least ERG and PCA3 and at least one other biomarker selected from the group consisting of AMACR, BIRC5, HOXC6, SPARCL1, and combinations thereof. In some embodiments, the reference gene is a prostate-specific gene. In some embodiments, the reference gene is KLK3 or SPDEF, or a combination thereof. In some embodiments, the reference gene is KLK3. In some embodiments, the reference gene is a housekeeping gene, such as, for example GAPDH.

In some embodiments, the Area Under the Curve (AUC) derived from the Receiver Operator Characteristic (ROC) curve for each level of biomarker or a score created by a combination of biomarkers is computed using biomarker results from both controls and patients with disease. In some preferred embodiments, the AUC value derived from the ROC curve for each level of biomarker or a score created by a combination of biomarkers is greater than 0.5, 0.6, 0.7, or 0.8. Preferably, the AUC value is greater than 0.7. One skilled in the art would readily be able to maximize diagnostic accuracy of the biomarker level or combination of biomarkers by implementing a cut-off analysis that takes into account the sensitivity, specificity, negative predictive value (NPV), positive predictive value (PPV), positive likelihood ratio (PLR) and negative likelihood ratio (NLR) necessary for clinical utility. Biomarker results or a combination of biomarker results are analyzed in any of a variety of ways. In some embodiments, the results are analyzed using a univariate, or single-variable analysis (SV). In some embodiments, the results are analyzed using multivariate analysis (MV). Examples of both SV and MV analyses of biomarkers and/or biomarker cohorts are shown in the Tables below.

In some embodiments, the reference gene is a prostate-specific gene. In some embodiments, the reference gene is KLK3 or SPDEF, or a combination thereof. In some embodiments, the reference gene is a housekeeping gene, for example GAPDH.

The biomarkers and combinations of biomarkers (also referred to herein as biomarker cohorts) are useful in methods of diagnosis, prognosis, monitoring or therapy selection for a medical condition such as cancers, including aggressive cancers. In some embodiments, the biomarkers and combinations of biomarkers are useful in correlating biomarker and/or cohort expression with the likelihood that the subject is suffering from or is at risk for suffering from an aggressive cancer based on the level of expression and/or pattern of expression detected. In some embodiments, the biomarkers and combinations of biomarkers are useful in correlating biomarker and/or cohort expression with the likelihood that the subject is suffering from or is at risk for suffering from a recurrence of a cancer based on the level of expression and/or pattern of expression detected. In some embodiments, the biomarkers and combinations of biomarkers are useful in correlating biomarker and/or cohort expression with the likelihood that the subject is suffering from or is at risk for suffering from an aggressive prostate cancer based on the level of expression and/or pattern of expression detected. The biomarkers and combinations of biomarkers are useful in correlating biomarker and/or cohort expression with the Gleason score of a subject. For example, the expression level of a biomarker and/or cohort can be used to identify a subject's Gleason score based on the level of expression and/or pattern of expression detected. For example, the expression level of a PCA3 and ERG can be used to identify that a subject's Gleason score is greater than 6. The biomarkers and combinations of biomarkers are useful in correlating biomarker and/or cohort expression with the likelihood that the subject will need a radical prostatectomy based on the level of expression and/or pattern of expression detected.

In some embodiments, the medical condition is cancer. For example, the cancer is prostate cancer. In some embodiments, the cancer is a urogenital cancer, for example, a prostate cancer, a renal cancer, a bladder cancer, or a metastatic cancer that has spread to urogenital organs. In some embodiments, the cancer is an aggressive cancer. For example, in some embodiments, the medical condition is an aggressive prostate cancer, an aggressive renal cancer, or an aggressive bladder cancer.

The subject in need thereof is suffering from or at risk of suffering from cancer, for example, an aggressive cancer. In some embodiments, the subject is suffering from or is at risk of suffering from prostate cancer. In some embodiments, the subject is not at risk of suffering from prostate cancer. In some embodiments, the subject has prostate cancer and has been assigned a particular Gleason score. For example, in some embodiments, the subject has been assigned a Gleason score that is greater than or equal to 7. In some embodiments, the subject has been assigned a Gleason score that is greater than or equal to 1, 2, 3, 4, 5, 6, 7, 8 or 9. In some embodiments, the subject has been assigned a Gleason score that is in the range of 1 to 10, 1 to 9, 1 to 8, 1 to 7, 1 to 6, 1 to 5, 1 to 4, 1 to 3, 1 to 2, 2 to 10, 2 to 9, 2 to 8, 2 to 7, 2 to 6, 2 to 5, 2 to 4, 2 to 3, 3 to 10, 3 to 9, 3 to 8, 3 to 7, 3 to 6, 3 to 5, 3 to 4, 4 to 10, 4 to 9, 4 to 8, 4 to 7, 4 to 6, 4 to 5, 5 to 10, 5 to 9, 5 to 8, 5 to 7, 5 to 6, 6 to 10, 6 to 9, 6 to 8, 6 to 7, 7 to 10, 7 to 9, 7 to 8, 8 to 10, 8 to 9 or 9 to 10. In some embodiments, the subject has undergone a prostatectomy, for example, a radical prostatectomy or is at risk for having to undergo a prostatectomy, for example, a radical prostatectomy.

The subject is, for example, a male human subject with clinical suspicion for prostate cancer, e.g., based on a PSA test result and/or a suspicious DRE. In some embodiments, the subject has a clinical history of negative biopsy. In some embodiments, the subject does not have a clinical history of negative biopsy. In some embodiments, the subject has been recommended for a repeat biopsy. In some embodiments, the subject has been recommended for an initial, or first-time, biopsy.

In some embodiments, the subject has been recommended or scheduled for prostatectomy. In some embodiments, the subject has histologically confirmed acinar type (i.e., typical) prostate cancer. In some embodiments, the prostate cancer is localized. In some embodiments, the prostate cancer is locally advanced.

In some embodiments, the subject is not suffering from and/or is not suspected of suffering from a disease such as an infectious disease, e.g., hepatitis (all types) and/or HIV. In some embodiments, the subject has no history of concurrent renal and/or bladder tumor. In some embodiments, the subject has not received previously or is not concurrently receiving any form of neoadjuvant or focal therapy for prostate cancer. In some embodiments, the subject has not received previously or is not concurrently receiving any form of neoadjuvant or focal therapy, including androgen derivation therapy, within six months of providing the urine sample.

The markers and/or combinations of markers described herein are useful in a variety of kits, for example, a diagnostic kit which can be used to test urine samples from a variety of patients. In some embodiments, the urine sample is concentrated, e.g., using a filtration concentration step, before testing the sample with the kit. The results can be processed using any of a variety of methods, including apparatuses for fast qPCR readout.

BRIEF DESCRIPTION OF THE DRAWINGS

FIGS. 1A and 1B are a series of schematic illustrations depicting the lab workflow for analysis of the Patient Cohort 7 samples on Day 1 (FIG. 1A) and Day 2 (FIG. 1B).

In FIG. 3A, the Y axis represents AUC values and the X axis represents each sample in Cohort 7. In FIG. 3B, the Y axis shows the sample volume and the X axis represents each sample in Cohort 7. The key designates the clinical sites where each sample is from. FIGS. 3A and 3B demonstrate that PCA3 AUC (normalized to KLK3) improves from <0.65 to >0.7 when donation volumes are restricted to only 20 mL. These figures demonstrate that the AUC was highly dependent on the sample volume.

FIG. 9 is a graph depicting ROC curves based on ERG and PCA3 expression analysis normalized to KLK3 with samples from Patient Cohort 7 in which the sample volume was less than or equal to 20 mL (N=122). ERG expression analysis was imputed. The X axis represents specificity; the Y axis represents sensitivity.

FIG. 10 is a series of four tables showing the 2×2 analysis of the Cohort 7 data using the predetermined formula and model cutoff threshold values that were applied to previous Cohort 5 data. (Sens=sensitivity; Spec=specificity; NPV=negative predictive value; PPV=positive predictive value; C5=Cohort 5; C7=Cohort 7). Weights fitted to data in C5 performed well when applied to C7, despite several changes between C5 and C7 such as, for example, extraction protocol and probe chemistry. The C5 cohort volumes were generally lower than in C6, with more samples of the 40 mL volume.

FIG. 14A shows the comparison of C5 with C7 for all samples. FIG. 14B shows the comparison of C5 with C7 low volume samples. FTO=3 gene model that does not use PCA3. FTO refers to 3 gene models that do not use PCA3.

DETAILED DESCRIPTION

Figure 2A:
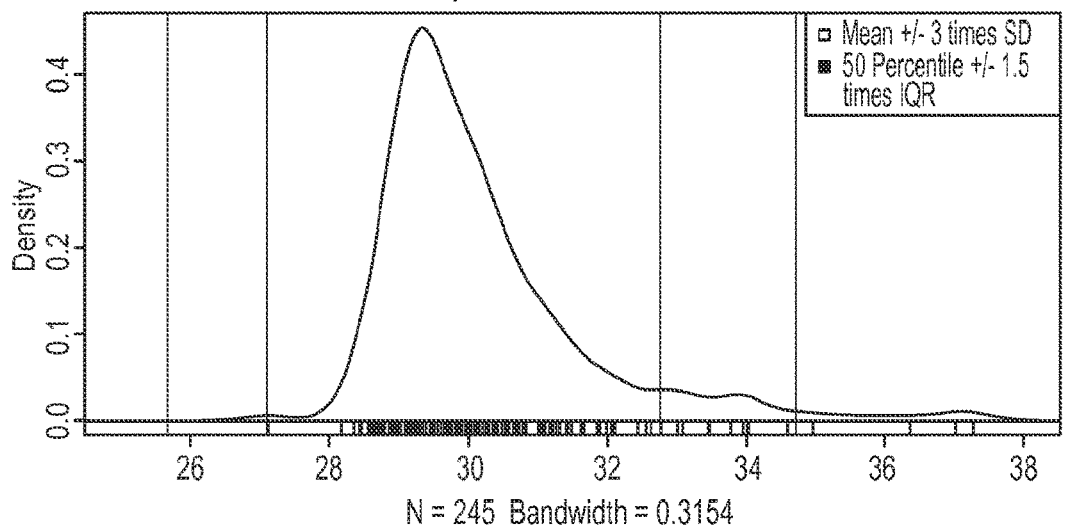
FIG. 2A is a graph depicting the density distribution of Qbeta Ct values detected for 258 Cohort 7 samples. The Y axis represents the density and the X axis represents the Ct value.
Figure 2B:
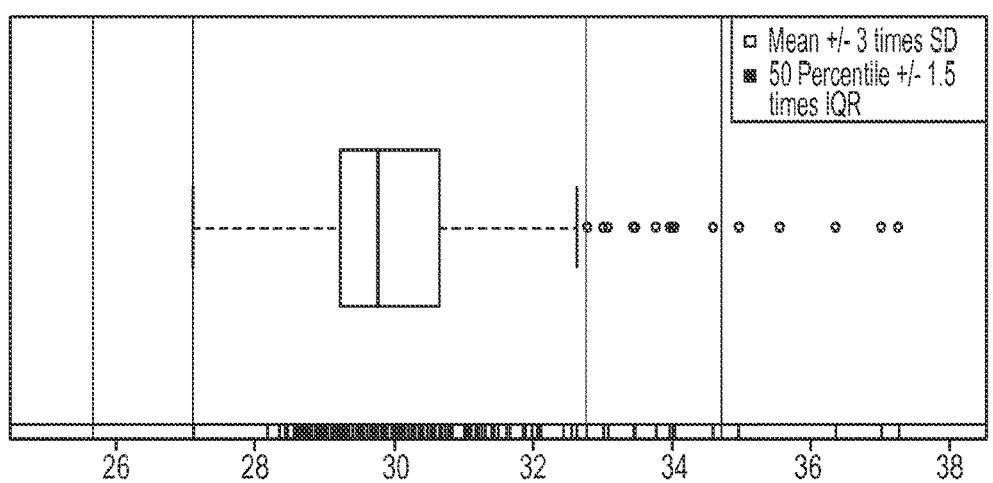
FIG. 2B is a box plot depicting the density distribution of Qbeta Ct values detected for the 258 Cohort 7 samples. The X axis represents the Ct value.

Cancer-related biomarkers include, e.g., specific mutations in gene sequences (Cortez and Calin, 2009; Diehl et al., 2008; Network, 2008; Parsons et al., 2008), up- and down-regulation of mRNA and miRNA expression (Cortez and Calin, 2009; Itadani et al., 2008; Novakova et al., 2009), mRNA splicing variations, changes in DNA methylation patterns (Cadieux et al., 2006; Kristensen and Hansen, 2009), amplification and deletion of genomic regions (Cowell and Lo, 2009), and aberrant expression of repeated DNA sequences (Ting et al., 2011). Various molecular diagnostic assays such as mutational analysis, methylation status of genomic DNA, and gene expression analysis may detect these biomarkers and produce valuable information for patients, doctors, clinicians and researchers. So far, these assays primarily have been performed on cancer cells derived from surgically removed tumor tissue or from tissue obtained by biopsy. For example, PCA3, TMPRSS2:ERG, and ERG, have previously been shown through biopsy analysis to be differentially expressed in prostate cancer compared to normal prostate tissues (Bussemakers et al., 1999; Petrovics et al., 2005; Tomlins et al., 2005).

However, the ability to perform these tests using a bodily fluid sample is oftentimes more desirable than using a patient tissue sample. A less invasive approach using a bodily fluid sample has wide ranging implications in terms of patient welfare, the ability to conduct longitudinal disease monitoring, and the ability to obtain expression profiles even when tissue cells are not easily accessible, e.g., in the prostate gland.

The detection of prostate cancer markers such as PSA (also called KLK3), PCA3, TMPRSS2:ERG, and ERG using urine samples has previously been investigated (Hessels et al., 2007; Laxman et al., 2008; Laxman et al., 2006; Nguyen et al., 2011; Rice et al., 2010; Rostad et al., 2009; Salami et al., 2011; Tomlins et al., 2005). However, the sample collection methods previously disclosed required a digital rectal exam (DRE), or prostate massage, to enable enough prostate-derived cellular fluid to enter the urine. Samples collected without DRE or prostate massage showed a lower detection rate of these biomarkers. For example, the detection rate for TMPRSS2:ERG was about 69% with DRE but only about 24% without DRE (Rostad et al., 2009).

Indeed, current sample collection methods for urine analysis of prostate cancer biomarkers require the use of a DRE with a systematic application of mild digital pressure over the entire palpated surface of the prostate, digital pressure to the prostate with 3 sweeps of each lateral lobe, firm pressure to the prostate from the base to apex and from the lateral to the median line of each lobe, or firm pressure to the prostate from the base to apex and from the lateral to the median line (where the depression of the prostate surface was between 0.5 to 1 cm) of each lobe three times (Deras et al., 2008; Hessels et al., 2007; Laxman et al., 2008; Laxman et al., 2006; Nguyen et al., 2011; Rice et al., 2010; Salami et al., 2011).

In addition, sample preparation methods previously disclosed require the isolation of cellular pellets from the post-DRE urine sample by centrifugation (Hessels et al., 2007; Laxman et al., 2008; Laxman et al., 2006; Nguyen et al., 2011; Rostad et al., 2009; Salami et al., 2011).

Many prior studies suggest that a DRE is a critical step in enabling enough RNA material to be collected for non-invasive prostate gene analysis (Deras et al., 2008; Hessels et al., 2007; Laxman et al., 2008; Laxman et al., 2006; Nguyen et al., 2011; Rice et al., 2010; Rostad et al., 2009; Salami et al., 2011; Tomlins et al., 2011). In some of these studies, urine samples are required to be processed within 4 hours of collection (Deras et al., 2008; Tomlins et al., 2011).

In contrast to these previous sample collection and urinary biomarker detection methods, the methods provided herein do not require a DRE or prostate massage prior to urine sample collection, nor do these methods require a sample preparation step involving isolation of a cellular pellet from urine samples. These new, noninvasive methods use urinary microvesicles to detect biomarkers in aid of diagnosis, prognosis, monitoring, or therapy selection for a disease or other medical condition of the prostate gland. Microvesicles released by tumor cells can be used to determine the genetic status of the tumor (Skog et al., 2008). See also WO 2009/100029, WO 2011/009104, WO 2011/031892, and WO 2011/031877.

Microvesicles are shed by eukaryotic cells, or budded off of the plasma membrane, to the exterior of the cell. These membrane vesicles are heterogeneous in size with diameters ranging from about 10 nm to about 5000 nm. All membrane vesicles shed by cells that are less than 0.8 µm in diameter are referred to herein collectively as "microvesicles".

The present invention is based on the surprising finding that urine microvesicles contain biomarkers for a disease or other medical condition of the prostate gland in a subject. Thus, a patient urine sample can be assayed for detection of biomarkers for a disease or other medical condition of the prostate gland in a subject.

In the methods provided herein, random urine samples from subjects are collected without using a digital rectal exam (DRE) or prostatic massage prior to urine collection. The urine samples are 60 mL, 50 mL, 40 mL, 30 mL, 20 mL, 15 mL, or 10 mL. In some preferred embodiments, the urine samples are 40 mL or 20 mL. In some embodiments, the urine samples may be 1 to 40 mL, 1 to 35 mL, 1 to 30 mL, 1 to 25 mL, 1 to 20 mL, 1 to 15 mL, 1 to 10 mL, 1 to 5 mL, 5 to 40 mL, 5 to 35 mL, 5 to 30 mL, 5 to 25 mL, 5 to 20 mL, 5 to 15 mL, 5 to 10 mL, 10 to 40 mL, 10 to 35 mL, 10 to 30 mL, 10 to 25 mL, 10 to 20 mL, 10 to 15 mL, 15 to 40 mL, 15 to 35 mL, 15 to 30 mL, 15 to 25 mL, 15 to 20 mL, 20 to 40 mL, 20 to 35 mL, 20 to 30 mL, 20 to 25 mL, 25 to 40 mL, 25 to 35 mL, 25 to 30 mL, 30 to 40 mL, 30 to 35 mL, or 35 to 40 mL.

In a preferred embodiment, the urine sample is the urine that is first voided from the bladder, also known as "first catch" urine. The first voided urine contains the highest concentration of prostate-derived microvesicles, and therefore the analysis of the first voided urine provides higher signal from prostate biomarkers. As shown herein, the diagnostic accuracy of biomarkers useful in the diagnosis and prognosis of prostate cancer increases as the sample volume of the first voided urine sample decreases. The findings described herein demonstrate that 40 mL or 20 mL of the first voided urine exhibits greater diagnostic accuracy (i.e., AUC values). Accordingly, in a preferred embodiment, the urine samples are the first 40 mL or less, voided from the bladder. For example, the urine samples are the first 20 mL voided from the bladder.

Urine samples that are not suitable for use in the kits and/or methods of the disclosure include samples where the sample has not been properly stored and/or shipped. For example, specimens should not be kept at room temperature (e.g., 15-25° C.) for extended periods of time. In some embodiments, specimens should not be kept at room temperature (e.g., 15-25° C.) for more than 24 hours. In some embodiments, specimens should not be kept at room temperature (e.g., 15-25° C.) for more than 36 hours. In some embodiments, specimens should not be kept at room temperature (e.g., 15-25° C.) for more than 48 hours. Specimens should not be kept at a refrigerated temperature (e.g., 2-8° C.) for extended periods of time. For example, specimens should not be kept at a refrigerated temperature (e.g., 2-8° C.) for more than 21 days. In some embodiments, specimens should not be kept at a refrigerated temperature (e.g., 2-8° C.) for more than 30 days. Typically, specimens can be frozen (e.g., ≤70° C.) indefinitely. Specimens should be shipped on cold packs or on dry ice if the specimen is frozen.

Urine samples that are not suitable for use in the kits and/or methods of the disclosure include grossly bloody specimens.

The timing for collecting urine samples may also vary depending on different applications. A sample may be collected at any anytime as a spot urine sample. Spot urine may be sufficient for biomarker analyses when the amount of biomarker in microvesicles to be analyzed does not fluctuate too much during the day. In other cases, a 24-hour urine sample is collected when there is fluctuation of the amount of the biomarker in microvesicles to be analyzed and a 24-hour collection may mitigate the fluctuation effect. In still further cases, a series of urine samples are collected to study the fluctuation of the amount of biomarkers in microvesicles. The series of collections may be carried out in a certain time interval, e.g., every 6 hours, or in a scenario interval, e.g., before and after a therapeutic intervention.

In the methods provided herein, urine samples are first pre-processed by using a method comprising at least one filtration step. For example, a course filter (0.8 micron) is utilized to remove cells and cell debris. This filtration may be followed by an ultrafiltration step to remove solvent and small molecule analytes while retaining the microvesicles. The filters used in the initial filtration can be any size that is sufficient to remove cells and cell debris, for example, any size greater than 0.22 microns. To isolate the urine microvesicles, the pre-processed samples are then subjected to a filtration concentration step, wherein a filter that has a molecular weight cutoff is utilized to retain and concentrate the microvesicles that are greater than 10 nm in diameter. For example, the sample is then concentrated to a volume of less than 1 mL, preferably 100-200 µL. For example, the molecular weight cutoff is at least 100 kDa.

In some embodiments, the method for pre-processing and processing a urine sample includes the following steps. First, a portion of the urine sample, e.g., at least 20 mL, is processed using a 0.8 µm filter. For example, when the sample volume is ≤50 mL, at least 20 mL is drawn into a syringe that is attached to a 0.8 µm filter and then expressed into a clean vessel, e.g., a clean 50 mL tube. When the sample urine volume is ≥50 mL, the sample is filtered using a 0.8 µm bottle filter unit, and in some embodiments, suction is used to draw the sample through the bottle filter unit. Then, regardless of the initial sample volume, the filtered urine in the clean vessel is then subject to pulse vortex for a few seconds, e.g., 1-2 seconds. The filtered urine is then stored until filtrate concentration is ready to begin.

A portion of the filtered urine, e.g., 15 mL, is then processed using a filter concentrator (FC). Once the filtered urine is pipetted into the FC chamber (i.e., the top chamber of the FC vessel), an internal control, e.g., a Qbeta bacteriophage internal control (Attostar, Catalog #BAC200), can be added at the appropriate concentration. The FC vessel is then centrifuged. e.g., in a swing bucket rotor centrifuge, and spun for 5 minutes at 4,500×g at room temperature (e.g., 20-25° C.). If the sample fails to filter completely (>500 µL retentate remaining in the FC), then the FC should be re-centrifuged for 2-5 minutes. Samples that show minimal signs of filtering (>10 mL retentate remaining in the FC) should be discarded.

The sample is then removed from the centrifuge, and the filtrate (i.e., the fluid in the bottom of the FC vessel) is discarded. The retentate is then re-suspended with 5 mL of the remaining filtered urine and 10 mL 1×PBS. The sample is uniformly mixed, e.g., by inverting the FC vessel 3-4 times. The FC vessel is then centrifuged, e.g., in a swing bucket rotor centrifuge, and spun for 5 minutes at 4,500×g at room temperature (e.g., 20-25° C.). The sample is then removed from the centrifuge, and the filtrate is discarded.

In the first wash step, the retentate is re-suspended in in 15 mL 1×PBS. The sample is uniformly mixed, e.g., by inverting the FC vessel 3-4 times. The FC vessel is then centrifuged, e.g., in a swing bucket rotor centrifuge, and spun for 5 minutes at 4,500×g at room temperature (e.g., 20-25° C.).

In the second wash step, the retentate is re-suspended in in 15 mL 1×PBS. The sample is uniformly mixed, e.g., by inverting the FC vessel 3-4 times. The FC vessel is then centrifuged, e.g., in a swing bucket rotor centrifuge, and spun for 7 minutes at 4,500×g at room temperature (e.g., 20-25° C.). The expected retention volume is 100-200 µL. If the sample volume is greater than 250 µL, then the FC vessel is centrifuged for an additional 5 minutes at 4,500×g at RT.

After isolation and concentration of the urine microvesicles, the samples are pre-treated with an RNase inhibitor, prior to nucleic acid extraction, to prevent digestion of extracted RNA and enhance the quality of the extraction. Optionally, the samples may be washed at least once using the appropriate buffer to further enrich or purify the microvesicle fraction. In some embodiments, the samples are washed twice using the appropriate buffer to further enrich or purify the microvesicle fraction. RNA is extracted from the microvesicles by a method comprising lysis of the microvesicles, processing the lysate through an RNA-binding column, and elution of the RNA from the RNA-binding column, under appropriate conditions designed to achieve high quality RNA preparations. Optionally, the concentrated microvesicles are lysed on the filter used in the pre-processing step. These high quality RNA preparations provide urine-based molecular diagnostics for prostate cancer and other disorders of the prostate.

In some embodiments, 4 µL of an RNase Inhibitor is added to the upper chamber of the FC vessel. The vessel is then shaken laterally to ensure that the RNase inhibitor is well suspended. The sample is then incubated with the RNase Inhibitor for 2-3 minutes at room temperature (e.g., 15-25° C.). An RNA lysis buffer, e.g., Promega RNA Lysis Buffer (Catalog #Z3051) containing 2% 1-thiglycerol is then added at a volume of 250 µl to each sample. The sample is then briefly vortexed and incubated at room temperature for 1 minute.

A pipette is then placed at the bottom of the FC vessel (with care not to touch or scrape the sides of the vessel or the filter), and 150 µl of solution (i.e., sample+RNase inhibitor) is transferred to a 2 mL RNase free tube. This step is repeated until all sample has been removed and transferred to the 2 mL RNase free tube. The isolated microvesicle fraction is then ready for nucleic acid extraction, e.g., RNA extraction.

Isopropanol is then added to the 2 mL tube at a volume of 150 µl, and the solution is mixed by pipet. The lysate is transferred to the extraction column, and the extraction column is centrifuged for 30 seconds at 13,000×g. The extraction column is then transferred to a new collection tube, and the centrifuging for 30 seconds 13,000×g and transfer from extraction column to new collection tube is repeated until all lysate has been transferred. RNA Wash Solution (RWA Buffer) from Promega (Catalog #Z309B-C) is then added at a volume of 500 µl to the collection tube, and the tube is centrifuged for 30 seconds at 13,000×g. The sample is then transferred to a new collection tube, 300 µl of RWA Buffer is added to the collection tube, and the collection tube is then centrifuged for 2 minutes at 13,000×g. The sample is then transferred to a new collection tube, and the collection tube is then centrifuged for 2 minutes at 13,000× g. The contents of the collection tube are then transferred to a 1.5 mL Eppendorf® tube that is RNase DNase free. The contents of the tube are then eluted using 16 µl of nuclease-free water, e.g., Promega Nuclease-Free Water (Catalog #P119E) and centrifuged for 1 minute at 13,000×g.

The extracted RNA from the microvesicle fraction can then be stored at ≤−70° C. in an ultra-low freezer.

The methods described herein may include the use of a control particle to determine or evaluate the quality of the microvesicle isolation and/or microvesicle nucleic acid extraction. Control particles collectively refer to particles of the size range of microvesicles that are added at some point during the microvesicle isolation or nucleic acid extraction process, wherein the particles contain control nucleic acids, such as DNA or RNA. Specifically, the control nucleic acids comprise at least one target gene to be assayed or measured for determining the amount of recovery of the control particle during the isolation or extraction process.

Preferably, the control particle is a Q-beta bacteriophage, referred to herein as "Q-beta particle". The Q-beta particle used in the methods described herein may be a naturally-occurring virus particle or may be a recombinant or engineered virus, in which at least one component of the virus particle (e.g., a portion of the genome or coat protein) is synthesized by recombinant DNA or molecular biology techniques known in the art. Q-beta is a member of the leviviridae family, characterized by a linear, single-stranded RNA genome that consists of 3 genes encoding four viral proteins: a coat protein, a maturation protein, a lysis protein, and RNA replicase. Due to its similar size to average microvesicles, Q-beta can be easily purified from a biological sample using the same purification methods used to isolate microvesicles, as described herein. In addition, the low complexity of the Q-beta viral single-stranded gene structure is advantageous for its use as a control in amplification-based nucleic acid assays. The Q-beta particle contains a control target gene or control target sequence to be detected or measured for the quantification of the amount of Q-beta particle in a sample. For example, the control target gene is the Q-beta coat protein gene. After addition of the Q-beta particles to the urine sample or isolated urine-derived microvesicles, the nucleic acids from the Q-beta particle are extracted along with the nucleic acids from the microvesicles and/or urine sample using the extraction methods described herein. Detection of the Q-beta control target gene can be determined by RT-PCR analysis, for example, simultaneously with the biomarkers of interest (i.e., BIRC5, ERG and SPARCL1). A standard curve of at least 2, 3, or 4 known concentrations in 10-fold dilution of a control target gene can be used to determine copy number. The copy number detected and the quantity of Q-beta particle added can be compared to determine the quality of the isolation and/or extraction process.

In some embodiments, the kits and/or methods of the disclosure use a Q-beta particle that includes at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of SEQ ID NO: 1:

```
                                                      (SEQ ID NO: 1)
AAACGGTTCTTGTGACCCATCCGTTACTCGCCAGGCATATGCTGACGTGA

CCTTTTCGTTCACGCAGTATAGTACCGATGAGGAACGAGCTTTTGTTCGT

ACAGAGCTTGCTGCTCTGCTCGCTAGTCCTAGCGTCCTCAGTTAGATCCT

TATCAGATTCTTGGACCAACAAGTAGCCGCCTTGCAAATCCAGGCAGTGG

CCAGATCCAGCTTTGGCAGTTCCTCCTGGAGCTCCTGTCGGACAGCTCCC

GGTCGGATGTGCTGCTGGAGCCCTTCCGCCGCGGTGTCATGGAGAAACTC

CAGCTGGGCCCAGAGATTCTGCAGCGGGAAAACCTGTCCGTGACGTGGAT

TGGTGCTGCACCCCTCATCCTGTCTCGGATTGTGGGAGGCTGGGAGTGCG

AGAAGCATTCCCAACCCTGGCAGGTGCTTGTGGCCTCTCGTGGCAGGGCA

GTCTGCGGCGGTGTTCTGGTGCACCCCCAGTGGGTCCTCACAGCTGCCCA

CTGCATCAGGAACAAAAGCGTGATCTTGCTGGGTCGGCACAGC
```

In some embodiments, the Q-beta particles are added to the urine sample prior to nucleic extraction. For example, the Q-beta particles are added to the urine sample prior to ultrafiltration and/or after the pre-filtration step.

In some embodiments, 50, 100, 150, 200, 250, 300, 350, 400, 450, 500, 1,000 or 5,000 copies of Q-beta particles added to a urine sample. In some embodiments, 100 copies of Q-beta particles are added to a urine sample. The copy number of Q-beta particles can be calculated based on the ability of the Q-beta bacteriophage to infect target cells. Thus, the copy number of Q-beta particles is correlated to the colony forming units of the Q-beta bacteriophage.

The methods provided herein are useful in subjects suspected of having prostate cancer, for example, due to an elevated PSA, suspicious DRE or any other art-recognized technique for diagnosis of prostate cancer. In some embodiments, the methods provided herein are useful in subjects who have not had any prior diagnostic testing, such as PSA testing, DRE, or any other art-recognized technique for diagnosis of prostate cancer.

The methods provided herein demonstrate the association of biomarkers in urine microvesicles with the finding of prostate cancer as determined by a prostate biopsy. Prostate biopsy is the current standard for prostate cancer diagnosis, but the risks associated with prostate biopsy are significant, especially when considering that one million biopsies are performed in the United States, annually. Pain, bleeding, urinary retention and urinary tract infections are not uncommon, and serious life threatening infections may also occur.

The methods described herein provide methods of the non-invasive analysis of the RNA expression levels of cancer-associated transcripts in urine samples or urinary microvesicles. In particular, the methods are used to detect the mRNA expression of at least PCA3 and ERG in urine samples. ERG mRNAs may include one or more isoforms of ERG include ERG1, ERG2, ERG3, ERG4, ERG5, ERG6, ERG7, ERG8, ERG9, ERG Prostate Cancer-specific Isoform 1 (EPC1) and ERG Prostate Cancer-specific Isoform 2 (EPC2). As demonstrated herein, detecting expression levels of PCA3 and ERG in urinary microvesicles provides excellent sensitivity and specificity as biomarkers of prostate cancer and other prostate-related disorders in subjects who had previously undergone a prostate biopsy (referred to herein as the biopsy cohort or patient cohort). In some embodiments, 2, 3, 4, 5, 6, 7, 8, 9, or 10 or more biomarkers are detected in combination.

In some embodiments, the kits and/or methods of the disclosure are used to detect ERG mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, and/or at least 250 nucleotides or more of the following nucleic acid sequence:

```
                                                      (SEQ ID NO: 2)
CAGTCGAAAGCTGCTCAACCATCTCCTTCCACAGTGCCCAAAACTGAAG

ACCAGCGTCCTCAGTTAGATCCTTATCAGATTCTTGGACCAACAAGTAG

CCGCCTTGCAAATCCAGGCAGTGGCCAGATCCAGCTTTGGCAGTTCCTC

CTGGAGCTCCTGTCGGACAGCTCCAACTCCAGCTGCATCACCTGGGAAG

GCACCAACGGGGAGTTCAAGATGACGGATCCCGACGAGGTGGCCCGGCG

CTGGGGAGAGCGGAAGAGCAAACCCAACATGAACTACGATAAGCTCAGC

CGCGCC
```

As shown herein, PCA3 and ERG were analyzed by univariate analysis and demonstrated that each gene alone (when normalized to a reference gene such as KLK3) had high diagnostic accuracy (AUC values greater than 0.6). The analysis disclosed herein shows that PCA3 and ERG had more diagnostic value when the normalized expression level of both was determined together than alone.

In some embodiments, the kits and/or methods of the disclosure are used to detect PCA3 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, and/or at least 450 nucleotides or more of the nucleic acid sequence of

```
                                                      (SEQ ID NO: 3)
GGGAGACGAAUUGGGCCCUCUAGAUGCAUGCUCGAGCGGCCGCCAGUGUG

AUGGAUAUCUGCAGAAUUCGCCCUUAUUGUCUCCUCAGUGACACAGGGCU

GGAUCACCAUCGACGGCACUUUCUGAGUACUCAGUGCAGCAAAGAAAGAC

UACAGACAUCUCAAUGGCAGGGGUGAGAAAUAAGAAAGGCUGCUGACUUU

ACCAUCUGAGGCCACACAUCUGCUGAAAUGGAGAUAAUUAACAUCACUAG

AAACAGCAAGAUGACAAUAUAAUGUCUAAGUAGUGACAUGUUUUGCACAU

UUCCAGCCCCUUUAAAUAUCCACACACACAGGAAGCACAAAAGGAAGCAC

AGAGAUCCCUGGGAGAAAUGCCCGGCCACCUGCGGCCGCAAGCUUGGAUC

CGAAUUCCUGUGUGAAAUUGUUAUCCGCUCACAAUUCCACACAACAUACG

AGCCGGAAGCAUAAAGUGUAAAGCCUGGGGUGCCUAAUGA
```

In some embodiments, the kits and/or methods of the disclosure are used to detect ERG mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, and/or at least 250 nucleotides or more of the nucleic acid sequence of SEQ ID NO: 2 and PCA3 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, and/or at least 450 nucleotides or more of the nucleic acid sequence of SEQ ID NO: 3.

In some embodiments, the kits and/or methods of the disclosure are used to detect ERG mRNA having the full-length nucleic acid sequence of SEQ ID NO: 2 and PCA3 mRNA having the full-length nucleic acid sequence of SEQ ID NO: 3.

Additional biomarker combinations can be used with PCA3 and ERG, wherein 1, 2, 3, 4, 5, 6, 7, 8, 9, or 10 or more additional genes may have high diagnostic value as biomarkers for cancer, such as aggressive cancers or prostate cancer. Examples of these additional genes include AMACR, BIRC5, HOXC6, and SPARCL1.

In some embodiments, the kits and/or methods of the disclosure are used to detect AMACR mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of SEQ ID NO: 4, SEQ ID NO: 37, or SEQ ID NO: 38:

```
Human AMACR, transcript variant 1, mRNA (SEQ ID NO: 4)

(SEQ ID NO: 4)
GGGGCCTGGCGCCGGGGATTGGGAGGGCTTCTTGCAGGCTGCTGGGCTGGGGCTAAGGGCT

GCTCACTTTCCTTCAGCGGGGCACTGGGAAGCGCCATGGCACTGCAGGGCATCTCGGTCGT

GGAGCTGTCCGGCCTGGCCCCGGGCCCGTTCTGTGCTATGGTCCTGGCTGACTTCGGGGCG

CGTCTCGTACGCGTGGACCGGCCCGGCTCCCGCTACGACGTGAGCCGCTTGGGCCGGGGCA

AGCGCTCGCTAGTGCTGGACCTGAAGCAGCCGCGGGGAGCCGCCGTGCTGCGGCGTCTGTC

CAAGCGGTCGGATGTGCTGCTGGAGCCCTTCCGCCGCGGTGTCATGGAGAAACTCCAGCTG

GGCCCAGAGATTCTGCAGCGGGAAAATCCAAGGCTTATTTATGCCAGGCTGAGTGGATTTG

GCCAGTCAGGAAGCTTCTGCCGGTTAGCTGGCCACGATATCAACTATTTGGCTTTGTCAGG

TGTTCTCTCAAAAATTGGCAGAAGTGGTGAGAATCCGTATGCCCCGCTGAATCTCCTGGCT

GACTTTGCTGGTGGTGGCCTTATGTGTGCACTGGGCATTATAATGGCTCTTTTTGACCGCA

CACGCACTGGCAAGGGTCAGGTCATTGATGCAAATATGGTGGAAGGAACAGCATATTTAAG

TTCTTTTCTGTGGAAAACTCAGAAATTGAGTCTGTGGGAAGCACCTCCAGGACAGAACATG

TTGGATGGTGGAGCACCTTTCTATACGACTTACAGGACAGCAGATGGGGAATTCATGGCTG

TTGGAGCAATAGAACCCCAGTTCTACGAGCTGCTGATCAAAGGACTTGGACTAAAGTCTGA

TGAACTTCCCAATCAGATGAGCATGGATGATTGGCCAGAAATGAAGAAGAAGTTTGCAGAT

GTATTTGCAGAGAAGACGAAGGCAGAGTGGTGTCAAATCTTTGACGGCACAGATGCCTGTG

TGACTCCGGTTCTGACTTTTGAGGAGGTTGTTCATCATGATCACAACAAGGAACGGGGCTC

GTTTATCACCAGTGAGGAGCAGGACGTGAGCCCCCGCCCTGCACCTCTGCTGTTAAACACC

CCAGCCATCCCTTCTTTCAAAAGGGATCCTTTCATAGGAGAACACACTGAGGAGATACTTG

AAGAATTTGGATTCAGCCGCGAAGAGATTTATCAGCTTAACTCAGATAAAATCATTGAAAG

TAATAAGGTAAAAGCTAGTCTCTAACTTCCAGGCCCACGGCTCAAGTGAATTTGAATACTG

CATTTACAGTGTAGAGTAACACATAACATTGTATGCATGGAAACATGGAGGAACAGTATTA

CAGTGTCCTACCACTCTAATCAAGAAAAGAATTACAGACTCTGATTCTACAGTGATGATTG

AATTCTAAAAATGGTTATCATTAGGGCTTTTGATTTATAAAACTTTGGGTACTTATACTAA

ATTATGGTAGTTATTCTGCCTTCCAGTTTGCTTGATATATTTGTTGATATTAAGATTCTTG

ACTTATATTTTGAATGGGTTCTAGTGAAAAAGGAATGATATATTCTTGAAGACATCGATAT

ACATTTATTTACACTCTTGATTCTACAATGTAGAAAATGAGGAAATGCCACAAATTGTATG

GTGATAAAAGTCACGTGAAACAGAGTGATTGGTTGCATCCAGGCCTTTTGTCTTGGTGTTC

ATGATCTCCCTCTAAGCACATTCCAAACTTTAGCAACAGTTATCACACTTTGTAATTTGCA

AAGAAAAGTTTCACCTGTATTGAATCAGAATGCCTTCAACTGAAAAAAACATATCCAAAAT

AATGAGGAAATGTGTTGGCTCACTACGTAGAGTCCAGAGGGACAGTCAGTTTTAGGGTTGC
```

-continued

```
CTGTATCCAGTAACTCGGGGCCTGTTTCCCCGTGGGTCTCTGGGCTGTCAGCTTTCCTTTC

TCCATGTGTTTGATTTCTCCTCAGGCTGGTAGCAAGTTCTGGATCTTATACCCAACACACA

GCAACATCCAGAAATAAAGATCTCAGGACCCCCCAGCAAGTCGTTTTGTGTCTCCTTGGAC

TGAGTTAAGTTACAAGCCTTTCTTATACCTGTCTTTGACAAAGAAGACGGGATTGTCTTTA

CATAAAACCAGCCTGCTCCTGGAGCTTCCCTGGACTCAACTTCCTAAAGGCATGTGAGGAA

GGGGTAGATTCCACAATCTAATCCGGGTGCCATCAGAGTAGAGGGAGTACAGAATGGATGT

TGGGTAGGCCATCAATAAGGTCCATTCTGCGCAGTATCTCAACTGCCGTTCAACAATCGCA

AGAGGAAGGTGGAGCAGGTTTCTTCATCTTACAGTTGAGAAAACAGAGACTCAGAAGGGCT

TCTTAGTTCATGTTTCCCTTAGCGCCTCAGTGATTTTTTCATGGTGGCTTAGGCCAAAAGA

AATATCTAACCATTCAATTTATAAATAATTAGGTCCCCAACGAATTAAATATTATGTCCTA

CCAACTTATTAGCTGCTTGAAAAATATAATACACATAAATAAAAAAATATATTTTTCATTT

CTATTTCATTGTTAATCACAACTACTTACTAAGGAGATGTATGCACCTATTGGACACTGTG

CAACTTCTCACCTGGAATGAGATTGGACACTGCTGCCCTCATTTTCTGCTCCATGTTGGTG

TCCATATAGTACTTGATTTTTTATCAGATGGCCTGGAAAACCCAGTCTCACAAAAATATGA

AATTATCAGAAGGATTATAGTGCAATCTTATGTTGAAAGAATGAACTACCTCACTAGTAGT

TCACGTGATGTCTGACAGATGTTGAGTTTCATTGTGTTTGTGTGTTCAAATTTTTAAATAT

TCTGAGATACTCTTGTGAGGTCACTCTAATGCCCTGGGTGCCTTGGCACAGTTTTAGAAAT

ACCAGTTGAAAATATTTGCTCAGGAATATGCAACTAGGAAGGGGCAGAATCAGAATTTAAG

CTTTCATATTCTAGCCTTCAGTCTTGTTCTTCAACCATTTTTAGGAACTTTCCCATAAGGT

TATGTTTTCCAGCCCAGGCATGGAGGATCACTTGAGGCCAAGAGTTCGAGACCAGCCTGGG

GAACTTGGCTGGACCTCCGTTTCTACGAAATAAAAATAAAAAAATTATCCAGGTATGGTGG

TGTGTGCCTGTAGTCCTATCTACTCAAGGGTGGGCAGGAGGATCACTTGAGCCCAGGAAT

TTGAGGCCACAGTGAATTAGGATTGCACCACTGCACTCTAGCCCAGGCAACAGAACAAGAA

CCTGTCTCTAAATAAATAAATAAAAATAATAATAATAAAAAAGATGTTTTCCCTACAA
```

Human AMACR, transcript variant 1, mRNA (SEQ ID NO: 37)

(SEQ ID NO: 37)
```
GGGGCCTGGCGCCGGGGATTGGGAGGGCTTCTTGCAGGCTGCTGGGCTGGGGCTAAGGGCT

GCTCACTTTCCTTCAGCGGGGCACTGGGAAGCGCCATGGCACTGCAGGGCATCTCGGTCGT

GGAGCTGTCCGGCCTGGCCCCGGGCCCGTTCTGTGCTATGGTCCTGGCTGACTTCGGGGCG

CGTCTCGTACGCGTGGACCGGCCCGGCTCCCGCTACGACGTGAGCCGCTTGGGCCGGGGCA

AGCGCTCGCTAGTGCTGGACCTGAAGCAGCCGCGGGGAGCCGCCGTGCTGCGGCGTCTGTC

CAAGCGGTCGGATGTGCTGCTGGAGCCCTTCCGCCGCGGTGTCATGGAGAAACTCCAGCTG

GGCCCAGAGATTCTGCAGCGGGAAAATCCAAGGCTTATTTATGCCAGGCTGAGTGGATTTG

GCCAGTCAGGAAGCTTCTGCCGGTTAGCTGGCCACGATATCAACTATTTGGCTTTGTCAGG

TGGAAGGAACAGCATATTTAAGTTCTTTTCTGTGGAAAACTCAGAAATTGAGTCTGTGGGA

AGCACCTCGAGGACAGAACATGTTGGATGGTGGAGCACCTTTCTATACGACTTACAGGACA

GCAGATGGGAATTCATGGCTGTTGGAGCAATAGAACCCCAGTTCTACGAGCTGCTGATCA

AAGGACTTGGACTAAAGTCTGATGAACTTCCCAATCAGATGAGCATGGATGATTGGCCAGA

AATGAAGAAGTTTGCAGATGTATTTGCAGAGAAGACGAAGGCAGAGTGGTGTCAAATC

TTTGACGGCACAGATGCCTGTGTGACTCCGGTTCTGACTTTTGAGGAGGTTGTTCATCATG

ATCACAACAAGGAACGGGGCTCGTTTATCACCAGTGAGGAGCAGGACGTGAGCCCCCGCCC
```

-continued

```
TGCACCTCTGCTGTTAAACACCCCAGCCATCCCTTCTTTCAAAAGGGATCCTTTCATAGGA

GAACACACTGAGGAGATACTTGAAGAATTTGGATTCAGCCGCGAAGAGATTTATCAGCTTA

ACTCAGATAAAATCATTGAAAGTAATAAGGTAAAAGCTAGTCTCTAACTTCCAGGCCCACG

GCTCAAGTGAATTTGAATACTGCATTTACAGTGTAGAGTAACACATAACATTGTATGCATG

GAAACATGGAGGAACAGTATTACAGTGTCCTACCACTCTAATCAAGAAAAGAATTACAGAC

TCTGATTCTACAGTGATGATTGAATTCTAAAAATGGTTATCATTAGGGCTTTTGATTTATA

AAACTTTGGGTACTTATACTAAATTATGGTAGTTATTCTGCCTTCCAGTTTGCTTGATATA

TTTGTTGATATTAAGATTCTTGACTTATATTTTGAATGGGTTCTAGTGAAAAAGGAATGAT

ATATTCTTGAAGACATCGATATACATTTATTTACACTCTTGATTCTACAATGTAGAAAATG

AGGAAATGCCACAAATTGTATGGTGATAAAAGTCACGTGAAACAGAGTGATTGGTTGCATC

CAGGCCTTTTGTCTTGGTGTTCATGATCTCCCTCTAAGCACATTCCAAACTTTAGCAACAG

TTATCACACTTTGTAATTTGCAAAGAAAAGTTTCACCTGTATTGAATCAGAATGCCTTCAA

CTGAAAAAAACATATCCAAAATAATGAGGAAATGTGTTGGCTCACTACGTAGAGTCCAGAG

GGACAGTCAGTTTTAGGGTTGCCTGTATCCAGTAACTCGGGGCCTGTTTCCCCGTGGGTCT

CTGGGCTGTCAGCTTTCCTTTCTCCATGTGTTTGATTTCTCCTCAGGCTGGTAGCAAGTTC

TGGATCTTATACCCAACACACAGCAACATCCAGAAATAAAGATTTCAGGACCCCCCAGCAA

GTCGTTTTGTGTCTCCTTGGACTGAGTTAAGTTACAAGCCTTTCTTATACCTGTCTTTGAC

AAAGAAGACGGGATTGTCTTTACATAAAACCAGCCTGCTCCTGGAGCTTCCCTGGACTCAA

CTTCCTAAAGGCATGTGAGGAAGGGGTAGATTCCACAATCTAATCCGGGTGCCATCAGAGT

AGAGGGAGTAGAGAATGGATGTTGGGTAGGCCATCAATAAGGTCCATTCTGCGCAGTATCT

CAACTGCCGTTCAACAATCGCAAGAGGAAGGTGGAGCAGGTTTCTTCATCTTACAGTTGAG

AAAACAGAGACTCAGAAGGGCTTCTTAGTTCATGTTTCCCTTAGCGCCTCAGTGATTTTTT

CATGGTGGCTTAGGCCAAAAGAAATATCTAACCATTCAATTTATAAATAATTAGGTCCCCA

ACGAATTAAATATTATGTCCTACCAACTTATTAGCTGCTTGAAAAATATAATACACATAAA

TAAAAAAATATATTTTTCATTTCTATTTCATTGTTAATCACAACTACTTACTAAGGAGATG

TATGGACCTATTGGACACTGTGCAACTTCTCACCTGGAATGAGATTGGACACTGCTGCCGT

CATTTTCTGCTCCATGTTGGTGTGCATATAGTACTTGATTTTTTATCAGATGGCCTGGAAA

ACCCAGTCTCACAAAAATATGAAATTATCAGAAGGATTATAGTGCAATCTTATGTTGAAAG

AATGAACTACCTCACTAGTAGTTCACGTGATGTCTGACAGATGTTGACTTTCATTGTGTTT

GTGTGTTCAAATTTTTAAATATTCTGAGATACTCTTGTGAGGTCACTCTAATGCCCTGGGT

GCGTTGGCACAGTTTTAGAAATACCAGTTGAAAATATTTGGTCAGGAATATGCAACTAGGA

AGGGGCAGAATCAGAATTTAAGCTTTCATATTCTAGCCTTCAGTCTTGTTCTTCAACCATT

TTTAGGAACTTTCCCATAAGGTTATGTTTTCCAGCCCAGGCATGGAGGATCACTTGAGGCC

AAGAGTTCGAGACCAGCCTGGGGAACTTGGCTGGACCTCCGTTTCTACGAAATAAAAATAA

AAAAATTATCCAGGTATGGTGGTGTGTGCCTGTAGTCCTATCTACTCAAGGGTGGGSCAGG

AGGATCACTTGAGCCCAGaAATTTGAGGCCACAGTGAATTAGGATTGCACCACTGCACTGT

AGGCCAGGCAACAGAACAAGAACCTGTCTCTAAATAAATAAATAAAAATAATAATAATAAA

AAAGATGTTTTCCCTACAA
```

-continued

Human AMACR, transcript variant 1, mRNA (SEQ ID NO: 38)

(SEQ ID NO: 38)
GGGGCGTGGCGCCGGGGATTGGGAGGGCTTCTTGCAGGCTGCTGGGCTGGGGCTAAGGGGT

GCTCAGTTTCCTTCAGCGGGGCACTGGGAAGCGCCATGGCACTGCAGGGCATCTCGGTCGT

GGAGCTGTCCGGCCTGGCCCCGGGCGCGTTCTGTGCTATGGTGCTGGCTGACTTCGGGGGG

CGTGTGGTACGCGTGGACCGGCCGGGCTCCCGCTACGACGTGAGCCGCTTGGGCCGGGGCA

AGGGGTGGCTAGTGCTGGACCTGAAGCAGCCGCGGGGAGCCGGCGTGCTGCGGCGTCTGTG

CAAGCGGTCGGATGTGCTGCTGGAGCCCTTCCGCCGCGGTGTCATGGAGAAACTCCAGCTG

GGCCCACAGATTCTGCAGCGGGAAAATCCAAGGCTTATTTATGCCAGGCTGAGTGGATTTG

GCCAGTCAGGAAGCTTCTGCCGGTTAGCTGGCCACGATATCAACTATTTGGCTTTGTCAGG

TGTTCTCTCAAAAATTGGCAGAAGTGGTGAGAATCCGTATGCCCCGCTGAATCTCCTGGCT

GACTTTGCTGGTGGTGGCCTTATGTGTGCACTGGGCATTATAATGGCTCTTTTTGACCGCA

CACGCACTGGCAAGGGTCAGGTCATTGATGCAAATATGGTGGAAGGAACAGCATATTTAAG

TTCTTTTCTGTGGAAAACTCAGAAATTGAGTCTGTGGGAAGCACCTCGAGGACAGAACATG

TTGGATGGTGGAGCACCTTTCTATACGACTTACAGGACAGCAGATGGGGAATTCATGGCTG

TTGGAGCAATAGAACCCCAGTTCTACGAGCTGCTGATCAAAGGACTTGGACTAAAGTCTGA

TGAACTTCCCAATCAGATGAGCATGGATGATTGGCCAGAAATGAAGAAGAAGTTTGCAGAT

GTATTTGCAGAGAAGACGAAGGCAGAGTGGTGTCAAATCTTTGACGGCACAGATGCCTGTG

TGACTCCGGTTCTGACTTTTGAGGAGGTTGTTCATCATGATCACAACAAGGAACGGGGCTC

GTTTATCACCAGTGAGGAGCAGGACGTGAGCCCCCGCCCTGCACCTCTGCTGTTAAACACC

CCAGCCATCCCTTCTTTCAAAAGGGATCCTTTCATAGGAGAACACACTGAGGAGATACTTG

AAGAATTTGGATTCAGCCGCGAAGAGATTTATCAGCTTAACTCAGATAAAATCATTGAAAG

TAATAAGGCTGGTAGCAAGTTCTGGATCTTATACCCAACACACAGCAACATCCAGAAATAA

AGATCTCAGGACCCCCCAGCAAGTCGTTTTGTGTCTCCTTGGACTGAGTTAAGTTACAAGC

CTTTCTTATACCTGTCTTTGACAAAGAAGACGGGATTGTCTTTACATAAAACCAGCCTGCT

CCTGGAGCTTCCCTGGACTCAACTTCCTAAAGGCATGTGAGGAAGGGGTAGATTCCACAAT

CTAATCCGGGTGCCATCAGAGTAGAGGGAGTAGAGAATGGATGTTGGGTAGGCCATCAATA

AGGTCCATTCTGCGCAGTATCTCAACTGCCGTTCAACAATCGCAAGAGGAAGGTGGAGCAG

GTTTCTTCATCTTACAGTTGAGAAAACAGAGACTCAGAAGGGCTTCTTAGTTCATGTTTCC

CTTAGCGCCTCAGTGATTTTTTCATGGTGGCTTAGGCCAAAAGAAATATCTAACCATTCAA

TTTATAAATAATTAGGTCCCCAACGAATTAAATATTATGTCCTACCAACTTATTAGCTGCT

TGAAAAATATAATACACATAAATAAAAAAATATATTTTTCATTTCTATTTCATTGTTAATC

ACAACTACTTACTAAGGAGATGTATGCACCTATTGGACACTGTGCAACTTCTCACCTGGAA

TGAGATTGGACACTGCTGCCCTCATTTTCTGCTCCATGTTGGTGTCCATATAGTACTTGAT

TTTTTATCAGATGGCCTGGAAAACCCAGTCTCACAAAAATATGAAATTATCGAAGGATTA

TAGTGCAATCTTATGTTGAAAGAATGAACTACCTCACTAGTAGTTCACGTGATGTCTGACA

GATGTTGAGTTTCATTGTGTTTGTGTGTTCAAATTTTTAAATATTCTGAGATACTCTTGTG

AGGTCACTCTAATGCCCTGGGTGCCTTGGCACAGTTTTAGAAATACCAGTTGAAAATATTT

GCTCAGGAATATGCAACTAGGAAGGGGCAGAATCAGAATTTAAGCTTTCATATTCTAGCCT

TCAGTCTTGTTCTTCAACCATTTTTAGGAACTTTCCCATAAGGTTATGTTTTCCAGCCCAG

GCATGGAGGATCACTTGAGGCCAAGAGTTCGAGACCAGCCTGGGGAACTTGGCTGGACCTC

-continued

```
CGTTTCTACGAAATAAAAATAAAAAAATTATCCAGGTATGGTGGTGTGTGCCTGTAGTCCT

ATCTACTCAAGGGTGGGGCAGGAGGATCACTTGAGCCCAGGAATTTGAGGCCACAGTGAAT

TAGGATTGCACCACTGCACTGTAGGCCAGGCAACAGAACAAGAACCTGTCTGTAAATAAAT

AAATAAAAATAATAATAATAAAAAAGATGTTTTCCCTACAA
```

In some embodiments, the kits and/or methods of the disclosure are used to detect BIRC5 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of SEQ ID NO: 5, SEQ ID NO: 39, or SEQ ID NO: 40:

Human BIRC5, Transcript Variant 1, mRNA (SEQ ID NO: 5)

(SEQ ID NO: 5)
```
CCCAGAAGGCCGCGGGGGGTGGACCGCCTAAGAGGGCGTGCGCTCCCGACATGCCCCGCGG

CGCGCCATTAACCGCCAGATTTGAATCGCGGGACCCGTTGGCAGAGGTGGCGGCGGCGGCA

TGGGTGCCCCGACGTTGCCCCCTGCCTGGCAGCCCTTTCTCAAGGACCACCGCATCTCTAC

ATTCAAGAACTGGCCCTTCTTGGAGGGCTGCGCCTGCACCCCGGAGCGGATGGCCGAGGCT

GGCTTCATCCACTGCCCCACTGAGAACGAGCCAGACTTGGCCCAGTGTTTCTTCTGCTTCA

AGGAGCTGGAAGGCTGGGAGCCAGATGACGACCCCATAGAGGAACATAAAAAGCATTCGTC

CGGTTGCGCTTTCCTTTCTGTCAAGAAGCAGTTTGAAGAATTAACCCTTGGTGAATTTTTG

AAACTGGACAGAGAAAGAGCCAAGAACAAAATTGCAAAGGAAACCAACAATAAGAAGAAAG

AATTTGAGGAAACTGCGGAGAAAGTGCGCCGTGCCATCGAGCAGCTGGCTGCCATGGATTG

AGGCCTCTGGCCGGAGCTGCCTGGTCCCAGAGTGGCTGCACCACTTCCAGGGTTTATTCCC

TGGTGCCACCAGCCTTCCTGTGGGCCCCTTAGCAATGTCTTAGGAAAGGAGATCAACATTT

TCAAATTAGATGTTTCAACTGTGCTCTTGTTTTGTCTTGAAAGTGGCACCAGAGGTGCTTC

TGCCTGTGCAGCGGGTGCTGCTGGTAACAGTGGCTGCTTCTCTCTCTCTCTCTTTTTTG

GGGGCTCATTTTTGCTGTTTTGATTCCCGGGCTTACCAGGTGAGAAGTGAGGGAGGAAGAA

GGCAGTGTCCCTTTTGCTAGAGCTGACAGCTTTGTTCGCGTGGGCAGAGCCTTCCACAGTG

AATGTGTCTGGACCTCATGTTGTTGAGGCTGTCACAGTCCTGAGTGTGGACTTGGCAGGTG

CCTGTTGAATCTGAGCTGCAGGTTCCTTATCTGTCACACCTGTGCCTCCTCAGAGGACAGT

TTTTTTGTTGTTGTGTTTTTTTGTTTTTTTTTTTTGGTAGATGCATGACTTGTGTGTGAT

GAGAGAATGGAGACAGAGTCCCTGGCTCCTCTACTGTTTAACAACATGGCTTTCTTATTTT

GTTTGAATTGTTAATTCACAGAATAGCACAAACTACAATTAAAACTAAGCACAAAGCCATT

CTAAGTCATTGGGGAAACGGGGTGAACTTCAGGTGGATGAGGAGACAGAATAGAGTGATAG

GAAGCGTCTGGCAGATACTCCTTTTGCCACTGCTGTGTGATTAGACAGGCCCAGTGAGCCG

CGGGGCACATGCTGGCCGCTCCTCCCTCAGAAAAAGGCAGTGGCCTAAATCCTTTTTAAAT

GACTTGGCTCGATGCTGTGGGGGACTGGCTGGGCTGCTGCAGGCCGTGTGTCTGTCAGCCC

AACCTTCACATCTGTCACGTTCTCCACACGGGGGAGAGACGCAGTCCGCCCAGGTCCCCGC

TTTCTTTGGAGGCAGCAGCTCCCGCAGGGCTGAAGTCTGGCGTAAGATGATGGATTTGATT

CGCCCTCCTCCCTGTCATAGAGCTGCAGGGTGGATTGTTACAGCTTCGCTGGAAACCTCTG

GAGGTCATCTCGGCTGTTCCTGAGAAATAAAAAGCCTGTCATTTCAAACACTGCTGTGGAC

CCTACTGGGTTTTTAAAATATTGTCAGTTTTTCATCGTCGTCCCTAGCCTGCCAACAGCCA

TCTGCCCAGACAGCCGCAGTGAGGATGAGCGTCCTGGCAGAGACGCAGTTGTCTCTGGGCG
```

CTTGCCAGAGCCACGAACCCCAGACCTGTTTGTATCATCCGGGCTCCTTCCGGGCAGAAAC
AACTGAAAATGCACTTCAGACCCAVTTATTTCTGCCACATCTGAGTCGGCCTGAGATAGAC
TTTTCCCTCTAAACTGGGAGAATATCACAGTGGTTTTTGTTAGCAGAAAATGCACTCCAGC
CTCTGTACTCATCTAAGCTGCTTATTTTTGATATTTGTGTCAGTCTGTAAATGGATACTTC
ACTTTAATAACTGTTGCTTAGTAATTGGCTTTGTAGAGAAGCTGGAAAAAAATGGTTTTGT
CTTCAACTCCTTTGCATGCCAGGCGGTGATGTGGATCTCGGCTTCTGTGAGCCTGTGCTGT
GGGCAGGGCTGAGCTGGAGCCGCCCCTCTCAGCCCGCCTGCCACGGCCTTTCCTTAAAGGC
CATCCTTAAAACCAGACCCTCATGGCTACCAGCACCTGAAAGCTTCCTCGACATCTGTTAA
TAAAGCCGTAGGCCCTTGTCTAAGTGCAACCGCCTAGACTTTCTTTCAGATACATGTCCAC
ATGTCCATTTTTCAGGTTCTCTAAGTTGGAGTGGAGTCTGGGAAGGGTTGTGAATGAGGCT
TCTGGGCTATGGGTGAGGTTCCAATGGCAGGTTAGAGCCCCTCGGGCCAACTGCCATCCTG
GAAAGTAGAGACAGCAGTGCCCGCTGCCCAGAAGAGACCAGCAAGCCAAACTGGAGCCCCC
ATTGCAGGCTGTCGCCATGTGGAAAGAGTAACTCACAATTGCCAATAAAGTCTCATGTGGT
TTTATCTAAAAAAAAAAAAAAAAAAAAAAAAA

Human BIRC5, Transcript Variant 2, mRNA (SEQ ID NO: 39)

(SEQ ID NO: 39)
CCCAGAAGGCCGCGGGGGGTGGACCGCCTAAGAGGGCGTGCGCTCCCGACATGCCCCGCGG
CGCGCCATTAACCGCCAGATTTGAATCGCGGGACCCGTTGGCAGAGGTGGCGGCGGCGGCA
TGGGTGCCCCGACGTTGCCCCCTGCCTGGCAGCCCTTTCTCAAGGACCACCGCATCTCTAC
ATTCAAGAACTGGCCCTTCTTGGAGGGCTGCGCCTGCACCCCGGAGCGGATGGCCGAGGCT
GGCTTCATCCACTGCCCCACTGAGAACGAGCCAGACTTGGCCCAGTGTTTCTTCTGCTTCA
AGGAGCTGGAAGGCTGGGAGCCAGATGACGACCCCATGCAAAGGAAACCAACAATAAGAAG
AAAGAATTTGAGGAAACTGCGGAGAAAGTGCGCCGTGCCATCGAGCAGCTGGCTGCCATGG
ATTGAGGCCTCTGGCCGGAGCTGCCTGGTCCCAGAGTGGCTGCACCACTTCCAGGGTTTAT
TCCCTGGTGCCACCAGCCTTCCTGTGGGCCCCTTAGCAATGTCTTAGGAAAGGAGATCAAC
ATTTTCAAATTAGATGTTTCAACTGTGCTCTTGTTTTGTCTTGAAAGTGGCACCAGAGGTG
CTTCTGCCTGTGCAGCGGGTGCTGCTGGTAACAGTGGCTGCTTCTCTCTCTCTCTCTCTTT
TTTGGGGGCTCATTTTTGCTGTTTTGATTCCCGGGCTTACCAGGTGAGAAGTGAGGGAGGA
AGAAGGCAGTGTCCCTTTTGCTAGAGCTGACAGCTTTGTTCGCGTGGGCAGAGCCTTCCAC
AGTGAATGTGTCTGGACCTCATGTTGTTGAGGCTGTCACAGTCCTGAGTGTGGACTTGGCA
GGTGCCTGTTGAATCTGAGCTGCAGGTTCCTTATCTGTCACACCTGTGCCTCCTCAGAGGA
CAGTTTTTTGTTGTTGTTTTTTGTTTTTTTTTTTGGTAGATGCATGACTTGTGTG
TGATGAGAGAATGGAGACAGAGDOCCTGGCTCCTCTACTGTTTAACAACATGGCTTTCTTA
TTTTGTTTGAATTGTTAATTCACAGAATAGCACAAACTACAATTAAAACTAAGCACAAAGC
CATTCTAAGTCATTGGGGAAACGGGGTGAACTTCAGGTGGATGAGGAGACAGAATAGAGTG
ATAGGAAGCGTCTGGCAGATACTCCTTTTGCCACTGCTGTGTGATTAGACAGGCCCAGTGA
GCCGGGGGGCACATGCTGGCCGCTCGTCCCTCAGAAAAGGCAGTGGCCTAAATCCTTTTT
AAATGACTTGGCTCGATGCTGTGGGGACTGGCTGGGCTGGTGCAGGCCGTGTGTCTGTCA
GCCCAACCTTCACATCTGTCACGTTGTCCACACGGGGGAGAGACGCAGTCCGCCCAGGTCC
CCGCTTTCTTTGGAGGCAGCAGCTCGCGCAGGGCTGAAGTGTGGCGTAAGATGATGGATTT
GATTGGGCCTCCTCCCTGTCATAGAGCTGCAGGGTGGATTGTTACAGCTTCGCTGGAAACC

-continued

TCTGGAGGTCATCTCGGCTGTTCGTGAGAAATAAAAAGCCTGTCATTTCAAACACTGCTGT

GGACCCTACTGGGTTTTTAAAATATTGTCAGTTTTTCATCGTGGTCCCTAGCCTGCCAACA

GCCATCTGCCCAGACAGCCGCAGTGAGGATGAGCGTCCTGGCAGAGACGCAGTTGTCTCTG

GGCGGTTGCCAGAGCCACGAACCGCAGACCTGTTTGTATCATGCGGGCTCCTTCCGSGCAG

AAACAACTGAAAATGCACTTCAGACCCACTTATTTCTGCCACATCTGAGTCGGCCTGAGAT

AGACTTTTCCCTCTAAACTGGGAGAATATCACAGTGGTTTTTGTTAGCACAAAATGCACTC

CAGCCTGTGTACTCATCTAAGGTGCTTATTTTTGATATTTGTGTCAGTCTGTAAATGGATA

CTTCACTTTAATAACTGTTGCTTAGTAATTGGCTTTGTAGAGAAGCTGGAAAAAAATGGTT

TTGTGTTCAACTCCTTTGCATGCCAGGCGGTGATGTGGATGTGGGCTTCTGTGAGCCTGTG

CTGTGGGCAGGGCTGAGCTGGAGGCGCCCCTCTCAGCCCGGCTGCCACGGCCTTTCCTTAA

AGGCCATCCTTAAAACCAGACCCTCATGGCTACCAGCACCTGAAAGCTTCCTCGACATCTG

TTAATAAAGCCGTAGGCCCTTGTCTAAGTGCAACCGCCTAGACTTTCTTTCAGATACATGT

CCACATGTCCATTTTTCAGGTTCTCTAAGTTGGAGTGGAGTCTGGGAAGGGTTGTGAATGA

GGCTTCTGGGCTATGGGTGAGGTTCCAATGGCAGGTTAGAGCGCCTCGGGCCAACTGCCAT

CCTGGAAAGTAGAGACAGCAGTGGCCGCTGCCCAGAAGAGACCAGCAAGCCAAACTGGAGC

CCCCGCATTGCAGGCTGTCGCCAGTGGAAAGAGTAACTCACAATTGCCAATAAAGTCTCAG

TGGTTTTATCTAAAAAAAAAAAAAAAAAAAAAAAA

Human BIRC5, Transcript Variant 3, mRNA (SEQ ID NO: 40)

(SEQ ID NO: 40)
CCCAGAAGGCCGCGGGGGGTGGACCGCCTAAGAGGGCGTGCGCTCCCGACATGCCCCGCGG

CGCGCCATTAACCGCCAGATTTGAATCGCGGGACCCGTTGGCAGAGGTGGCGGCGGCGGCA

TGGGTGCCCCGACGTTGCCCCCTGCCTGGCAGCCCTTTCTCAAGGACCACCGCATCTCTAC

ATTCAAGAACTGGCCCTTCTTGGAGGGCTGCGCCTGCACCCCGGAGCGGATGGCCGAGGCT

GGCTTCATCCACTGCCCCACTGAGAACGAGCCAGACTTGGCCCAGTGTTTCTTCTGCTTCA

AGGAGCTGGAAGGCTGGGAGCCAGATGACGACCCCATTGGGCCGGGCACGGTGGCTTACGC

CTGTAATACCAGCACTTTGGGAGGCCGAGGCGGGCGGATCACGAGAGAGGAACATAAAAAG

CATTCGTCCGGTTGCGCTTTCCTTTCTGTCAAGAAGCAGTTTGAAGAATTAACCCTTGGTG

AATTTTTGAAACTGGACAGAGAAAGAGCCAAGAACAAAATTGCAAAGGAAACCAACAATAA

GAAGAAAGAATTTGAGGAAACTCCGGAGAAAGTGCGCCGTGCCATCGAGCAGCTGGCTGCC

ATGGATTGAGGCCTCTGGCCGGAGCTGCCTGGTCCCAGAGTGGCTGCACCACTTCCAGGGT

TTATTCCCTGGTGCCACCAGCCTTCCTGTGGGCCCCTTAGCAATGTCTTAGGAAAGGAGAT

CAACATTTTCAAATTAGATGTTTCAACTGTGCTCTTGTTTTGTCTTGAAAGTGGCACCAGA

GGTGCTTCTGCCTGTGCAGCGGGTGCTGCTGGTAACAGTGGCTGCTTCTCTCTCTCTCT

CTTTTTTGGGGGCTCATTTTTGCTGTTTTGATTCCCGGGCTTACCAGGTGAGAAGTGAGGG

AGGAAGAAGGCAGTGTCCCTTTTGCTAGAGCTGACAGCTTTGTTCGCGTGGGCAGAGCCTT

CCACAGTGAATGTGTCTGGACCTCATGTTGTTGAGGCTGTCACAGTCCTGAGTGTGGACTT

GGCAGGTGCCTGTTGAATCTGAGCTGCAGGTTCCTTATCTGTCACACCTGTGCCTCCTCAG

AGGACAGTTTTTTGTTGTTGTGTTTTTTGTTTTTTTTTTTGGTAGATGCATGACTTG

TGTGTGATGAGAGAATGGAGACAGAGTCCCTGGCTCCTCTACTGTTTAACAACATGGCTTT

CTTATTTTGTTTGAATTGTTAQTTCACAGAATAGCACAAACTACAATTAAAACTAAGCACA

AAGCCATTCTAAGTCATTGGGGAAACGGGGTGAACTTCAGGTGGATGAGGAGACAGAATAG

-continued
```
AGTGATAGGAAGCGTCTGGCAGATACTCCTTTTGCCACTGCTGTGTGATTAGACAGGCCCA

GTGAGCCGCGGGGCACATGCTGGCCGCTCCTCCCTCAGAAAAAGGCAGTGGCCTAAATCCT

TTTTAAATGACTTGGCTCGATGCTGTGGGGGACTGGCTGGGCTGCTGCAGGCCGTGTGTCT

GTCAGCCCAACCTTCACATCTGTCACGTTCTCCACACGGGGGAGAGACGCAGTCCGCCCAG

GTCCCCGCTTTCTTTGGAGGCAGCAGCTCCCGCAGGGCTGAAGTCTGGCGTAAGATGATGG

ATTTGATTCGCCCTCCTCCCTGTCATAGAGCTGCAGGGTGGATTGTTACAGCTTCGCTGGA

AACCTCTGGAGGTCATCTCGGCTGTTCCTGAGAAATAAAAAGCCTGTCATTTCAAACACTG

CTGTGGACCCTACTGGGTTTTTAAAATATTGTCAGTTTTTCATCGTCGTCCCTAGCCTGCC

AACAGCCATCTGCCCAGACAGCCGCAGTGAGGATGAGCGTCCTGGCAGAGACGCAGTTGTC

TCTGGGCGCTTGCCAGAGCCACGAACCCCAGACCTGTTTGTATCATCCGGGCTCCTTCCGG

GCAGAAACAACTGAAAATGCACTTCAGACCCACTTATTTCTGCCACATCTGAGTCGGCCTG

AGATAGACTTTTCCCTCTAAACTGGGAGAATATCACAGTGGTTTTTGTTAGCAGAAAATGC

ACTCCAGCCTGTGTACTCATGTAAGCTGCTTATTTTTGATATTTGTGTCAGTGTGTAAATG

GATACTTCACTTTAATAACTGTTGCTTAGTAATTGGCTTTGTAGAGAAGCTGGAAAAAAAT

GGTTTTGTGTTCAACTGCTTTGCATGCCAGGCGGTGATGTGGATCTCGGCTTCTGTGAGCC

TGTGCTGTGGGCAGGGCTGAGCTGGAGCCGCCCCTCTCAGCCCGCCTGCCACGGCCTTTCC

TTAAAGGCCATGGTTAAAACCAGACCCTCATGGCTACCAGCACCTGAAAGCTTCCTCGACA

TGTGTTAATAAAGGCGTAGGCCCTTGTGTAAGTGGAACCGCCTAGACTTTGTTTCAGATAC

ATGTCCACATGTGCATTTTTCAGGTTCTCTAAGTTGGAGTGGAGTCTGGGAAGGGTTGTGA

ATGAGGCTTCTGGGCTATGGGTGAGGTTCCAATGGCAGGTTAGAGCCCCTCGGGCCAACTG

CCATCCTGGAAAGTAGAGACAGCAGTGCCCGCTGCCCAGAAGAGACCAGCAAGCCAAACTG

GAGCCCCCATTGCAGGCTGTCGCCATGTGGAAAGAGTAACTCACAATTGCCAATAAAGTCT

CATGTGGTTTTATCTAAAAAAAAAAAAAAAAAAAAAAAAAA
```

In some embodiments, the kits and/or methods of the disclosure are used to detect HOXC6 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of SEQ ID NO: 6 or SEQ ID NO: 41:

```
Human HOXC6, Transcript Variant 1, mRNA (SEQ ID NO: 6)

(SEQ ID NO: 6)
   1TTTTGTCTGTCCTGGATTGGAGCCGTCCCTATAACCATCTAGTTCCGAGTACAAACTGGA

GACAGAAATAAATATTAAAGAAATCATAGACCGACCAGGTAAAGGCAAAGGGATGAATTCC

TACTTCACTAACCCTTCCTTATCCTGCCACCTCGCCGGGGGCCAGGACGTCCTCCCCAACG

TCGCCCTCAATTCCACCGCCTATGATCCAGTGAGGCATTTCTCGACCTATGGAGCGGCCGT

TGCCCAGAACCGGATCTACTCGACTCCCTTTTATTCGCCACAGGAGAATGTCGTGTTCAGT

TCCAGCCGGGGCCGTATGACTATGGATCTAATTCCTTTTACCAGGAGAAAGACATGCTCT

CAAACTGCAGACAAAACACCTTAGGACATAACACACAGACCTCAATCGCTCAGGATTTTAG

TTCTGAGCAGGGCAGGACTGCGCCCCAGGACCAGAAAGCCAGTATCCAGATTTACCCCTGG

ATGCAGCGAATGAATTCGCACAGTGGGGTCGGCTACGGAGCGGACCGGAGGCGCGGCCGCC

AGATCTACTCGCGGTACCAGACCCTGGAACTGGAGAAGGAATTTCACTTCAATCGCTACCT

AACGCGGCGCCGGCGCATCGAGATCGCCAACGCGCTTTGCCTGACCGAGCGACAGATCAAA

ATCTGGTTCCAGAACCGCCGGATGAAGTGGAAAAAAGAATCTAATCTCACATCCACTCTCT
```

-continued

```
CGGGGGGCGGCGGAGGGGCCACCGCCGACAGCCTGGGCGGAAAAGAGGAAAAGCGGGAAGA
GACAGAAGAGGAGAAGCAGAAAGAGTGACCAGGACTGTCCCTGCCACCCCTCTCTCCCTTT
CTCCCTCGCTCCCCACCAACTCTCCCCTAATCACACACTCTGTATTTATCACTGGCACAAT
TGATGTGTTTTGATTCCCTAAAACAAAATTAGGGAGTCAAACGTGGACCTGAAAGTCAGCT
CTGGACCCCCTCCCTCACCGCACAACTCTCTTTCACCACGCGCCTCCTCCTCCTCGCTCCC
TTGCTAGCTCGTTCTCGGCTTGTCTACAGGCCCTTTTCCCCGTCCAGGCCTTGGGGGCTCG
GACCCTGAACTCAGACTCTACAGATTGCCCTCCAAGTGAGGACTTGGCTCCCCCACTCCTT
CGACGCCCCCACCCCCGCCCCCCGTGCAGAGAGCCGGCTCCTGGGCCTGCTGGGGCCTCTG
CTCCAGGGCCTCAGGGCCCGGCCTGGCAGCCGGGGAGGGCCGGAGGCCCAAGGAGGGCGCG
CCTTGGCCCCACACCAACCCCCAGGGCCTCCCCGCAGTCCCTGCCTAGCCCCTCTGCCCCA
GCAAATGCCCAGCCCAGGCAAATTGTATTTAAAGAATCCTGGGGGTCATTATGGCATTTTA
CAAACTGTGACCGTTTCTGTGTGAAGATTTTTAGCTGTATTTGTGGTCTCTGTATTTATAT
TTATGTTTAGCACCGTCAGTGTTCCTATCCAATTTCAAAAAAGGAAAAAAAAGAGGGAAAA
TTACAAAAAGAGAGAAAAAAAGTGAATGACGTTTGTTTAGCCAGTAGGAGAAAATAAATAA
ATAAATAAATCCCTTCGTGTTACCCTCCTGTATAAATCCAACCTCTGGGTCCGTTCTCGAA
TATTTAATAAAACTGATATTATTTTTAAAACTTTA
```

Human HOXC6, Transcript Variant 2, mRNA (SEQ ID NO: 41)

(SEQ ID NO: 41)
```
AACTTTTTATTGTGGTTTGTCCGTTCCGAGCGCTCCGCAGAACAGTCCTCCCTGTAAGAGC
CTAACCATTGCCAGGGAAACCTGCCCTGGGCGCTCCCTTCATTAGCAGTATTTTTTTTAAA
TTAATCTGATTAATAATTATTTTTCCCCCATTTAATTTTTTTTCCTCCCAGGTGGAGTTGC
CGAAGCTGGGGCAGCTGGGGAGGGTGGGGATGGGAGGGGAGAGACAGAAGTTGAGGGCAT
CTCTCTCTTCCTTCCCGACCCTCTGGCCCCCAAGGGGCAGGAGGAATGCAGGAGCAGGAGT
TGAGCTTGGGAGCTGCAGATGCCTCCGCCCCTCCTCTCTCCCAGGCTCTTCCTCCTGCCCC
CTTCTTGCAACTCTCCTTAATTTTGTTTGGCTTTTGGATGATTATAATTATTTTTATTTTT
GAATTTATATAAAGTATATGTGTGTGTGTGGAGCTGAGACAGGCTCGGCAGCGGCACAG
AATGAGGGAAGACGAGAAAGAGAGTGGGAGAGAGAGAGGCAGAGAGGGAGAGAGGGAGAGT
GACAGCAGCGCTCGGACGTCCTCCCCAACGTCGCCCTCAATTCCACCGCCTATGATCCAGT
GAGGCATTTCTCGACCTATGGAGCGGCCGTTGCCCAGAACCGGATCTACTCGACTCCCTTT
TATTCGCCACAGGAGAATGTCGTGTTCAGTTCCAGCCGGGGGCCGTATGACTATGGATCTA
ATTCCTTTTACCAGGAGAAAGACATGCTCTCAAACTGCAGACAAAACACCTTAGGACATAA
CACACAGACCTCAATCGCTCAGGATTTTAGTTCTGAGCAGGGCAGGACTGCGCCCCAGGAC
CAGAAAGCCAGTATCCAGATTTACCCCTGGATGCAGCGAATGAATTCGCACAGTGGGGTCG
GCTACGGAGCGGACCGGAGGCGCGGCCGCCAGATCTACTCGCGGTACCAGACCCTGGAACT
GGAGAAGGAATTTCACTTCAATCGCTACCTAACGCGGCGCCGGCGCATCGAGATCGCCAAC
GCGCTTTGCCTGACCGAGCGACAGATCAAAATCTGGTTCCAGAACCGCCGGATGAAGTGGA
AAAAGAATCTAATCTCACATGCACTCTCTCGGGGGCGGCGGAGGGGCCACCGCCGACAG
CCTGGGCGGAAAAGAGGAAAAGCGGGAAGAGACAGAAGAGGAGAAGGAGAAAGAGTGACCA
GGACTGTCCCTGCCACCCGTCTCTCCCTTTCTCCCTCGCTCCCCACCAACTCTCCCGTAAT
CACACACTGTGTATTTATCACTGGCACAATTGATGTGTTTTGATTCGCTAAAACAAAATTA
GGGAGTCAAACGTGGACCTGAAAGTCAGCTCTGGACCCCCTCCCTCACCGCACAACTCTCT
```

-continued

```
TTCACCACGCGCCTCCTCGTCCTCGCTCCCTTGCTAGCTCGTTCTCGGCTTGTCTACAGGC

CCTTTTCCCCGTCCAGGCGTTGGGGGCTCGGACCCTGAACTCAGACTCTACAGATTGCCCT

CCAAGTGAGGACTTGGCTCCCCCACTCCTTCGACGCCCCCACCCCCGCCCCCCGTGCAGAG

AGCCGGCTCCTGGGCCTGCTGGGGCCTCTGCTCCAGGGCCTCAGGGCCCGGCCTGGCAGCC

GGGGAGGGCCGGAGGCCCAAGGAGGGCGCGCCTTGGCCCCACACCAACCCCCAGGGCCTGC

CCGCAGTCCCTGCCTAGCCCCTCTGCCCCAGCAAATGCCCAGGCCAGGCAAATTGTATTTA

AAGAATGCTGGGGGTCATTATGGCATTTTACAAACTGTGACCGTTTCTGTGTGAAGATTTT

TAGCTGTATTTGTGGTCTCTGTATTTATATTTATGTTTAGGACCGTCAGTGTTCCTATCCA

ATTTCAAAAAAGGAAAAAAAAGAGGGAAAATTACAAAAAGAGAGAAAAAAAGTGAATGACG

TTTGTTTAGCCAGTAGGAaAAAATAAATAAATAAATAAATCCGTTCGTGTTACCCTCGTGT

ATAAATGCAACCTCTGGGTGCGTTCTCGAATATTTAATAAAACTGATATTATTTTTAAAAC

TTTAAAA
```

In some embodiments, the kits and/or methods of the disclosure are used to detect SPARCL1 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of SEQ ID NO: 7, SEQ ID NO: 42, SEQ ID NO: 43, or SEQ ID NO: 44:

```
Human SPARCL1, Transcript Variant 1, mRNA (SEQ ID NO: 7)

(SEQ ID NO: 7)
AAAAATGCATAAAGAGGCAAGTGGTTATATTGTGGCCAAGTTATGAGGCTGTGAGAACAAG

AGGTTGAGGGGAAGACTGTTAACCGCATGCACGGCACCAGAATTAGGTGTTTGCCTTTTGG

TTTGCAAGGACTGCGTGTAAAGGCCTGGGATGAGAGGCCAGGCTGCTAGGGAAATGCAGGA

ATGTGCAACAAAAACGATaACAGTGTGAAATACTCTGTGGTGCCAACCTGCAAATTGTGGT

CTGTCACTTCAGACCCCCACTAGTTGACAGAGCAGCAGAATTTCAACTCCAGTAGACTTGA

ATATGCCTCTGGGGAAAGAAGGAGAGGTAACGAGGAAAGGGATTTAAAGAGTTTTTGTTGG

GTGTTTGTCAAACTTTTATTCCCTGTCTGTGTGCAGAGGGGATTCAACTTCAATTTTTCTG

CAGTGGCTCTGGGTCCAGCCCCTTACTTAAAGGCCATAAGATGTTTTATTGAAAGAAACTT

TCAATATCAAGTAATCCAACCAACCTTCTAAGATAAGCCTTTTCCTTCAACACAAAGAAGT

GCATTTTGCCAAATCTGGAAAGCATGAAGACTGGGCTTTTTTTCCTATGTCTCTTGGGAAC

TGCAGCTGCAATCCCGACAAATGCAAGATTATTATCTGATCATTCCAAACCAACTGCTGAA

ACGGTAGCACCTGACAACACTGCAATCCCCAGTTTAAGGGCTGAAGCTGAAGAAAATGAAA

AAGAAACAGCAGTATCCACAGAAGACGATTCCCACCATAAGGCTGAAAAATCATCAGTACT

AAAGTCAAAAGAGGAAAGCCATGAACAGTCAGCAGAACAGGGCAAGAGTTCTAGCCAAGAG

CTGGGATTGAAGGATCAAGAGGACAGTGATGGTCACTTAAGTGTGAATTTGGAGTATGCAC

CAACTGAAGGTACATTGGACATAAAAGAAGATATGAGTGAGCCTCAGGAGAAAAAACTCTC

AGAGAACACTGATTTTTTGGCTCCTGGTGTTAGTTCCTTCACAGATTCTAACCAACAAGAA

AGTATCACAAAGAGAGAGGAAAACCAAGAACAACCTAGAAATTATTCACATCATCAGTTGA

ACAGGAGCAGTAAACATAGCCAAGGCCTAAGGGATCAAGGAAACCAAGAGCAGGATCCAAA

TATTTCCAATGGAGAAGAGGAAGAAGAAAAAGAGCCAGGTGAAGTTGGTACCCACAATGAT

AACCAAGAAAGAAAGACAGAATTGCCCAGGGAGCATGCTAACAGCAAGCAGGAGGAAGACA
```

-continued

```
ATACCCAATCTGATGATATTTTGGAAGAGTCTGATCAACCAACTCAAGTAAGCAAGATGCA

GGAGGATGAATTTGATCAGGGTAACCAAGAACAAGAAGATAACTCCAATGCAGAAATGGAA

GAGGAAAATGCATCGAACGTCAATAAGCACATTCAAGAAACTGAATGGCAGAGTCAAGAGG

GTAAAACTGGCCTAGAAGCTATCAGCAACCACAAAGAGACAGAAGAAAAGACTGTTTCTGA

GGCTCTGCTCATGGAACCTACTGATGATGGTAATACCACGCCCAGAAATCATGGAGTTGAT

GATGATGGCGATGATGATGGCGATGATGGCGGCACTGATGGCCCCAGGCACAGTGCAAGTG

ATGACTACTTCATCCCAAGCCAGGCCTTTCTGGAGGCCGAGAGAGCTCAATCCATTGCCTA

TCACCTCAAAATTGAGGAGCAAAGAGAAAAAGTACATGAAAATGAAAATATAGGTACCACT

GAGCCTGGAGAGCACCAAGAGGCCAAGAAAGCAGAGAACTCATCAAATGAGGAGGAAACGT

CAAGTGAAGGCAACATGAGGGTGCATGCTGTGGATTCTTGCATGAGCTTCCAGTGTAAAAG

AGGCCACATCTGTAAGGCAGACCAACAGGGAAAACCTCACTGTGTCTGCCAGGATCCAGTG

ACTTGTCCTCCAACAAAACCCCTTGATCAAGTTTGTGGCACTGACAATCAGACCTATGCTA

GTTCCTGTCATCTATTCGCTACTAAATGCAGACTGGAGGGGACCAAAAAGGGGCATCAACT

CCAGCTGGATTATTTTGGAGCCTGCAAATCTATTCCTACTTGTACGGACTTTGAAGTGATT

CAGTTTCCTCTACGGATGAGAGACTGGCTCAAGAATATCCTCATGCAGCTTTATGAAGCCA

ACTCTGAACACGCTGGTTATCTAAATGAGAAGCAGAGAAATAAAGTCAAGAAAATTTACCT

GGATGAAAAGAGGCTTTTGGCTGGGGACCATCCCATTGATCTTCTCTTAAGGGACTTTAAG

AAAAACTACCACATGTATGTGTATCCTGTGCACTGGCAGTTTAGTGAACTTGACCAACACC

CTATGGATAGAGTCTTGACACATTCTGAACTTGCTCCTCTGCGAGCATCTCTGGTGCCCAT

GGAACACTGCATAACCCGTTTCTTTGAGGAGTGTGACCCCAACAAGGATAAGCACATCACC

CTGAAGGAGTGGGGCCACTGCTTTGGAATTAAAGAAGAGGACATAGATGAAAATCTCTTGT

TTTGAACGAAGATTTTAAAGAACTCAACTTTCCAGCATCCTCCTCTGTTCTAACCACTTCA

GAAATATATGCAGCTGTGATACTTGTAGATTTATATTTAGCAAAATGTTAGCATGTATGAC

AAGACAATGAGAGTAATTGCTTGACAACAACCTATGCACCAGGTATTTAACATTAACTTTG

GAAACAAAAATGTACAATTAAGTAAAGTCAACATATGCAAAATACTGTACATTGTGAACAG

AAGTTTAATTCATAGTAATTTCACTCTCTGCATTGACTTATGAGATAATTAATGATTAAAC

TATTAATGATAAAAATAATGCATTTGTATTGTTCATAATATCATGTGCACTTCAAGAAAAT

GGAATGCTACTCTTTTGTGGTTTACGTGTATTATTTTCAATATCTTAATACCCTAATAAAG

AGTCCATAAAAATCCAAATGCTT
```

Human SPARCL1, Transcript Variant 2, mRNA (SEQ ID NO: 42)

```
                                                       (SEQ ID NO: 42)
AAAAATGCATAAAGAGCCAAGTGCTTATATTCTGGCCAAGTTATGAGGCTCTGAGAACAAG

AGCTTGAGGCGAAGACTGTTAACCCCATCCACGCCACCAGAATTAGCTCTTTCCCTTTTGG

TTTGCAAGCACTGCCTGTAAAGCCCTCGCATGAGAGGCCAGCCTGCTAGGGAAATCCAGGA

ATCTGCAACAAAAACGATGACAGTCTGAAATACTCTCTGGTGCCAACCTCCAAATTCTCGT

CTGTCACTTCAGACCCCCACTAGTTGACAGAGCAGGAGAATTTCAACTCCAGTAGACTTGA

ATATGCCTCTGGGCAAAGAAGGAGAGCTAACGAGGAAAGGGATTTAAAGAGTTTTTCTTGG

GTGTTTGTCAAACTTTTATTCCCTGTCTGTGTGCAGAGGGGATTCAACTTCAATTTTTCTG

CAGTGGCTCTGGGTCCAGCCCCTTACTTAAAGATCTGGAAAGCATGAAGACTGGGCTTTTT

TTCCTATGTCTCTTGGGAACTGCAGCTGCAATCCCGACAAATGCAAGATTATTATCTGATC

ATTCCAAACCAACTGCTGAAACGGTAGCACCTGACAACACTGCAATCCCCAGTTTAAGGGC
```

-continued

```
TGAAGCTGAAGAAAATaAAAAAGAAACAGCAGTATCCACAGAAGACGATTCCCACCATAAG
GCTGAAAAATCATCAGTACTAAAGTCAAAAGAGGAAAGCCATGAACAGTCAGGAGAACAGG
GCAAGAGTTCTAGCCAAGAGCTGGGATTGAAGGATCAAGAGGACAGTGATGGTCACTTAAG
TGTGAATTTGGAGTATGCACCAACTGAAGGTACATTGGACATAAAAGAAGATATGAGTGAG
CCTCAGGAGAAAAAACTCTCAGAGAACACTGATTTTTTGGCTCCTGGTGTTAGTTCCTTCA
CAGATTCTAACCAACAAGAAAGTATCACAAAGAGAGAGGAAAACCAAGAACAACCTAGAAA
TTATTCACATCATCAGTTGAACAGGAGCAGTAAACATAGCCAAGGCCTAAGGGATCAAGGA
AACCAAGAGCAGGATCCAAATATTTCCAATGGAGAAGAGGAAGAAGAAAAAGAGCCAGGTG
AAGTTGGTACCCACAATGATAACCAAGAAAGAAAGACAGAATTGCCCAGGGAGCATGCTAA
CAGCAAGCAGGAGGAAGACAATACCCAATCTGATGATATTTTGGAAGAGTCTGATCAACCA
ACTCAAGTAAGCAAGATGCAGGAGGATGAATTTGATCAGGGTAACCAAGAACAAGAAGATA
ACTCCAATGCAGAAATGGAAGAGGAAAATGCATCGAACGTCAATAAGCACATTCAAGAAAC
TGAATGGCAGAGTCAAGAGGGTAAAACTGGCCTAGAAGCTATCAGCAACCACAAAGAGACA
GAAGAAAAGACTGTTTCTGAGGCTCTGCTCATGGAACCTACTGATGATGGTAATACCACGC
CCAGAAATCATGGAGTTGATGATGATGGCGATGATGATGGCGATGATGGCGGCACTGATGG
CCCCAGGCACAGTGCAAGTGATGACTACTTCATCCCAAGCCAGGCCTTTCTGGAGGCCGAG
AGAGCTCAATCCATTGCCTATCACCTCAAAATTGAGGAGCAAAGAGAAAAAGTACATGAAA
ATGAAAATATAGGTACCACTGAGCCTGGAGAGCACCAAGAGGCCAAGAAAGCAGAGAACTC
ATCAAATGAGGAGGAAACGTCAAGTGAAGGCAACATGAGGGTGCATGCTGTGGATTCTTGC
ATGAGCTTCCAGTGTAAAAGAGGCCACATCTGTAAGGCAGACCAACAGGGAAAACCTCACT
GTGTCTGCCAGGATCCAGTGACTTGTCCTCCAACAAAACCCCTTGATCAAGTTTGTGGCAC
TGACAATCAGACCTATGCTAGTTCCTGTCATCTATTCGCTACTAAATGCAGACTGGAGGGG
ACCAAAAAGGGGCATCAACTCCAGCTGGATTATTTTGGAGCCTGCAAATCTATTCCTACTT
GTACGGACTTTGAAGTaATTCAGTTTCCTCTACGGATGAGAGACTGGCTCAAGAATATCCT
CATGCAGCTTTATGAAGCCAACTCTGAACACGCTGGTTATCTAAATGAGAAGCAGAaAAAT
AAAGTCAAGAAAATTTACCTGGATGAAAAGAGGCTTTTGGCTGGGGACCATCCCATTGATC
TTCTCTTAAGGGACTTTAAGAAAAACTACCACATGTATGTGTATCCTGTGCACTGGCAGTT
TAGTGAACTTGACCAACACCCTATGGATAGAGTCTTGACACATTCTGAACTTGCTCCTCTG
CGAGCATCTCTGGTGCCCATGGAACACTGCATAACCCGTTTCTTTGAGGAGTGTGACCCCA
ACAAGGATAAGCACATCACCCTGAAGGAGTGGGGCCACTGCTTTGGAATTAAAGAAGAGGA
CATAGATGAAAATCTCTTGTTTTGAACGAAGATTTTAAAGAACTCAACTTTCCAGCATCCT
CCTCTGTTCTAACCACTTCAGAAATATATGCAGCTGTGATACTTGTAGATTTATATTTAGC
AAAATGTTAGCATGTATGACAAGACAATGAGAGTAATTGCTTGACAACAACCTATGCACCA
GGTATTTAACATTAACTTTGGAAACAAAAATGTACAATTAAGTAAAGTCAACATATGCAAA
ATACTGTACATTGTGAACAGAAGTTTAATTCATAGTAATTTCACTCTCTGCATTGACTTAT
GAGATAATTAATGATTAAACTATTAATGATAAAAATAATGCATTTGTATTGTTCATAATAT
CAGTGCACTTCAAGAAAATGGAATGCTACTCTTTTGTGGTTTACGTGTATTATTTTCAAT
ATCTTAATACCCTAATAAAGM;TCCATAAAAATCCAAATGCTT
```

Human SPARCL1, Transcript Variant 3, mRNA (SEQ ID NO: 43)

(SEQ ID NO: 43)
AAAAATGCATAAAGAGCCAAGTGCTTATATTCTGGCCAAGTTATGAGGCTCTGAGAACAAG

AGCTTGAGGGGAAGACTGTTAACCCCATCCACGCCACCAGAATTAGCTCTTTCCCTTTTGG

TTTGCAAGCACTGCCTGTAAM;CCCTCGCATGAGAGGCCAGCCTGCTAGGGAAATCCAGGA

ATCTGCAACAAAAACGATGACAGTCTGAAATACTCTCTGGTGCCAACCTCCAAATTCTCGT

CTGTCACTTCAGACCCCCACTAGTTGACAGAGCAGCAGAATTTCAACTCCAGTAGACTTGA

ATATGCCTCTGGGCAAAGAAGCAGAGCTAACGAGGAAAGGGATTTAAAGAGTTTTTCTTGG

GTGTTTGTCAAACTTTTATTCCCTGTCTGTGTGCAGAGGGGATTCAACTTCAATTTTTCTG

CAGTGGCTCTGGGTCCAGCCCCTTACTTAAAGATCTGGAAAGCATGAAGACTGGGCTTTTT

TTCCTATGTCTCTTGGGAACTGCAGCTGCAATCCCGGTGAAAAGGAGATAAGAAGCAAAGG

AGCAAACCAAACCTAATATGAATCCTGTACTTTGGCCAGAAGCCGTGGCTCACATCTGTAA

TCCCAGCACTTTGGGAGGCCAAGACAAATGCAAGATTATTATCTGATCATTCCAAACCAAC

TGCTGAAACGGTAGCACCTGACAACACTGCAATCCCCAGTTTAAGGGCTGAAGCTGAAGAA

AATGAAAAGAAACAGCAGTATCCACAGAAGACGATTCCCACCATAAGGCTGAAAAATCAT

CAGTACTAAAGTCAAAAGAGGAAAGCCATGAACAGTCAGCAGAACAGGGCAAGAGTTCTAG

CCAAGAGCTGGGATTGAAGGATCAAGAGGACAGTGATGGTCACTTAAGTGTGAATTTGGAG

TATGCACCAACTGAAGGTACATTGGACATAAAAGAAGATATGAGTGAGCCTCAGGAGAAAA

AACTCTCAGAGAACACTGATTTTTTGGCTCCTGGTGTTAGTTCCTTCACAGATTCTAACCA

ACAAGAAAGTATCACAAAGAGAGAGGAAAACCAAGAACAACCTAGAAATTATTCACATCAT

CAGTTGAACAGGAGCAGTAAACATAGCCAAGGCCTAAGGGATCAAGGAAACCAAGAGCAGG

ATCCAAATATTTCCAATGGAGAAGAGGAAGAAGAAAAAGAGCCAGGTGAAGTTGGTACCCA

CAATGATAACCAAGAAAGAAAGACAGAATTGCCCAGGGAGCATGCTAACAGCAAGCAGGAG

GAAGACAATACCCAATCTGATGATATTTTGGAAGAGTCTGATCAACCAACTCAAGTAAGCA

AGATGCAGGAGGATGAATTTGATCAGGGTAACCAAGAACAAGAAGATAACTCCANTGCAGA

AATGGAAGAGGAAAATGCATCGAACGTCAATAAGCACATTCAAGAAACTGAATGGCAGAGT

CAAGAGGGTAAAACTGGCCTAGAAGCTATCAGCAACCACAAAGAGACAGAAGAAAAGACTC

TTTCTGAGGCTCTGCTCATGGAACCTACTGATGATGGTAATACCACGCCCAGAAATCATGG

AGTTGATGATGATGGCGATGATGATGGCGATGATGGCGGCACTGATGGCCCCAGGCACAGT

GCAAGTGATGACTACTTCATCCCAAGCCAGGCCTTTCTGGAGGCCCAGAGAGCTCAATCCA

TTGCCTATCACCTCAAAATTGAGGAGCAAAGAGAAAAAGTACATGAAAATGAAAATATAGG

TACCACTGAGCCTGGAGAGCACCAAGAGGCCAAGAAAGCAGAGAACTCATCAAATGAGGAG

GAAACGTCAAGTGAAGGCAACATGAGGGTGCATGCTGTGGATTCTTGCATGAGCTTCCAGT

GTAAAAGAGGCCACATCTGTAAGGCAGACCAACAGGGAAAACCTCACTGTGTCTGCCAGGA

TCCAGTGACTTGTCCTCCAACAAAACCCCTTGATCAAGTTTGTGGCACTGACAATCAGACC

TATGCTAGTTCCTGTCATCTATTCGCTACTAAATGCAGACTGGAGGGGACCAAAAAGGGGC

ATCAACTCCAGCTGGATTATTTTGGAGCCTGCAAATCTATTCCTACTTGTACGGACTTTGA

AGTGATTCAGTTTCCTCTACGGATGAGAGACTGGCTCAAGAATATCCTCATGCAGCTTTAT

GAAGCCAACTCTGAACACGCTGGTTATCTAAATGAGAAGCAGAGAAATAAAGTCAAGAAAA

TTTACCTGGATGAAAAGAGGCTTTTGGCTGGGGACCATCCCATTGATCTTCTCTTAAGGGA

CTTTAAGAAAAACTACCACATGTATGTGTATCCTGTGCACTGGCAGTTTAGTGAACTTGAC

-continued

```
CAACACCCTATGGATAGAGTCTTGACACATTCTGAACTTGCTCCTCTGCGAGCATCTCTGG

TGCCCATGGAACACTGCATAACCCGTTTCTTTGAGGAGTGTGACCCCAACAAGGATAAGCA

CATCACCCTGAAGGAGTGGGGCCACTGCTTTGGAATTAAAGAAGAGGACATAGATGAAAAT

CTCTTGTTTTGAACGAAGATTTTAAAGAACTCAACTTTCCAGCATCCTCCTCTGTTCTAAC

CACTTCAGAAATATATGCAGCTGTGATACTTGTAGATTTATATTTAGCAAAATGTTAGCAT

GTATGACAAGACAATGAGAGTAATTGCTTGACAACAACCTATGCACCAGGTATTTAACATT

AACTTTGGAAACAAAAATGTACAATTAAGTAAAGTCAACATATGCAAAATACTGTACATTG

TGAACAGAAGTTTAATTCATAGTAATTTCACTCTCTGCATTGACTTATGAGATAATTAATG

ATTAAACTATTAATGATAAAAATAATGCATTTGTATTGTTCATAATATCATGTGCACTTCA

AGAAAATGGAATGCTACTCTTTTGTGGTTTACGTGTATTATTTTCAATATCTTAATACCCT

AATAAAGAGTCCATAAAAATCCAAATGCTT
```

Human SPARCL1, Transcript Variant 4, mRNA (SEQ ID NO: 44)

(SEQ ID NO: 44)
```
AAAAATGCATAAAGAGCCAAGTGCTTATATTCTGGCCAAGTTATGAGGCTCTGAGAACAAG

AGCTTGAGGCGAAGACTGTTAACCCCATCCACGCCACCAGAATTAGCTCTTTCCCTTTTGG

TTTGCAAGCACTGCCTGTAAAGCCCTCGCATGAGAGGCCAGCCTGCTAGGGAAATCCAGGA

ATCTGCAACAAAAACGATGACAGTCTGAAATACTCTCTGGTGCCAACCTCCAAATTCTCGT

CTGTCACTTCAGACCCCCACTAGTTGACAGAGCAGCAGAATTTCAACTCCAGTAGACTTGA

ATATGCCTCTGGGCAAAGAAGGAGAGCTAACGAGGAAAGGGATTTAAAGAGTTTTTCTTGG

GTGTTTGTCAAACTTTTATTCCCTGTCTGTGTGCAGAGGGGATTCAACTTCAATTTTTCTG

CAGTGGCTCTGGGTCCAGCCCCTTACTTAAAGATCTGGAAAGCCATGAACAGTCAGCAGAA

CAGGGCAAGAGTTCTAGCCAAGAGCTGGGATTGAAGGATCAAGAGGACAGTGATGGTCACT

TAAGTGTGAATTTGGAGTATGCACCAACTGAAGGTACATTGGACATAAAAGAAGATATGAG

TGAGCCTCAGGAGAAAAAACTCTCAGAGAACACTGATTTTTTGGCTCCTGGTGTTAGTTCC

TTCACAGATTCTAACCAACAAGAAAGTATCACAAAGAGAGGAAAACCAAGAACAACCTA

GAAATTATTCACATCATCAGTTGAACAGGAGCAGTAAACATAGCCAAGGCCTAAGGGATCA

AGGAAACCAAGAGCAGGATCCAAATATTTCCAATGGAGAAGAGGAAGAAGAAAAAGAGCCA

GGTGAAGTTGGTACCCACAATGATAACCAAGAAAGAAAGACAGAATTGCCCAGGGAGCATG

CTAACAGCAAGCAGGAGGAAGACAATACCCAATCTGATGATATTTTGGAAGAGTCTGATCA

ACCAACTCAAGTAAGCAAGATGCAGGAGGATGAATTTGATCAGGGTAACCAAGAACAAGAA

GATAACTCCAATGCAGAAATGGAAGAGGAAATGCATCGAACGTCAATAAGCACATTCAAG

AAACTGAATGGCAGAGTCAAGAGGGTAAAACTGGCCTAGAAGCTATCAGCAACCACAAAGA

GACAGAAGAAAAGACTGTTTCTGAGGCTCTGCTCATGGAACCTACTGATGATGGTAATACC

ACGCCCAGAAATCATGGAGTTGATGATGATGGCGATGATGATGGCGATGATGGCGGCACTG

ATGGCCCCAGGCACAGTGCAM;TGATGACTACTTCATCCCAAGCCAGGCCTTTCTGGAGGC

CGAGAGAGCTCAATCCATTGCCTATCACCTCAAAATTGAGGAGCAAAGAGAAAAGTACAT

GAAAATGAAAATATAGGTACCACTGAGCCTGGAGAGCACCAAGAGGCCAAGAAAGCAGAGA

ACTCATCAAATGAGGAGGAAACGTCAAGTGAAGGCAACATGAGGGTGCATGCTGTGGATTC

TTGCATGAGCTTCCAGTGTAAAAGAGGCCACATCTGTAAGGCAGACCAACAGGGAAAACCT

CACTGTGTCTGCCAGGATCCAGTGACTTGTCCTCCAACAAAACCCCTTGATCAAGTTTGTG

GCACTGACAATCAGACCTATGCTAGTTCCTGTCATCTATTCGCTACTAAATGCAGACTGGA
```

-continued

```
GGGGACCAAAAAGGGGCATCAACTCCAGCTGGATTATTTTGGAGCCTGCAAATCTATTCCT

ACTTGTACGGACTTTGAAGTGATTCAGTTTCCTCTACGGATGAGAGACTGGCTCAAGAATA

TCCTCATGCAGCTTTATGAAGCCAACTCTGAACACGCTGGTTATCTAAATGAGAAGCAGAG

AAATAAAGTCAAGAAAATTTACCTGGATGAAAAGAGGCTTTTGGCTGGGGACCATCCCATT

GATCTTCTCTTAAGGGACTTTAAGAAAAACTACCACATGTATGTGTATCCTGTGCACTGGC

AGTTTAGTGAACTTGACCAACACCCTATGGATAGAGTCTTGACACATTCTGAACTTGCTCC

TCTGCGAGCATCTCTGGTGCCCATGGAACACTGCATAACCCGTTTCTTTGAGGAGTGTGAC

CCCAACAAGGATAAGCACATCACCCTGAAGGAGTGGGGCCACTGCTTTGGAATTAAAGAAG

AGGACATAGATGAAAATCTCTTGTTTTGAACGAAGATTTTAAAGAACTCAACTTTCCAGCA

TCCTCCTCTGTTCTAACCACTTCAGAAATATATGCAGCTGTGATACTTGTAGATTTATATT

TAGCAAAATGTTAGCATGTATGACAAGACAATGAGAGTAATTGCTTGACAACAACCTATGC

ACCAGGTATTTAACATTAACTTTGGAAACAAAAATGTACAATTAAGTAAAGTCAACATATG

CAAAATACTGTACATTGTGAACAGAAGTTTAATTCATAGTAATTTCACTCTCTGCATTGAC

TTATGAGATAATTAATGATTAAACTATTAATGATAAAAATAATGCATTTGTATTGTTCATA

ATATCATGTGCACTTCAAGAAAATGGAATGCTACTCTTTTGTGGTTTACGTGTATTATTTT

CAATATCTTAATACCCTAATAAAGAGTCCATAAAAATCCAAATGCTT
```

In some embodiments, the kits and/or methods of the disclosure are used to detect (i) ERG mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, and/or at least 250 nucleotides or more of the nucleic acid sequence of SEQ ID NO: 2, (ii) PCA3 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, and/or at least 450 nucleotides or more of the nucleic acid sequence of SEQ ID NO: 3, and (iii) at least a portion of at least one other mRNA selected from the group consisting of (1) AMACR mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of SEQ ID NO: 4, SEQ ID NO: 37, or SEQ ID NO: 38; (2) BIRC5 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of SEQ ID NO: 5, SEQ ID NO: 39, or SEQ ID NO: 40; (3) HOXC6 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of SEQ ID NO: 6 or SEQ ID NO: 41; and (4) SPARCL1 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of SEQ ID NO: 7, SEQ ID NO: 42, SEQ ID NO: 43, or SEQ ID NO: 44.

In some embodiments, the kits and/or methods of the disclosure are used to detect ERG mRNA having the full-length nucleic acid sequence of SEQ ID NO: 2, PCA3 mRNA having the full-length nucleic acid sequence of SEQ ID NO: 3, and at least one other mRNA selected from the group consisting of AMACR mRNA having the full-length nucleic acid sequence of SEQ ID NO: 4, SEQ ID NO: 37, or SEQ ID NO: 38, BIRC5 mRNA having the full-length nucleic acid sequence of SEQ ID NO: 5, SEQ ID NO: 39, or SEQ ID NO: 40, HOXC6 mRNA having the full-length nucleic acid sequence of SEQ ID NO: 6 or SEQ ID NO: 41, and SPARCL1 mRNA having the full-length nucleic acid sequence of SEQ ID NO: 7, SEQ ID NO: 42, SEQ ID NO: 43, or SEQ ID NO: 44.

The level of mRNA expression is detected using any of a variety of art-recognized techniques. For example, the Ct (cycle threshold) values for each biomarker in urine microvesicles are determined by RT-qPCR analysis. In a real time PCR assay a positive reaction is detected by accumulation of a fluorescent signal. The Ct value is defined as the number of cycles required for the fluorescent signal to cross the threshold (i.e., exceeds background level). Ct levels are inversely proportional to the amount of target nucleic acid in the sample (i.e., the lower the Ct level the greater the amount of target nucleic acid in the sample).

In some embodiments, the copy number of the detected genes (i.e., PCA3 and ERG) is calculated. Copy number can also be quantified using RT-qPCR analysis of one or more nucleic acids extracted from urine microvesicles. The skilled artisan can readily determine copy number using methods known in the art, such as by using a calibration curve.

To generate a calibration curve, a dilution series of known copy numbers of cDNA of a synthetic RNA sequence identical to the detected genes are analyzed on the same plate as the samples being analyzed for those same genes. By comparing the Ct values of samples to the Ct values of the calibration curve the exact copy number of sequences in the analyzed samples can be determined. By relating sample Ct values to calibration curves on the same plate the process "normalizes" for differences in performance of the assay due to variations in pipet inaccuracy, assay component performance (e.g., enzymes, probes, primers, dNTPs, etc.), qPCR thermocycler instrument performance (e.g., filters, temperature, etc.) and other plate-to-plate variation that might occur.

In the methods provided herein, those genes whose expression levels are used to calculate relative expression levels are referred to collectively as "reference genes." A reference gene used to determine the sufficiency of the urine sample for microvesicle-derived RNA are genes that are typically found in urine microvesicles, such as housekeeping genes or prostate-specific genes. The expression level of these reference genes are used to normalize for the amount of signal detected to control for variability in the quantity of microvesicles isolated between samples. For example, in the methods provided herein, the reference gene used for normalization of PCA3 and ERG expression can be KLK3, the gene encoding or prostate specific antigen (PSA), or SPDEF. The reference gene may be a prostate-specific gene. In some embodiments, the reference gene may be a non-tissue specific housekeeping gene, for example GAPDH. In the methods provided herein, the relative expression analysis, or normalization, is accomplished by subtracting the Ct value for the prostate-specific marker gene (e.g., KLK3) from the Ct values obtained for PCA3 and ERG with the result referred to as ΔCt. Copy numbers are calculated by fitting a curve of the following formula $$Ct = b + a * \log 10(\text{Calibration\_Copies})$$

to the known calibration points on the dilution series on the plate to achieve the "calibration curve". Copy numbers for samples are then calculated by the formula:

$$\text{Sample\_Copies} = 10\string^((Ct\_\text{Sample} - b)/a).$$

This copy number calculation is done independently for each marker gene (e.g. PCA3 and/or ERG) as well as for the reference gene (e.g. KLK3 or SPDEF). "Normalization" of the resulting signal from a marker gene (e.g. PCA3 and/or ERG) is then achieved by dividing the gene marker copy number by the reference gene copy number (e.g. ERG/SPDEF, ERG/KLK3, PCA3/SPDEF, and ERG/SPDEF).

In some embodiments, the kits and/or methods of the disclosure use a reference gene comprising a KLK3 mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, and/or at least 250 nucleotides or more of the following nucleic acid sequence:

```
                                           (SEQ ID NO: 8)
TTGTCTTCCTCACCCTGTCCGTGACGTGGATTGGTGCTGCACCCCTCATC

CTGTCTCGGATTGTGGGAGGCTGGGAGTGCGAGAAGCATTCCCAACCCTG

GCAGGTGCTTGTGGCCTCTCGTGGCAGGGCAGTCTGCGGCGGTGTTCTGG

TGCACCCCCAGTGGGTCCTCACAGCTGCCCACTGCATCAGGAACAAAAGC

GTGATCTTGCTGGGTCGGCACAGCCTGTTTCATCCTGAAGACACAGGCCA

GGTATTTCAGGTCAGCCACAGCTTCCCACACCCGCTCTACGATATGAGCC
```

In some embodiments, the kits and/or methods of the disclosure use a reference gene comprising a SPDEF mRNA having at least a portion, e.g., at least 10 nucleotides, at least 20 nucleotides, at least 30 nucleotides, at least 40 nucleotides, at least 50 nucleotides, at least 100 nucleotides, at least 150 nucleotides, at least 200 nucleotides, at least 250 nucleotides, at least 300 nucleotides, at least 350 nucleotides, at least 400 nucleotides, at least 450 nucleotides, and/or at least 500 nucleotides or more of the nucleic acid sequence of the following nucleic acid sequence:

```
                                           (SEQ ID NO: 9)
GGGAGACGAAUUGGGCCCUCUAGAUGCAUGCUCGAGCGGCCGCCAGUGUG

AUGGAUAUCUGCAGAAUUCGCCCUUAUUUAAGUAGUGACAUGUUUUUGCA

CAUUUCCAGCCCCUUUAAAUAUCCACACACACAGGAAGCACAAAAGGAAG

CACAGAGAUCCCUGGGAGAAAUGCCCGGCCCUGGGUGGGAUGUGCUGCA

CGCCCACCUGGACAUCUGGAAGUCAGCGGCCUGGAUGAAAGAGCGGACUU

CACCUGGGGCGAUUCACUACAAAUCUGGAAAGCAUGAAGACUGGGCUUUU

UUUCCUAUGUCUCUUGGGAACUGGAGCUGCAAUCCCGACAAAUGCAAGAU

UAUUAUCUGAUCAUUCCAAACCAACUGCUGAAACGGUAGCACCAGUUGCC

CAGAUAACUGUGACGAUGGACUAUGCACCAAUGGUUGCAAGUACGAAGAU

CUCUAUAGUAACUGUAAAAGUUUGAAGCUCACAUUAACCUGUAAACAUCA

GUUGGUCAGGGACAGUUGCAAAAGGACCACCGCAUCUCUACAUUCAAGAA

CUGGCCCUUCUUGGAGGGCUGCGCCUGCACCCCGGAGCGGAUGGCCGAGG

CUGGCUUCAUCCACUGCCCCACUGAGAACGAGCCAGACUUGACCUGCGGC

CGCAAGCUUGGAUCCGAAUUCCUGUGUGAAAUUGUUAUCCGCUCACAAUU

CCACACAACAUACGAGCCGGAAGCAUAAAGUGUAAAGCCUGGGGUGCCUA

AUGA
```

The relative, or normalized, expression levels of PCA3 and ERG and the reference gene can also be analyzed and compared using any of a variety of art-recognized techniques. For example, Receiver Operating Characteristics (ROC) analysis can be conducted for PCA3 and ERG, and optionally at least one other biomarker, wherein the expression levels of the biomarkers measured yield an Area Under the Curve (AUC) value for each biomarker measured. The ROC analyses of the biomarkers can be run individually, i.e., as individual biomarkers, or combined for linear regression analysis. Combinations of biomarkers with high diagnostic value as biomarkers as described herein with high diagnostic power have AUC values derived from ROC curves that are greater than 0.5, 0.6, 0.7, or 0.8. Preferably, the biomarker or combination of biomarkers have an AUC value greater than 0.7. For example, the combination of PCA3 and ERG yields an AUC value greater than 0.7.

The ROC curve is a widely used tool for evaluating discriminative and diagnostic power of a biomarker. When the biomarker value is missing for some observations, the ROC analysis based solely on complete cases loses efficiency because of the reduced sample size, and more importantly, it is subject to potential bias. Thus, imputation methods are implemented in the cases when a biomarker value is missing.

The Area Under the Curve (AUC) derived from the Receiver Operator Characteristic (ROC) curve for each level of biomarker or a score created by a combination of biomarkers is computed using biomarker results from both controls and patients with disease. One skilled in the art would readily be able to maximize diagnostic accuracy of the biomarker level or combination of biomarkers by a cut-off analysis that takes into account the sensitivity, specificity, negative predictive value (NPV), positive predictive value (PPV), positive likelihood ratio (PLR) and negative likelihood ratio (NLR) necessary for clinical utility.

The generation of ROC curves and analysis of a population of samples is used to establish the cutoff value used to distinguish between different subject sub-groups. For example, the cutoff value may distinguish between subjects with a high risk of recurrence of cancer from a low risk of recurrence of cancer. In some embodiments, the cutoff value may distinguish between subjects that have cancer from subjects that do not have cancer. In some embodiments, the cutoff value may distinguish between subjects with a non-aggressive cancer from an aggressive cancer. In some embodiments, the cutoff value may distinguish between subjects with a high Gleason score (e.g., GS>6) prostate cancer from a low Gleason score cancer.

As described herein, the normalized expression levels of PCA3 and ERG determined from a urine sample of a subject are computed into an output value for comparison with the cutoff value to distinguish between subject sub-groups. In some embodiments, the normalized expression levels of PCA3 and ERG are determined using KLK3 as the reference gene, as follows:

$$\Delta Ct_{ERG} = Ct_{ERG} - Ct_{KLK3}$$

$$\Delta Ct_{PCA3} = Ct_{PCA3} - Ct_{KLK3}$$

The ΔCt values for ERG and PCA3 are then applied into a mathematical formula to generate an output value. An example formula to generate the output value is as follows:

$$\text{Output Value} = (\Delta Ct_{ERG} \times 0.233) + (\Delta Ct_{PCA3} \times 0.446)$$

In the case of copy numbers, the Output Value of a test is calculated as follows:

$$\text{Output Value} = \text{Copy}_{PCA3}/\text{Copy}_{KLK3 \text{ or } SPDEF} \times \text{Coeff} + \text{Copy}_{ERG}/\text{Copy}_{KLK3 \text{ or } SPDEF} \times \text{Coeff},$$

where the coefficients can all be equal, e.g. 1 (one). In the case where the coefficients are equal, all genes have the same relative contribution to the output value. In some embodiments, the coefficients are different for each marker gene, which indicates that each marker gene has different contributions to the output value and thereby to the likelihood of a positive biopsy. In one approach, the coefficients can be defined by fitting the equation Output Value=$\text{Copy}_{PCA3}/\text{Copy}_{KLK3 \text{ or } SPDEF} \times \text{Coeff} + \text{Copy}_{ERG}/\text{Copy}_{KLK3 \text{ or } SPDEF} \times \text{Coeff}$ to an existing data set by linear regression.

As shown in the examples provided herein, the combination of PCA3 and ERG can specifically differentiate between biopsy negative and biopsy positive subjects with 77.8% sensitivity and 61.8% specificity. These values demonstrate the strength of the biomarker gene combinations disclosed herein as sensitive and specific diagnostic biomarkers for cancer, such as prostate cancer.

The term "subject" is intended to include all animals shown to or expected to have nucleic acid-containing microvesicles and/or circulating nucleic acids in urine. In particular embodiments, the subject is a mammal; for example, a human or nonhuman primate, a dog, a cat, a horse, a cow or another farm animal, or a rodent (e.g. a mouse, rat, guinea pig, etc.).

Procurement of a Microvesicle Fraction from a Urine Sample

Methods for procuring a microvesicle fraction from a urine sample are described in this application as well as in scientific publications and patent applications (Chen et al., 2010; Miranda et al., 2010; Skog et al., 2008). See also WO 2009/100029, WO 2011/009104, WO 2011/031892, and WO 2011/031877. These publications are incorporated herein by reference for their disclosures pertaining to microvesicle isolation or fraction procurement methods and techniques. These methods can include steps to evaluate the RNA integrity of an isolated microvesicle fraction, for example, by detecting the level of 18S and 28S RNA expression within the fraction.

For example, methods of microvesicle procurement by differential centrifugation are described in a paper by Raposo et al. (Raposo et al., 1996), a paper by Skog et al. (Skog et al., 2008) and a paper by Nilsson et al. (Nilsson et al., 2009). Methods of anion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS) is described in a paper by Taylor and Gercel-Taylor (Taylor and Gercel-Taylor, 2008). A method of nanomembrane ultrafiltration concentration is described in a paper by Cheruvanky et al. (Cheruvanky et al., 2007). Further, microvesicles can be identified and isolated from a subject's bodily fluid by a microchip technology that uses a microfluidic platform to separate tumor-derived microvesicles (Chen et al., 2010). Each of the foregoing references is incorporated by reference herein for its teaching of these methods.

In one embodiment of the methods described herein, the microvesicles isolated from urine are enriched for those originating from prostate or tumor cells. Because the microvesicles often carry surface molecules such as antigens from their donor cells, surface molecules may be used to identify, isolate and/or enrich for microvesicles from a specific donor cell type (Al-Nedawi et al., 2008; Taylor and Gercel-Taylor, 2008). In this way, microvesicles originating from distinct cell populations can be analyzed for their nucleic acid content. For example, tumor (malignant and non-malignant) microvesicles carry tumor-associated surface antigens and may be detected, isolated and/or enriched via these specific tumor-associated surface antigens. In one example, the surface antigen is epithelial-cell-adhesion-molecule (EpCAM), which is specific to microvesicles from carcinomas of lung, colorectal, breast, prostate, head and neck, and hepatic origin, but not of hematological cell origin (Balzar et al., 1999; Went et al., 2004).

Additionally, tumor specific microvesicles may be characterized by the lack of surface markers, such as CD80 and CD86. In these cases, microvesicles with the markers, such as CD80 and CD86, may be excluded for further analysis of tumor specific markers. The exclusion may be achieved by various methods, for example, affinity exclusion.

The procurement of microvesicle fractions from prostate can be accomplished, for example, by using antibodies, aptamers, aptamer analogs or molecularly imprinted polymers specific for a desired surface antigen. In some embodiments, the surface antigen is specific for a cancer type. In some embodiments, the surface antigen is specific for a cell type which is not necessarily cancerous.

One example of a method of microvesicle separation based on cell surface antigen is provided in U.S. Pat. No. 7,198,923. As described in, e.g., U.S. Pat. Nos. 5,840,867 and 5,582,981, WO/2003/050290 and a publication by Johnson et al. (Johnson et al., 2008), aptamers and their analogs specifically bind surface molecules and can be used as a separation tool for retrieving cell type-specific microvesicles. Molecularly imprinted polymers also specifically recognize surface molecules as described in, e.g., U.S. Pat. Nos. 6,525,154, 7,332,553 and 7,384,589 and a publication by Bossi et al. (Bossi et al., 2007) and are a tool for retrieving and isolating cell type-specific microvesicles. Each of the foregoing references is incorporated herein for its teaching of these methods.

In the methods described herein, a urine sample may be pre-processed by one or more filtration or centrifugation steps to remove cell debris and other non-microvesicle matter. For example, the urine sample may be filtered through a 0.8 um filter. Optionally, the filtrate acquired from the 0.8 um filter may be further filtered through a 0.22 um filter. To isolate the urine microvesicles, the pre-processed samples are then concentrated using a filtration concentration step. This step comprises utilizing a filter that has a molecular cutoff to retain and concentrate the microvesicles that are greater than 10 nm in diameter. For example, the sample is then concentrated to a volume of less than 1 mL, preferably 100-200 µL. For example, the molecular weight cutoff is at least 100 kDa. Preferably, the molecular weight cutoff is 100 kDa.

Nucleic Acid Extraction from Microvesicles

Methods for nucleic acid extraction are generally based on procedures well-known in the art. Persons of skill will select a particular extraction procedure as appropriate for the particular biological sample. Examples of extraction procedures are provided in patent publications WO 2009/100029, US 201/00196426, US 2011/0003704, US 2011/0053157, WO 2011/009104, and WO 2011/031892. These publications are incorporated herein by reference for their disclosure pertaining to microvesicle nucleic acid extraction methods and techniques.

In the methods described herein, an RNase inhibitor is added to the sample after microvesicle isolation and purification, but prior to microvesicle lysis and nucleic acid extraction for the purpose of preventing undesirable degradation of the nucleic acids after extraction. The microvesicles are lysed in the present of RNase inhibitor. The lysate is then added to an RNA-binding column, under such conditions known in the art so that the microvesicle RNA binds to the column. Optionally, the column is washed to increase the quality and yield of the RNA. Then the RNA is eluted under conditions known in the art such that high quality RNA is collected.

In some embodiments, the quality of the extracted nucleic acids can be assessed by detecting 18S and 28S ribosomal RNA and determining the ratio. The ratio of 18S:28S rRNA is preferably approximately 1:1 to approximately 1:2; more preferably approximately 1:2.

In some embodiments, nucleic acids may be extracted from the urine samples without isolation or purification of a microvesicle fraction.

Detection of Nucleic Acid Biomarkers

Biomarker detection can be carried out on the extracted nucleic acids in many different ways and constitute many aspects. In some embodiments, the detection of nucleic acid biomarkers from one or more urine samples is to obtain a profile of all or portions of the extracted nucleic acids.

A profile, as the term is used herein, refers to a representation of particular features of a collection of nucleic acids, which can be determined through quantitative or qualitative analysis of one or more nucleic acids contained in microvesicles or a microvesicle fraction isolated from a urine sample from a subject. A reference profile is here defined as a profile obtained from an independent subject or a group of subject, or from the same subject at a different time point.

The nucleic acids in microvesicles can be one or more types of nucleic acids, examples of which are provided herein.

The nucleic acids can be RNA. RNA can be coding RNA, e.g., messenger RNA which may encode proteins. RNA can also be non-coding RNA (ncRNA), e.g., ribosomal RNA, transfer RNA, microRNA, and other non-coding transcripts that may originate from genomic DNA. These non-coding RNA transcripts may include transcripts that are transcribed from satellite repeats; and transposons which may be DNA transposons or retrotransposons. Preferably, the nucleic acids are mRNAs.

The nucleic acids can be DNA. DNA can be single-stranded DNA that is reverse transcribed from RNA, e.g., cDNA. Reverse transcription is usually mediated by reverse transcriptase encoded by a reverse transcriptase gene in a cell. The DNA can also be single stranded DNA that is generated during DNA replication. Genomic DNA replicates in the nucleus while the cell is dividing. Some of the replicated DNA may come off its template, be exported out of the nucleus, and packaged in microvesicles. The DNA can further be fragments of double-stranded DNA.

In addition, the DNA can be non-coding DNA (ncDNA). The human genome only contains about 20,000 protein coding genes, representing less than 2% of the genome. The ratio of non-coding to protein-coding DNA sequences increases as a function of developmental complexity (Mattick, 2004). Prokaryotes have less than 25% ncDNA, simple eukaryotes have between 25-50%, more complex multicellular organisms like plants and animals have more than 50% ncDNA, with humans having about 98.5% ncDNA (Mattick, 2004)

Some of the ncDNA from the genome are transcribed into ncRNAs. NcRNAs have been implicated in many important processes in the cell, e.g., enzymes (ribozymes), binding specifically to proteins (aptamers), and regulating gene activity at both the transcriptional and post-transcriptional levels.

A profile of nucleic acids can be obtained through analyzing nucleic acids obtained from isolated microvesicles according to standard protocols in the art. For example, the analysis of the DNA may be performed by one or more various methods known in the art, including microarray analysis for determining the nucleic acid species in the extract, quantitative PCR for measuring the expression levels of genes, DNA sequencing for detecting mutations in genes, and bisulfite methylation assays for detecting methylation pattern of genes.

To obtain profiles, in some instances, data analysis may be performed. Such data analysis can be performed, for example, by Clustering Analysis, Principle Component Analysis, Linear Discriminant Analysis, Receiver Operating Characteristic Curve Analysis, Binary Analysis, Cox Proportional Hazards Analysis, Support Vector Machines and Recursive Feature Elimination (SVM-RFE), Classification to Nearest Centroid, Evidence-based Analysis, or a combination of any of the foregoing analytical techniques.

For another example, the analysis of RNA may be carried out using the Digital Gene Expression (DGE) analysis method (Lipson et al., 2009). For yet another example of RNA analysis, the RNA may be digested and converted into single stranded cDNA which may then be subject to sequencing analysis on a DNA sequencing machine, e.g., the HeliScope™ Single Molecule Sequencer from Helicos BioSciences as described in a publication by Ting et al. (Ting et al., 2011).

In other instances, the RNA may be reverse-transcribed into complementary DNA (cDNA) before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. Another example of the method comprises two separate steps: a first step of reverse transcription to convert RNA into cDNA and a second step of quantifying the amount of cDNA using quantitative PCR.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), BEAMing (Li et al., 2006) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods.

In some embodiments, the step of nucleic acid amplification is not performed. The unamplified nucleic acids can be analyzed by quantitative PCR (RT-PCR) or analyzed directly, e.g., through next-generation sequencing or nanostring technology.

The analysis of nucleic acids present in the isolated microvesicles can be quantitative and/or qualitative. For quantitative analysis, expression levels, either relative or absolute, of specific nucleic acids of interest within the isolated microvesicles are measured with methods known in the art and described herein. For qualitative analysis, the species of nucleic acids of interest within the isolated microvesicles, whether wild type or variants, are identified with methods known in the art.

In some embodiments, the detection of nucleic acid biomarkers involves detection of the presence or absence of one or a collection of genetic aberrations. The term "genetic aberration" is used herein to refer to the nucleic acid amounts as well as nucleic acid variants within the nucleic acid-containing microvesicles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs) (e.g., polymorphisms in Alu elements), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

Genetic aberrations can be found in many types of nucleic acids. The determination of such genetic aberrations can be performed by a variety of techniques known to the skilled practitioner. For example, expression levels of nucleic acids, alternative splicing variants, chromosome rearrangement and gene copy numbers can be determined by microarray analysis (see, e.g., U.S. Pat. Nos. 6,913,879, 7,364,848, 7,378,245, 6,893,837 and 6,004,755) and quantitative PCR. Copy number changes may be detected, for example, with the Illumina Infinium II whole genome genotyping assay or Agilent Human Genome CGH Microarray (Steemers et al., 2006).

Nucleic acid modifications can be assayed by methods described in, e.g., U.S. Pat. No. 7,186,512 and patent publication WO/2003/023065. Methylation profiles may be determined, for example, by Illumina DNA Methylation OMA003 Cancer Panel.

SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGE) (Fischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya et al., 1995; Landegren et al., 1988; Nakazawa et al., 1994), flow-cytometric heteroduplex analysis (WO/2006/113590) and combinations/modifications thereof.

In some embodiments, the detection of mutations is carried out by using a restriction enzyme which only digests one variant of the biomarker but does not digest other variants of the biomarker. As is known in the art, restriction enzymes faithfully recognize particular stretches of polynucleotides and the change of one or more nucleotides within the stretch of polynucleotides will mostly likely make the polynucleotide unrecognizable and indigestible by the enzyme. As such, the detection of one variant of a biomarker may be aided by digesting away some or all of the other variants that can be recognized by the enzyme. The variant to be detected can be a wild-type variant or a mutant variant.

Gene expression levels may be determined by the serial analysis of gene expression (SAGE) technique (Velculescu et al., 1995), quantitative PCR, quantitative reverse transcription PCR, microarray analysis, and next generation DNA sequencing, as known in the art.

In general, the methods for analyzing genetic aberrations are reported in numerous publications, not limited to those cited herein, and are available to skilled practitioners. The appropriate method of analysis will depend upon the specific goals of the analysis, the condition history of the patient, and the specific cancer(s), diseases or other medical conditions to be detected, monitored or treated.

Biomarkers Associated with Diseases or Other Medical Conditions

Many biomarkers may be associated with the presence or absence of a disease or other medical condition in a subject. Therefore, detection of the presence or absence of such biomarkers in a nucleic acid extraction from isolated microvesicles, according to the methods disclosed herein, may aid diagnosis, prognosis, or monitoring the progress or reoccurrence of the disease or other medical condition in the subject.

ERG, as used herein, refers to a gene also known as v-ets erythroblastosis virus E26 oncogene homolog and any identified isoforms. For example, ERG isoforms include ERG1, ERG2, ERG3, ERG4, ERG5, ERG6, ERG7, ERG8, and ERG9. ERG can also refer to ERG Prostate Cancer-specific isoform 1 (EPC1) and ERG Prostate Cancer-specific isoform 2 (EPC2). ERG, or any one of the isoforms of ERG, can be used as a biomarker for prostate cancer.

PCA3, as used herein, also refers to the gene also known as DD3 and any identified isoforms, and is useful as a biomarker for prostate cancer.

Many biomarkers have also been found to influence therapy selection for a particular patient. The detection of the presence or absence of such biomarkers in a nucleic acid extraction from isolated microvesicles, according to the methods disclosed herein, may aid in therapy selection in a given patient.

Patient Sub-Groups

The present invention provides methods of detecting one or more biomarkers in urine samples from a subject to aid in diagnosis, prognosis, monitoring, or therapy selection for a disease such as, for example, cancer, particularly an aggressive cancer.

Selection of an individual from whom the microvesicles are isolated is performed by the skilled practitioner based upon analysis of one or more of a variety of factors. Such factors for consideration are whether the subject has a family history of a specific disease (e.g., a cancer), has a genetic predisposition for such a disease, has an increased risk for such a disease, has physical symptoms which indicate a predisposition, or environmental reasons. Environmental reasons include lifestyle, exposure to agents which cause or contribute to the disease such as in the air, land, water or diet. Other reasons to select an individual for performing the methods disclosed herein include previous history with the disease, being currently diagnosed with the disease prior to therapy or after therapy, being currently treated for the disease (undergoing therapy), or being in remission or recovery from the disease.

The cancer diagnosed, monitored or otherwise evaluated with methods in this invention, can be any kind of cancer or pre-cancerous condition. This includes, without limitation, epithelial cell cancers such as lung, ovarian, cervical, endometrial, breast, brain, colon and prostate cancers. Also included are gastrointestinal cancer, head and neck cancer, non-small cell lung cancer, cancer of the nervous system, retina cancer, skin cancer, liver cancer, pancreatic cancer, renal cancer, genital cancer and bladder cancer, melanoma, and leukemia. In addition, the methods and compositions of the present invention are equally applicable to detection, diagnosis and prognosis of non-malignant tumors in an individual (e.g., neurofibromas, meningiomas and schwannomas). The cancer can be any aggressive cancer. In some embodiments, the cancer is a urogenital cancer, such as prostate cancer, bladder cancer, renal cancer, and metastatic cancer that has spread to the urogenital tract.

The present invention provides biomarkers that are of significant diagnostic and prognostic value in different patient subgroups. The patients have cancer, for example, prostate cancer. In some embodiments, the one or more biomarkers are detected in patients that have undergone radical prostatectomy. In some embodiments, the one or more biomarkers are detected in patients that have been assigned a particular Gleason score. In some embodiments, the one or more biomarkers are detected in patients that express ERG, or patients in whom the cancer is determined to be driven by ERG expression. These patients are referred to herein as "ERG Expressers." The presence of ERG or ERG expression over a certain predetermined threshold determines cancers driven by ERG expression. In some embodiments, the one or more biomarkers are detected in patients that do not express ERG, or patients in whom the cancer is determined to not be driven by ERG expression. These patients are referred to herein as "ERG Non-expressers."

The Gleason Grading System is commonly used in the art as a parameter of prognosis, often used in combination with other prognostic factors or tests, for prostate cancer. Prostate biopsy samples are examined, for example, by microscope, and a Gleason score is determined by a pathologist, based on the architectural pattern of the prostate tumor. The Gleason score is based upon the degree of loss of the normal glandular tissue architecture (i.e. shape, size and differentiation of the glands). The sample is assigned a grade to the most common tumor pattern, and a second grade to the next most common tumor pattern. There may be a primary or most common pattern and then a secondary or second most common pattern which can be identified; alternatively, there may be only a single grade. Gleason patterns are associated with the following features:

Pattern 1—The cancerous prostate closely resembles normal prostate tissue. The glands are small, well-formed, and closely packed.

Pattern 2—The tissue still has well-formed glands, but they are larger and have more tissue between them.

Pattern 3—The tissue still has recognizable glands, but the cells are darker. At high magnification, some of these cells have left the glands and are beginning to invade the surrounding tissue.

Pattern 4—The tissue has few recognizable glands. Many cells are invading the surrounding tissue.

Pattern 5—The tissue does not have recognizable glands. There are often just sheets of cells throughout the surrounding tissue.

The two grades are added together to get a Gleason Score, also known as a Gleason sum. Scores from 2 to 4 are very low on the cancer aggression scale. Scores from 5 to 6 are mildly aggressive. A score of 7 indicates that the cancer is moderately aggressive. Scores from 8 to 10 indicate that the cancer is highly aggressive.

Other grading systems to stratify non-aggressive cancers from aggressive cancers for other cancers, such as bladder cancer or renal cancer are known in the art.

EXAMPLES

Example 1: Materials and Methods

Primer/Probe Sequences: The kits and methods for detecting urine biomarker cohorts use the following primer/probe sequences. The following abbreviations are used in Table 1 below: probes from Integrated DNA Technologies are designated as "IDT," 5'-FAM refers to a 5' reporter dye, "3IABkFQ" refers to a 3'-IowaBlack quencher and "ZEN" refers to an in-sequence-ZEN™ quencher from IDT.

TABLE 1

Primer/Probe Sequences

| Target | Designation | Sequence/Modifications |
|---|---|---|
| SPDEF | 0881_SPDEF_e3-4_fF_IDT | CCACCTGGACATCTGGAAG (SEQ ID NO: 10) |
| SPDEF | 0884_SPDEF_e3-4_r1_IDT | AATCGCCCCAGGTGAAGT (SEQ ID NO: 11) |
| SPDEF | 0883_SPDEF_E3-4_P_ZEN | /56-FAM/CGG CCT GGA/ZEN/TGA AAG AGC G/3IABkFQ/ (SEQ ID NO: 12) |
| ERG | 0498_ERG_ex11-12_IDT_f (ERG LDT F1) | GCGTCCTCAGTTAGATCCTTATCAG (SEQ ID NO: 13) |
| ERG | 0499_ERG_ex12-13_IDT_R (ERG LDT R1) | CTGGCCACTGCCTGGATT (SEQ ID NO: 14) |
| ERG | 0500_ERG_ex12_IDT_FAM_ZEN_probe | /56-FAM/CTT GGA CCA /ZEN/ACA AGT AGC CGC CTT GC/3IABkFQ/ (SEQ ID NO: 15) |
| PCA3 | 0539_PCA3_ex3-4_malig_IDT_f | GCA CAT TTC CAG CCC CTT TA (SEQ ID NO: 16) |
| PCA3 | 0540_PCA3_ex3-4_malig_IDT_r | GGC ATT TCT CCC AGG GAT CT (SEQ ID NO: 17) |
| PCA3 | 0514_PCA3_ex3-4_malig_IDT_FAM_ZEN_probe | /56-FAM/CAC ACA GGA /ZEN/AGC ACA AAA GGA AGC /3IABkFQ/ (SEQ ID NO: 18) |
| Qbeta | 0545_Qbeta_P3_IDT_f | AAC GGT TCT TGT GAC CCA TC (SEQ ID NO: 19) |
| Qbeta | 0546_Qbeta_P3_IDT_r | CGA ACA AAA GCT CGT TCC TC (SEQ ID NO: 20) |
| Qbeta | 0547_Qbeta_P3_Tm69_IDT_FAM_ZEN_probe | /56-FAM/CGC CAG GCA /ZEN/TAT GCT GAC GTG /3IABkFQ/ (SEQ ID NO: 21) |
| KLK3 | 0535_KLK3_LDT_ex1-2_P3_f(KLK3 LDT F1) | CCTGTCCGTGACGTGGAT (SEQ ID NO: 22) |
| KLK3 | 0536_KLK3_LDT_ex1-2_P3_r(KLK3 LDT R) | CAGGGTTGGGAATGCTTCT (SEQ ID NO: 23) |
| KLK3 | 0538_KLK3_ex1-2_P3_Tm70_FAM_ZEN_probe | /56-FAM/CGG ATT GTG /ZEN/GGA GGC TGG GA/3IABkFQ/(SEQ ID NO: 24) |
| TMPRSS:ERG | 0949_TMPRSS-ERG_CL_F | GCC TGGAGC GCG GCA G (SEQ ID NO: 25) |
| TMPRSS:ERG | 0951_TMPRSS-ERG_SL_R2 | GCA CAC TCA AAC AAC GAC TG (SEQ ID NO: 26) |
| TMPRSS:ERG | 0955_TMPRSS-ERG_SL_P1 | /56-FAM/AGC CTT ATC /ZEN/AGT TGT GAG TGA GGA C/3IABkFQ/(SEQ ID NO: 27) |
| AMACR | 0508_AMACR_ex1-2_LDT_f | GCCGCGGTGTCATGG (SEQ ID NO: 28) |
| AMACR | 0509_AMACR_ex2_LDT_f | TTTCCCGCTGCAGAATCTC (SEQ ID NO: 29) |
| AMACR | 0510_AMACR_353_IDT_FAM_ZEN_probe | /56-FAM/AGA AAC TCC /ZEN/AGC TGG GCC CA/3IABkFQ/ (SEQ ID NO: 30) |
| BIRC5 | 0582_BIRC5_P3_e1-2_F | GGA CCA CCG CAT CTC TAC AT (SEQ ID NO: 31) |
| BIRC5 | 0583_BIRC5_P3_e12_R | GTC TGG CTC GTT CTC AGT GG (SEQ ID NO: 32) |
| BIRC5 | 0584_BIRC5_P3_e1-2_IDT_FAM_ZEN_probe | /56-FAM/CTT CTT GGA /ZEN/GGG CTG CGC CT/3IABkFQ/ (SEQ ID NO: 33) |
| SPARCL1 | 0585_SPARCL1_P3-2_f | TCT GGA AAG CAT GAA GAC TGG (SEQ ID NO: 34) |

TABLE 1-continued

Primer/Probe Sequences

| Target | Designation | Sequence/Modifications |
|---|---|---|
| SPARCL1 | 0586_SPARCL1_P3-2_R | TGC TAC CGT TTC AGC AGT TG (SEQ ID NO: 35) |
| SPARCL1 | 0587_SPARCL1_P3-2_IDT_FAM_ZEN_probe | /56-FAM/CTG CAG CTG /ZEN/CAA TCC CGA CA/3IABkFQ/ (SEQ ID NO: 36) |

Example 2: Patient Cohort 7 Sample Preparation

A cohort of patient samples was used to identify biomarkers useful for detecting prostate cancer from nucleic acids extracted from the urine-derived microvesicles. A patient cohort of 258 subjects, referred to as "cohort 7" in this example, were enrolled in this study. Of the 258 subjects, 196 had their first biopsy, and 59 had repeat biopsies. Of the primary biopsy patients, 87 had positive biopsy results, and 109 had negative biopsy results. Of the repeat biopsy patients, 15 had positive biopsy results, and 44 had negative biopsy results.

Urine sample volumes ranged from 20-100 mL. The distribution of the initial volume of urine samples from the patients were as follows: sample volume (V) is equal to 20 mL (i.e., V=20 mL), 21% of the patients (n=55); sample volumes is greater than 20 mL but less than or equal to 40 mL (i.e., 20 mL<V≤0.40 mL), 27% of the patients (n=70); or sample volumes is greater than 40 mL (i.e., V>40 mL), 52% of the patients (n=133).

Urine samples from cohort 7 were analyzed as depicted in FIGS. 1A and 1B. For example, urine samples were collected and filtered through a 0.8 µm filter to separate cells and other cell debris from the microvesicles, and the microvesicle-enriched fractions were frozen at −80° C. A first aliquot from each sample (S1) was further processed. Additional processing steps may include centrifugation, concentration through a filtration concentrator, 1-2 washing steps, and/or addition of RNase inhibitor. Optionally, control particles, such as Q-beta particles, can be added to the samples prior to microvesicle isolation or nucleic acid extraction to determine the quality of the isolation or nucleic acid extraction. For example, 18 subjects were removed from the study due to Q-beta control failures.

Specifically, the urine sample is first filtered, and the filtrate is discarded. Q-beta control is added at the appropriate concentration (e.g., 100 copies) to an aliquot of the filtered urine samples (e.g., 15 mL). The aliquot is then processed through a filter concentrator, and the filtrate is discarded. The retentate is re-suspended with a second aliquot of filtered urine samples (e.g., 5 mL of filtered urine) and processed through a filter concentrator. The retentate is then washed at least once (e.g. twice), and re-spun in the filter concentrator. RNase inhibitor is added to the retentate located in the upper chamber of the filter concentrator, and incubated at room temperature, for example, for 2-3 minutes. Lysis buffer is then added to the sample directly and incubated for 1 minute. The lysate is then transferred to another container to continue with nucleic acid extraction.

The samples are then subjected to nucleic acid extraction using methods well known in the art and conditions suitable to yield high quality RNA. 12 µl of the extracted RNA is analyzed by BioAnalyzer Profile. The extracted RNA is reverse transcribed into cDNA (SUPERSCRIPT® VILO cDNA Synthesis Kit. Life Technologies). Quantitative real-time PCR was performed on the cDNA samples to determine the gene expression of PCA3, ERG, KLK3, and Qbeta (2 µl per gene). A calibration standard curve was present on each qPCR plate.

Primer and probe sequences can be found in Table 1.

Example 3: PCA3 and ERG Gene Expression Analysis

Figure 3A:
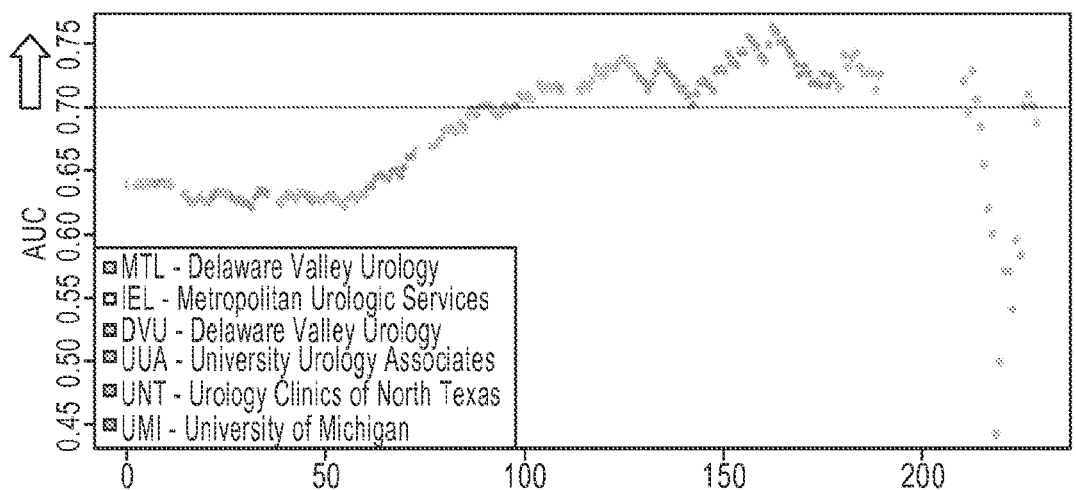
FIGS. 3A and 3B are two graphs depicting the correlation of PCA3 AUC values when normalized to KLK3 to the sample volume for each patient in Cohort 7.
Figure 3B:
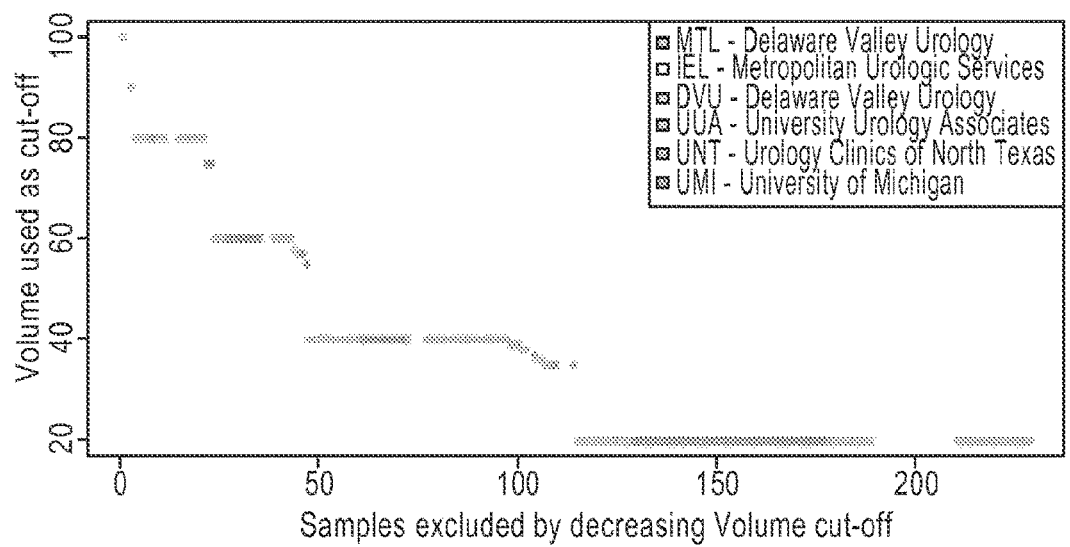
Figure 4A:
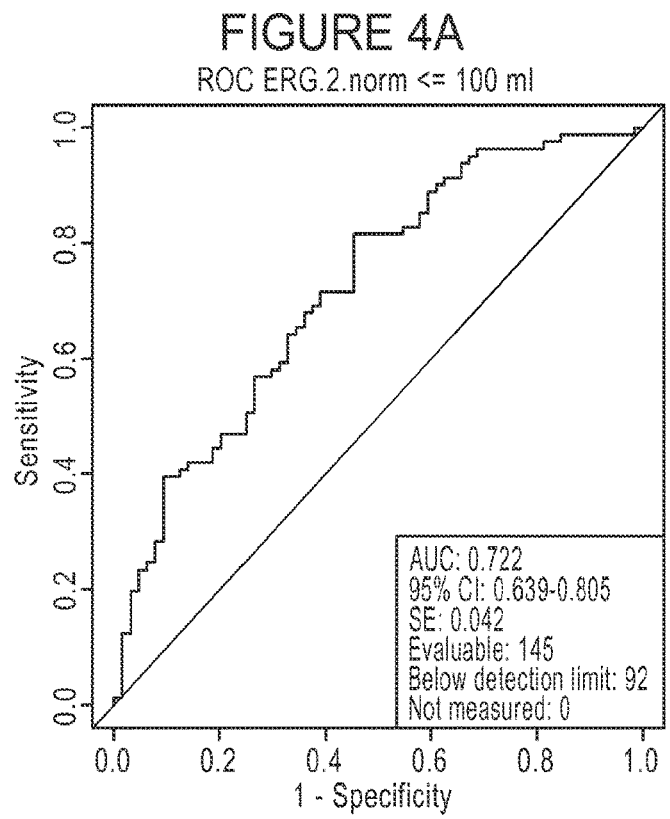
FIGS. 4A and 4B are two graphs depicting ROC curves based on ERG expression analysis normalized to KLK3 (non-imputed, FIG. 4A) and PCA3 (FIG. 4B) expression analysis normalized to KLK3 with samples from Patient Cohort 7 in which the sample volume was less than or equal to 100 mL (N=236). In both figures, the X axis represents specificity; the Y axis represents sensitivity.
Figure 4B:
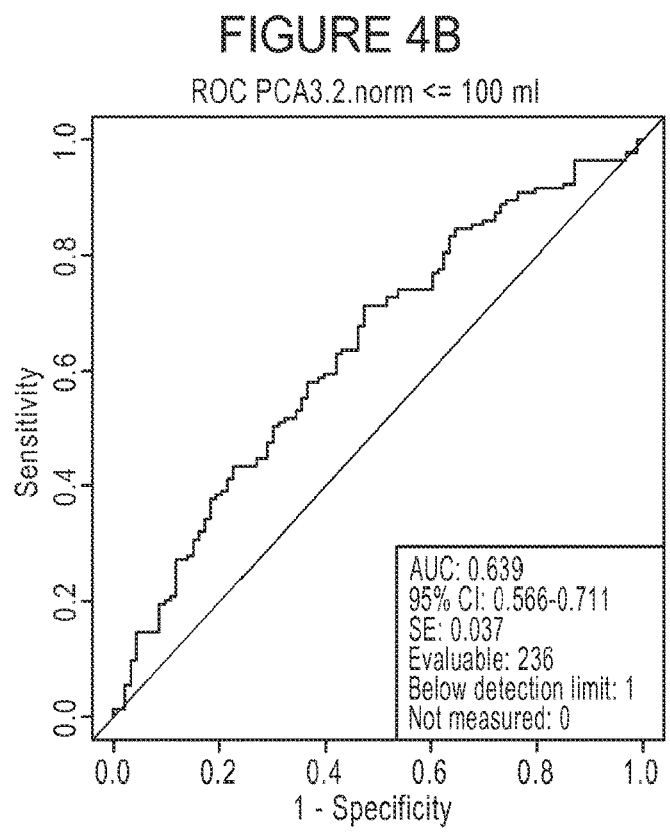
Figure 5A:
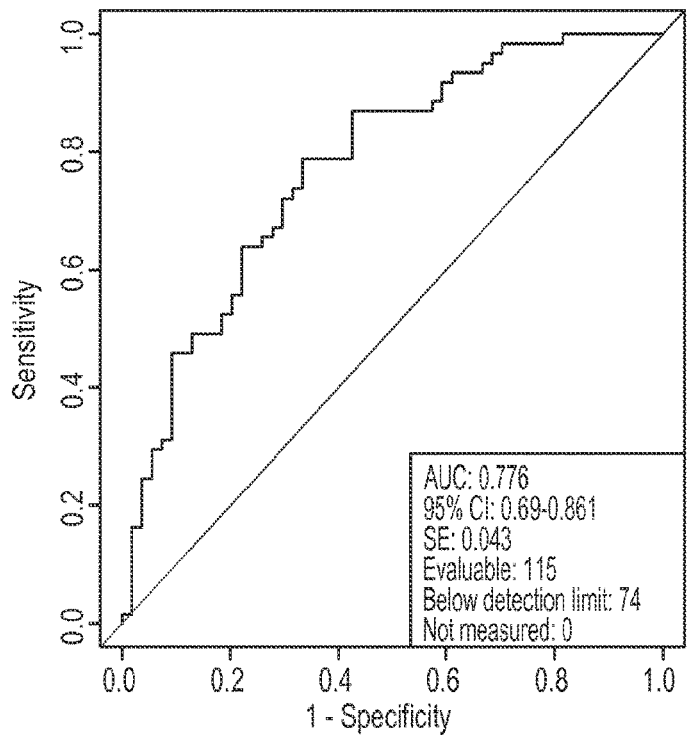
FIGS. 5A and 5B are two graphs depicting ROC curves based on ERG expression analysis normalized to KLK3 (non-imputed, FIG. 5A) and PCA3 (FIG. 5B) expression analysis normalized to KLK3 with samples from Patient Cohort 7 in which the sample volume was less than or equal to 40 mL (N=189). In both figures, the X axis represents specificity; the Y axis represents sensitivity.
Figure 5B:
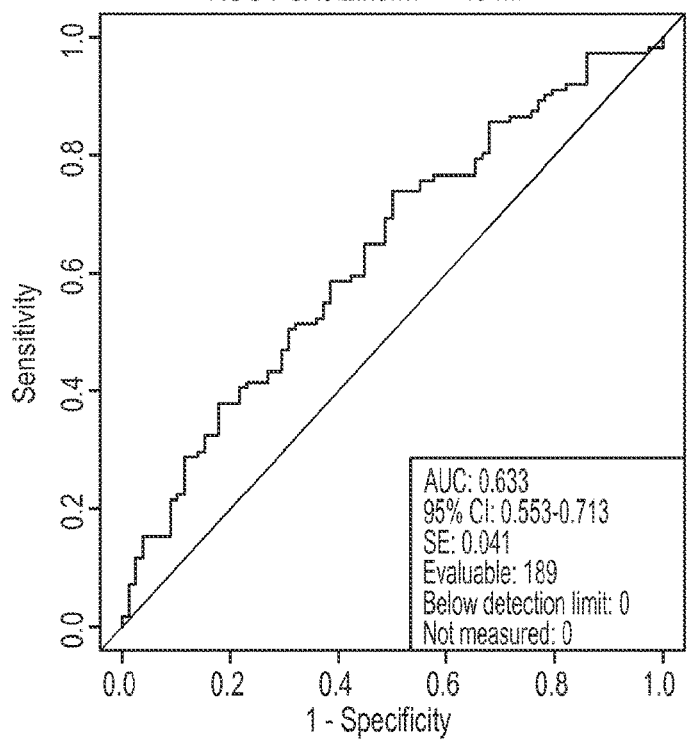
Figure 6A:
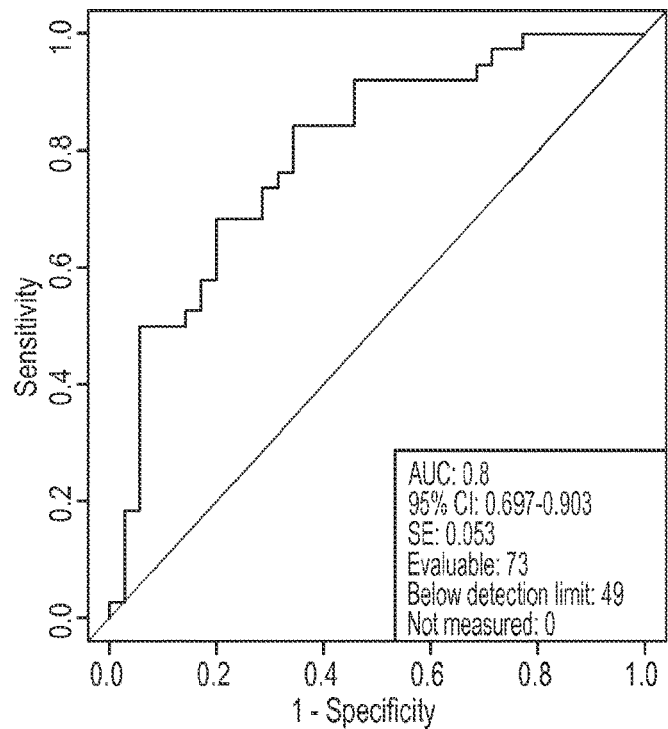
FIGS. 6A and 6B are two graphs depicting ROC curves based on ERG expression analysis normalized to KLK3 (non-imputed, FIG. 6A) and PCA3 (FIG. 6B) expression analysis normalized to KLK3 with samples from Patient Cohort 7 in which the sample volume was less than or equal to 20 mL (N=122). In both figures, the X axis represents specificity; the Y axis represents sensitivity.
Figure 6B:
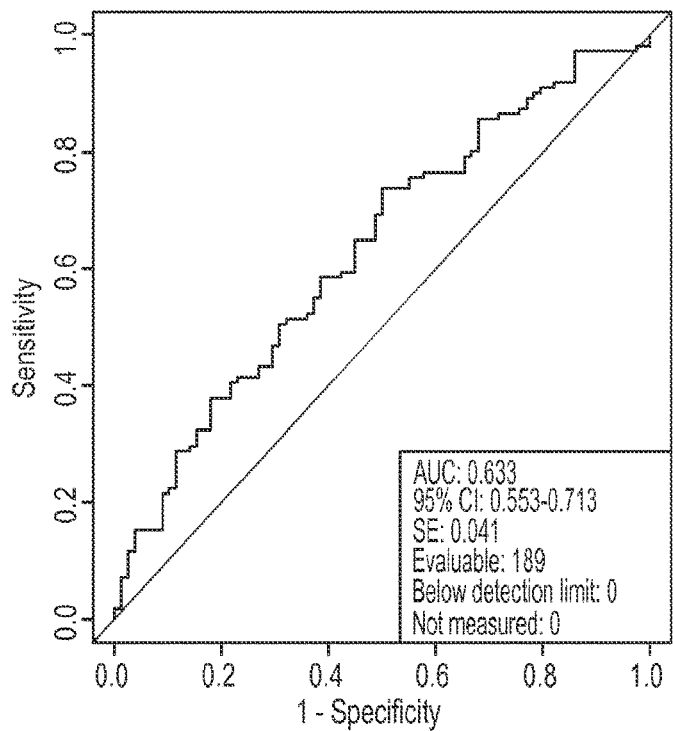
Figure 7:
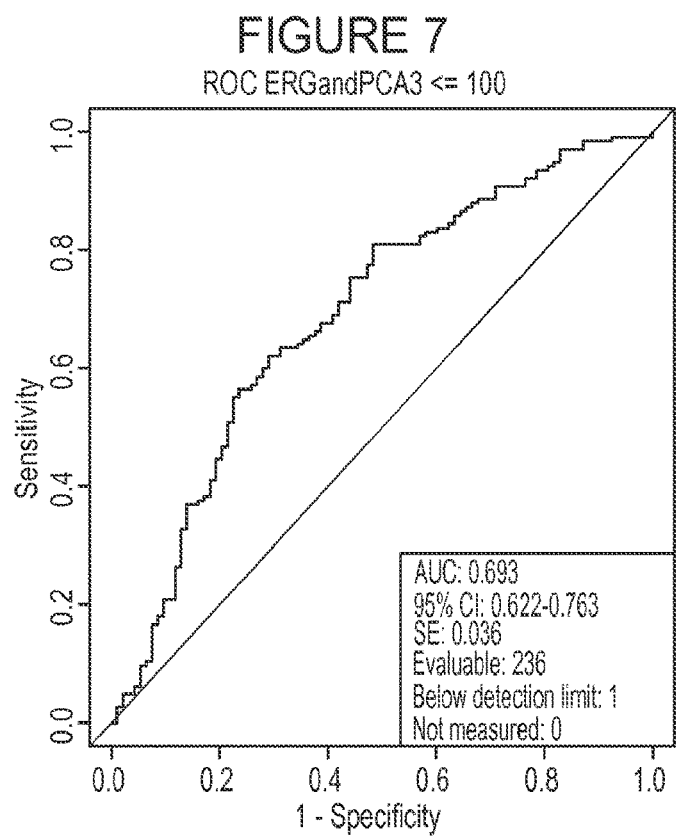
FIG. 7 is a graph depicting ROC curves based on ERG and PCA3 expression analysis normalized to KLK3 with samples from Patient Cohort 7 in which the sample volume was less than or equal to 100 mL (N=236). ERG expression analysis was imputed. The X axis represents specificity; the Y axis represents sensitivity.
Figure 8:
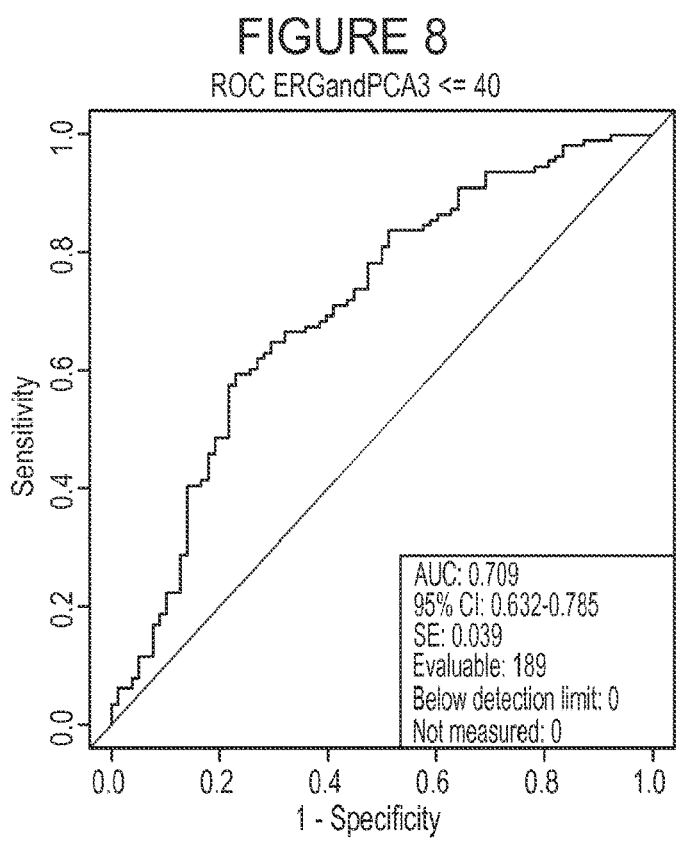
FIG. 8 is a graph depicting ROC curves based on ERG and PCA3 expression analysis normalized to KLK3 with samples from Patient Cohort 7 in which the sample volume was less than or equal to 40 mL (N=189). ERG expression analysis was imputed. The X axis represents specificity; the Y axis represents sensitivity.
Figure 11:
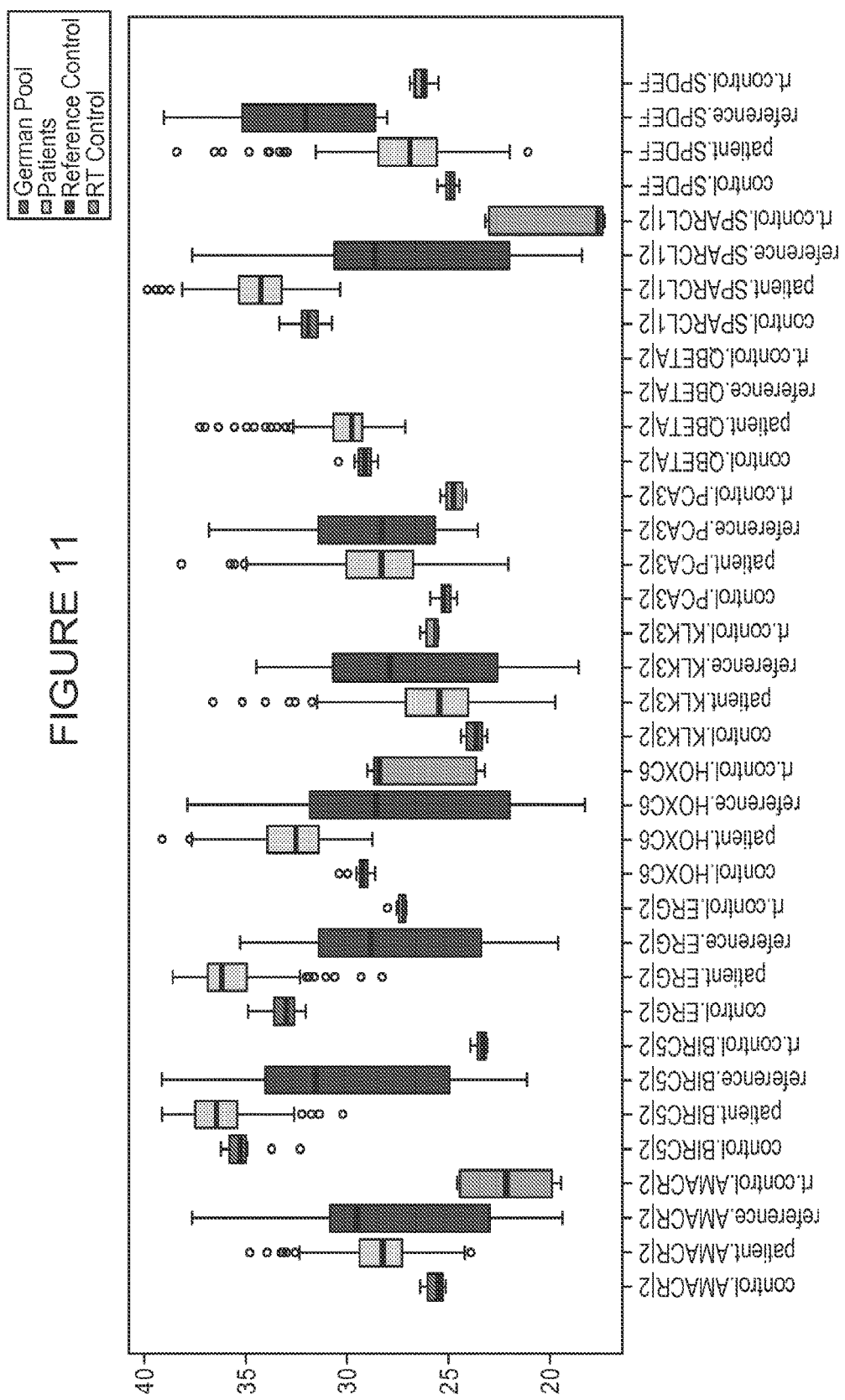
FIG. 11 is a box plot showing the distribution of Ct values for the detected genes (AMACR, BIRC5, ERG, HOXC6, KLK3, PCA4, QBETA, SPARCL1, and SPDEF) in each sample group (German pool=control pool samples. Patients=Cohort 7 patients, Reference=reference controls, and RT-controls=reverse transcriptase controls).

Multiple analyses were performed using the gene expression results from of qPCR experiment. ROC curves were generated based on the delta Ct or copy number relative to the normalizer gene KLK3. Imputation may be used to obtain missing values. ROC analysis of PCA3, using KLK3 as the normalizer gene, generated an AUC value of 0.727 (FIG. 3). ROC curve analysis of PCA3 and ERG produced an increased AUC value of 0.756 (FIG. 4). In other experiments, the normalizer gene utilized was SPDEF (FIG. 13) and AUC values generated from analysis using SPDEF normalization showed that KLK3 and SPDEF performed equivalently.

Model, or output, values for PCA3 and ERG gene expression were also calculated for each sample using the following formula, which was determined from data analysis of a different patient cohort (Cohort 5):

$$\text{Model Value} = (\Delta Ct_{ERG} \times 0.233) + (\Delta Ct_{PCA3} \times 0.446)$$

where $\Delta Ct_{ERG} = Ct_{ERG} - Ct_{KLK3}$; $\Delta Ct_{PCA3} = Ct_{PCA3} - Ct_{KLK3}$ A model cutoff value was chosen, for example, the cutoff value used in this example was 4.7, and the diagnostic accuracy of using the combination of PCA3 and ERG with a cutoff model value of 4.7 was determined by 2×2 analysis and Gleason analysis (FIG. 10).

Results of the 2×2 analysis using PCA3 and ERG gene expression for each sample volume sub-group of cohort 7 is summarized in Tables 2a, 3a and 4a. The combination of PCA3 and ERG greater than 84% sensitivity for identifying prostate cancer in samples that had been identified as positive by biopsy. In particular, the data demonstrated that urine sample volumes of 20 mL yielded better diagnostic accuracy, with sensitivity at 83.6% and specificity at 58.7%. This method also had a high negative predictive value of 79.4%, and a positive predictive value of 53.4%.

Further analysis included stratification of the samples by their Gleason scores, as shown in Tables 2b, 3b and 4b, and quartile analysis, as shown in Tables 2d, 2e, 3d, 3e, 4d, and 4c. Specifically, samples of patients with Gleason scores of 6 or higher were correctly identified 70% of the samples.

Example 4: Three-Gene Models Including PCA3

Figure 15:
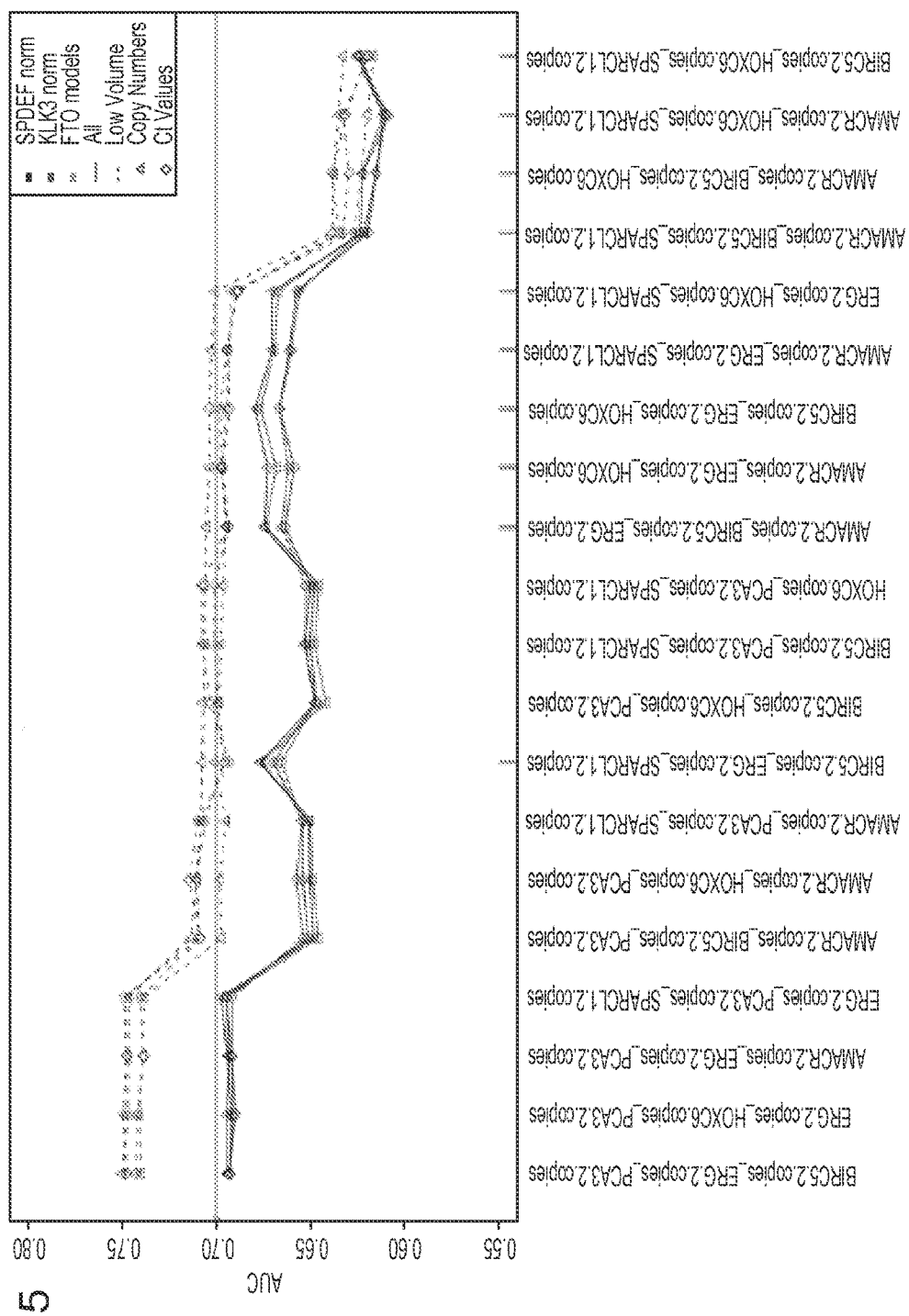
FIG. 15 is a graph showing the AUC values generated by 3-gene model analysis of the indicated combination of the following genes: AMACR, BIRC5, ERG, HOXC6, KLK3, PCA3, SPARCL1, and SPDEF; and comparing the AUC values between the following subsets: normalized to SPDEF or KLK3; imputed and normalized to SPDEF or KLK3; all sample volumes to low volume samples; and copy numbers to Ct values.

Multivariate analysis was performed using gene sets including PCA3. As shown in FIG. 15, PCA3-containing models (i.e., PCA3 and ERG with an additional gene, such as AMACR, BIRC5, HOXC6 and SPARCL1) consistently outperformed FTO three-gene models that did not contain PCA3. The reference genes used can be KLK3 or SPDEF, as shown by the consistent AUC values using either gene for normalization in FIG. 15.

The three-gene models were also shown to have improved AUC values when using low volume samples (i.e., 20 mL) compared to all samples (FIG. 15).

Example 5: Optimal Urine Sample Volume

Urine samples from Patient Cohort 7 ranged from 20-100 mL. The distribution of samples with volumes at 20 mL or less, 40 mL or less but greater than 20 mL, and more than 40 mL in cohort 7 is shown in FIG. 1.

Figure 12:
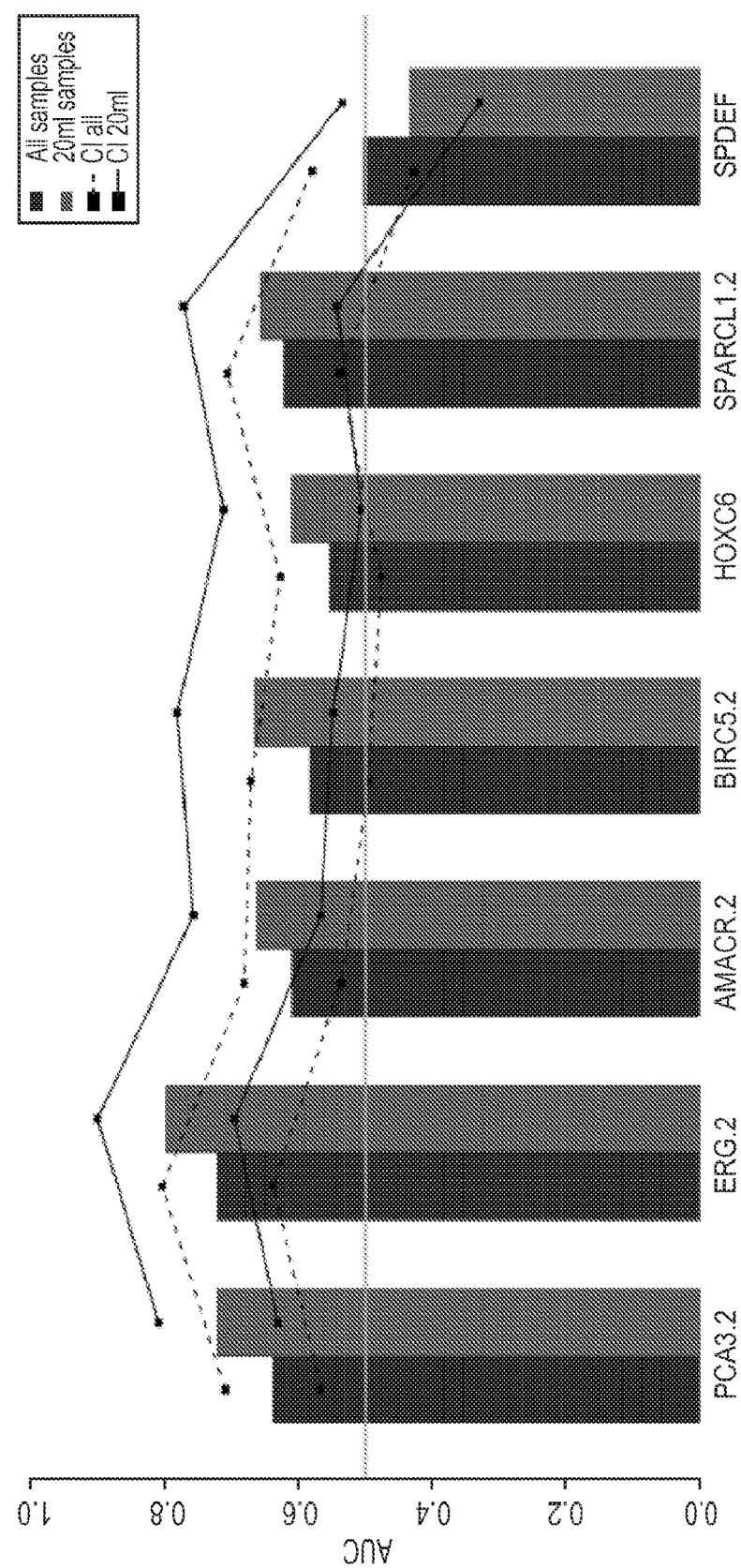
FIG. 12 is a graph comparing the AUC values generated by univariate analysis of each of the indicated genes (PCA3, ERG, AMACR, BIRC5, HOXC6, SPARCL1, and SPDEF) in samples of small volume (20 mL) with the AUC values of all samples. CI all and CI 20 mL indicates the 95% Confidence Interval for the AUCs for "All samples" and "20 mL samples", respectively. The Y axis represents the AUC values; the X axis represents each of the genes tested.

Microvesicles were isolated, RNA was extracted, and biomarker gene expression was determined as described in Examples 1 and 2. Biostatistical analysis of biomarkers (i.e., PCA3, ERG) in cohort 7 was performed by generating AUC and ROC plots based on copy number and KLK3 normalized gene expression for all the samples in the cohort. FIG. 3 shows that the AUC generated from PCA3 expression analysis is highly dependent on sample volume. For example, samples that generated an AUC greater than 0.70 were from samples where the sample volume was less than 40 mL. Conversely, samples that generated AUCs in the range of 0.60-0.65 had a sample volume of 40 mL or greater. FIG. 12 shows the univariate analysis of each indicated gene (PCA3, ERG, AMACR, BIRC5, HOXC6, SPARCL1 and SPDEF) and the generated AUCs for samples that were 20 mL or less compared to the generated AUCs for all samples. These results show that samples 20 mL of less results in increased AUC values, indicating that the diagnostic power of the single gene is increased in urine samples of smaller volume. SPDEF is a reference gene utilized for normalization, and therefore, AUC values do not improve with smaller sample volume.

Figure 13:
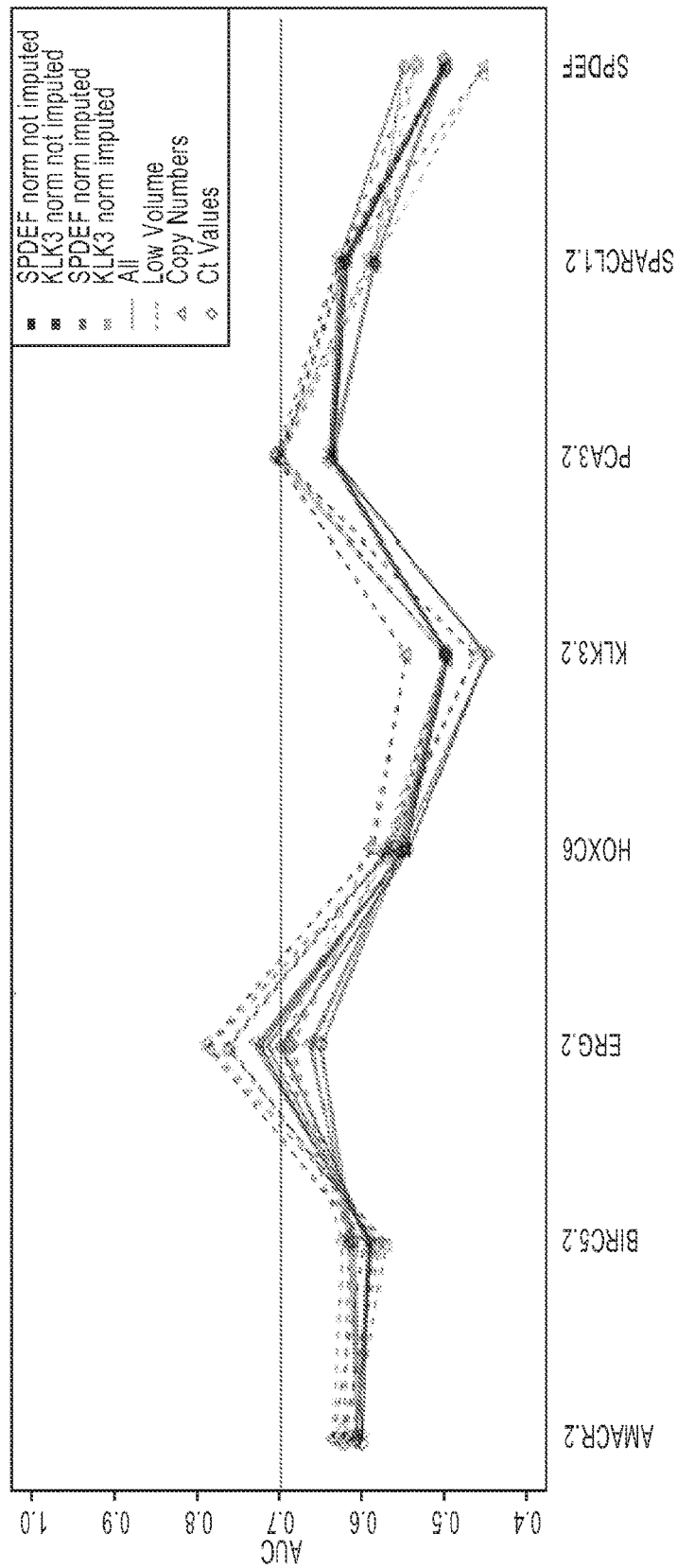
FIG. 13 is a graph showing the AUC values generated by univariate analysis of each of the indicated genes (AMACR, BIRC5, ERG, HOXC6, KLK3, PCA3, SPARCL1, and SPDEF) and comparing the AUC values between the following subsets: normalized to SPDEF or KLK3; imputed and normalized to SPDEF or KLK3; all sample volumes to low volume samples; and copy numbers to Ct values.
Figure 14A:
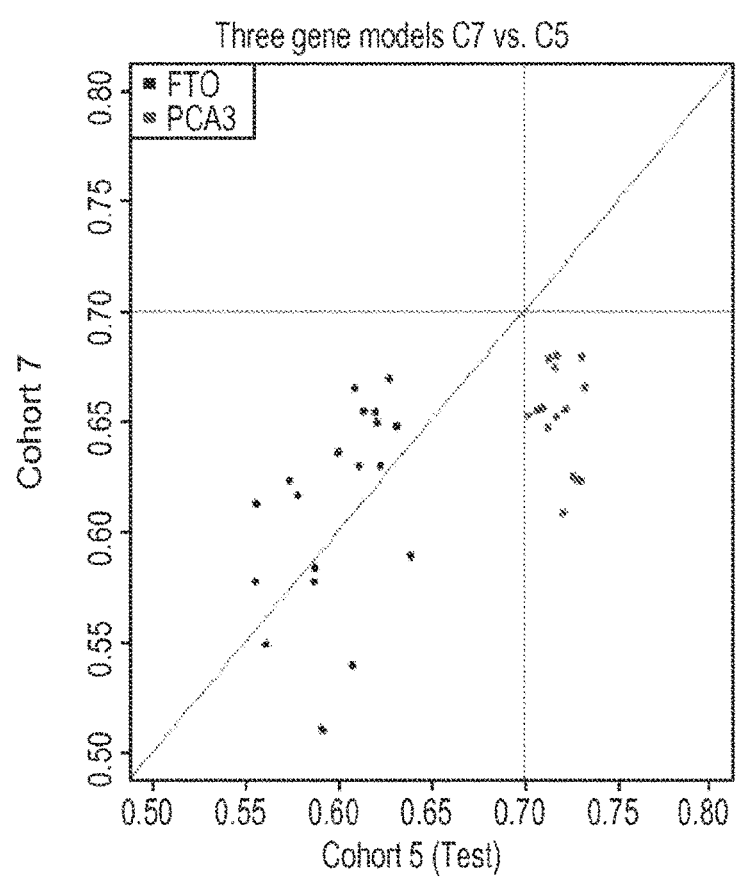
FIG. 14A and FIG. 14B are two graphs showing comparing the analysis of Cohort 5 (C5) and Cohort 7 (C7) by three gene analysis.
Figure 14B:
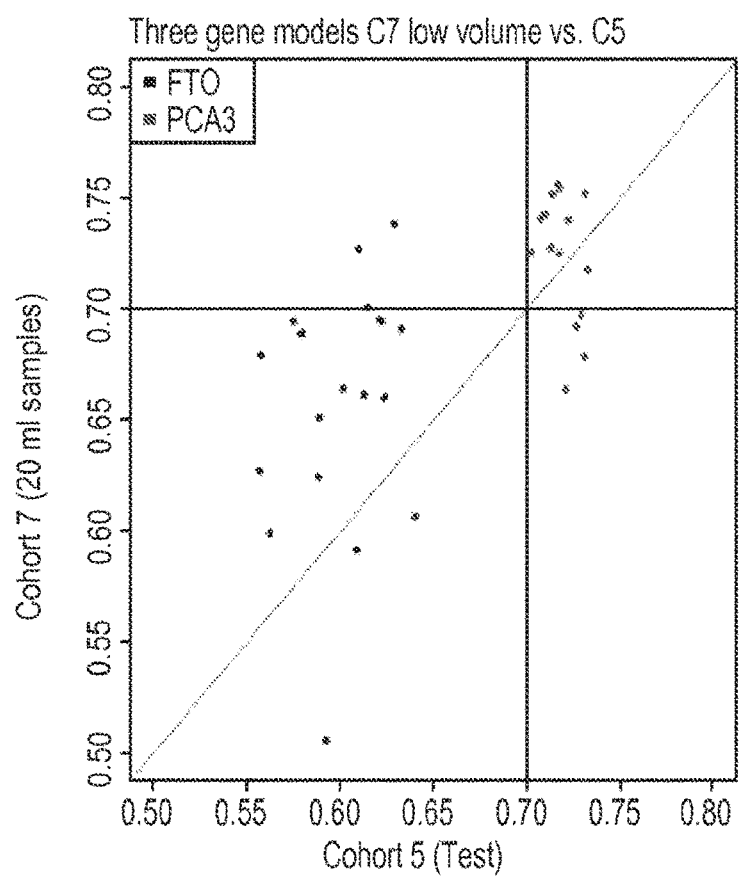

Analysis of biomarker expression for copy number rather than Ct values also show that samples with smaller volumes (20 mL) yielded improved AUC values when compared to all samples (FIG. 13).

Example 6: Scoring Patient Samples and Statistical Validation of Same

In the studies described herein, samples were used if they met the following criteria: (i) first biopsy only; (ii) patient age ≥50 years old; (iii) PSA "gray zone" level in the range of 2-10 ng/mL; and (iv) urine donation volume between 20-49 mL. Patient samples in the PSA gray zone are selected because patients with high PSA levels will almost always be biopsied, and patients with low PSA levels are typically only recommended for biopsy for other, non-PSA driven reasons.

The patient samples are scored according to a laboratory-developed test (LDT) score referred to herein as the EXO106 Score using the following algorithm:

$$EXO106\ Score = \left(\log_2 \frac{\max(1,\ ERG\ copies)}{SPDEF\ copies} + \log_2 \frac{\max(1,\ PCA3\ copies)}{SPDEF\ copies} + 16.92\right) * 1.83$$

where copy numbers are calculated using the RGQ software (Qiagen) for each gene using the on-plate calibration curves, and where the cutoff is 10. An EXO106 score less than 10 is a score associated with a lower risk of prostate cancer. An EXO106 score that is greater than or equal to 10 is a score associated with a higher risk of prostate cancer.

It is noted that the score was scaled by multiplying by 1.83 and offset by adding 16.92 to transform the EXO106 score into a more appealing and legible range. This scaling and offset, however, have no effect on the performance of the test. The transformation of the EXO106 Score puts the majority of the data in the 0-30 range, but without a cap on the score in either end (i.e., individual samples can score outside of this range). The algorithm for the EXO106 Score was configured such that the negative predictive value (NPV) of the EXO106 Score at the cut-off value of 10 is greater than the NPV of the Prostate Cancer Preventional Trial Risk Calculator (PCPTRC), where the $NPV_{PCPTRC}$ cut-off is chosen such that it predicts at least 30% of the patients as negative. The algorithm for the EXO106 Score was also designed such that the fraction of patients predicted negative (i.e., EXO106 Score less than 10) is at least 30%.

Figure 16:
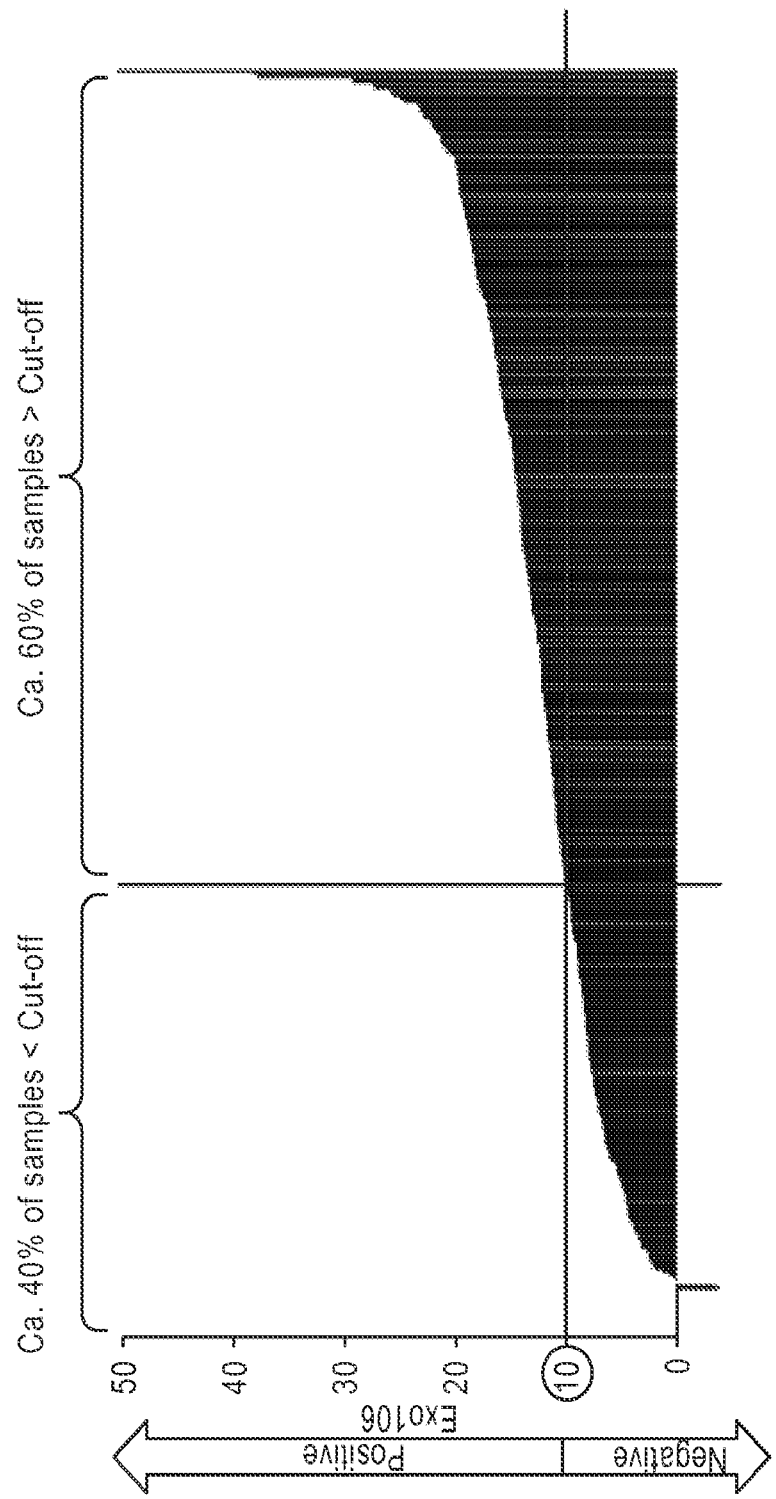
FIG. 16 is a graph depicting an exemplary EXO106 Score distribution in a patient cohort where n=453 samples, PSA median=5.3 ng/mL, and 80% of samples 2<PSA<10 ng/mL.
Figure 17:
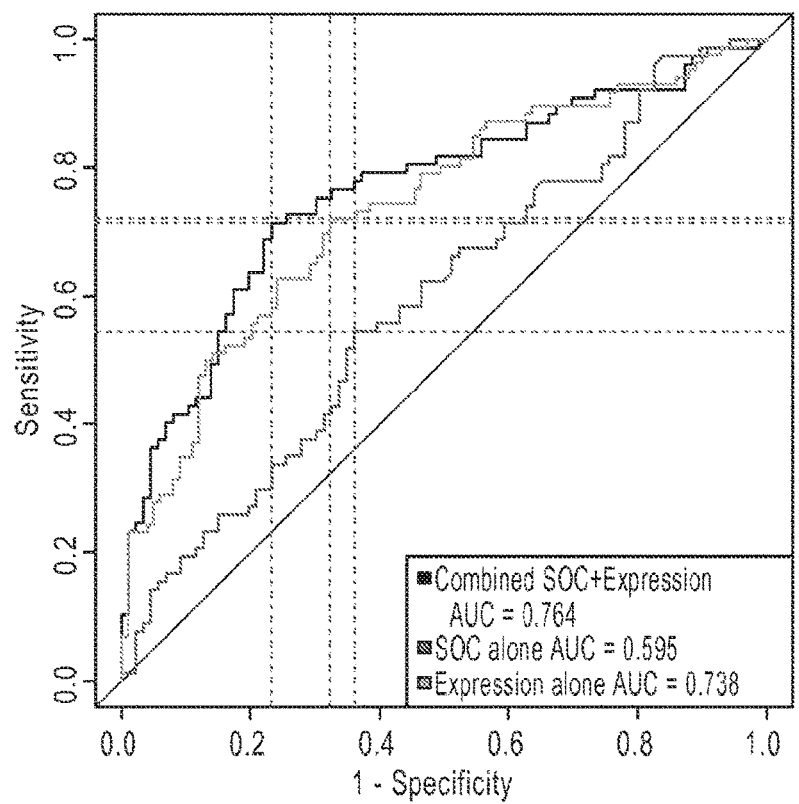
FIG. 17 is a graph depicting the AUC for EXO106 Performance on patients with any Gleason score as compared to the AUC for standard of care (SOC) treatment.
Figure 18A:
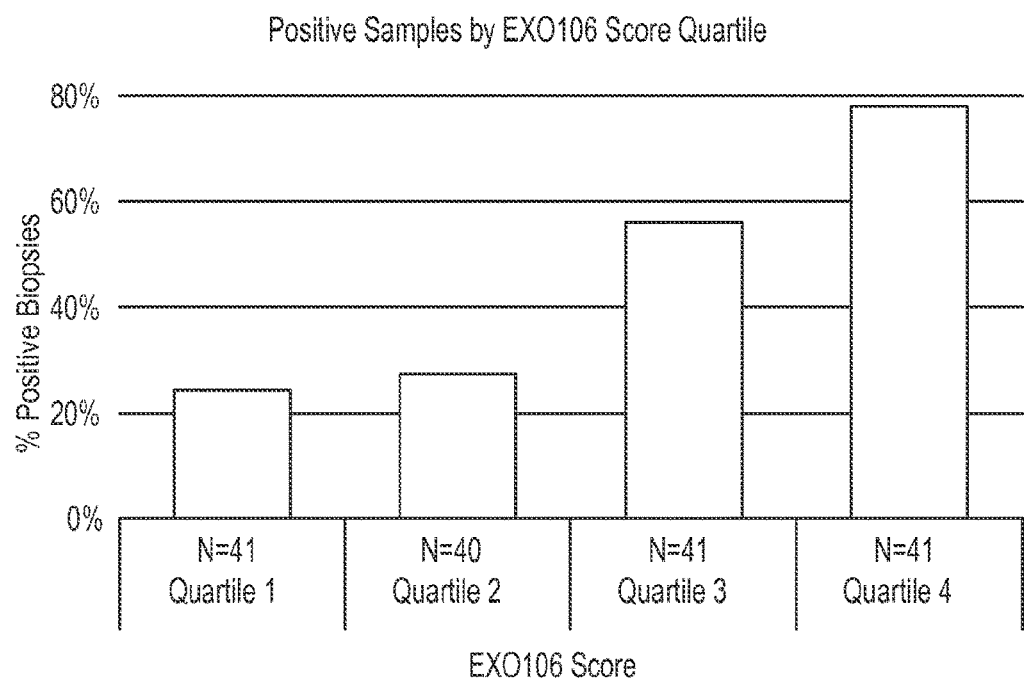
FIGS. 18A and 18B are a series of graphs depicting EXO106 performance by quartile, i.e., the percentage of samples identified as positive by biopsy by EXO106 score quartile.
Figure 18B:
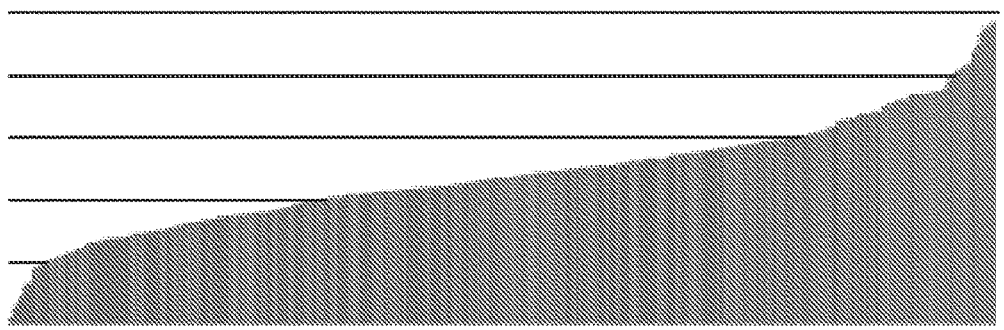

An exemplary EXO106 Score distribution in a patient cohort referred to herein as Cohort 8 (i.e., C8, n=453 samples, PSA median=5.3 ng/mL, and 80% of samples 2<PSA<10 ng/mL) is shown in FIG. 16. The AUC for EXO106 Performance on patients with any Gleason score as compared to the AUC for standard of care (SOC) treatment is shown in FIG. 17, where the AUC for SOC=0.595; AUC for EXO106=0.738; and AUC for EXO106+SOC=0.764. The patient cohort used in FIG. 17 had the following characteristics: all samples were in the PSA gray zone, were from first biopsy only, and were from low volume urine samples. EXO106 performance by quartile, i.e., the percentage of samples identified as positive by biopsy by EXO106 score quartile, is shown in FIGS. 18A and 18B. Again, these samples were from patients with any Gleason score.

Figure 19:
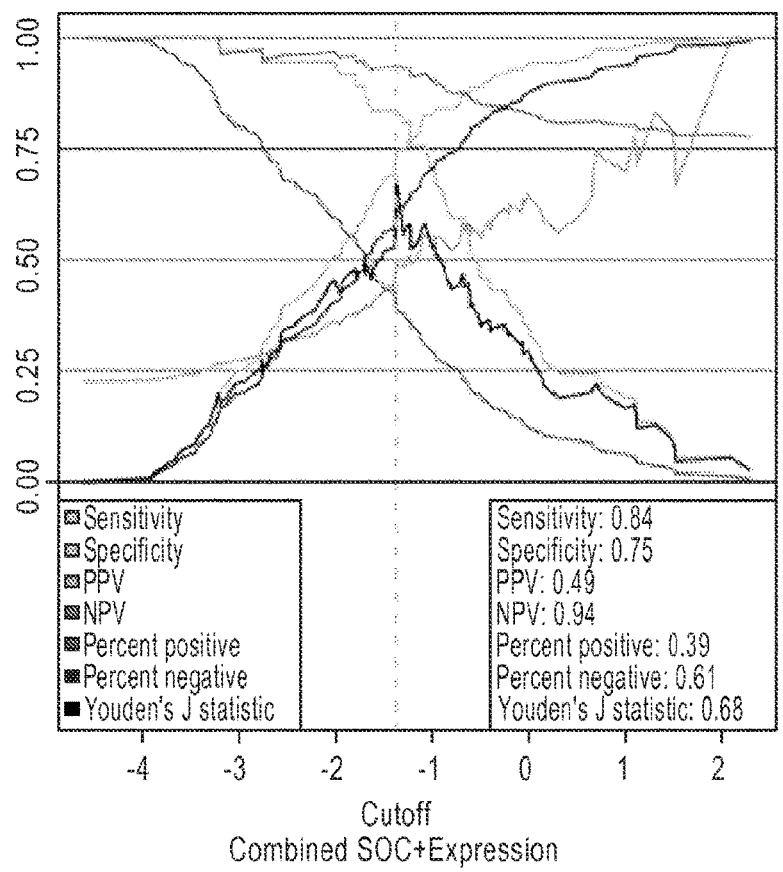
FIG. 19 is a graph depicting the performance of the EXO106 Score for high grade prostate cancer, e.g., a Gleason score greater than 6.
Figure 20:
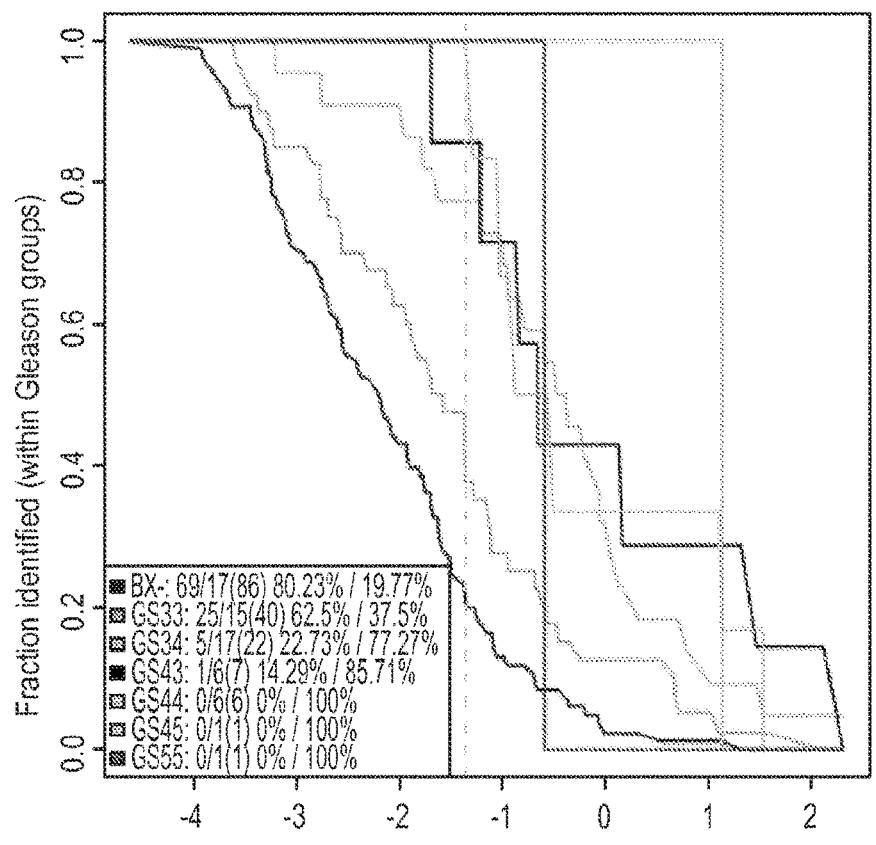
FIG. 20 is a graph depicting a breakdown of the EXO106 Score performance based on Gleason score subgroups.

The performance of the EXO106 Score for high grade prostate cancer, e.g., a Gleason score greater than 6 is shown in FIG. 19, and a breakdown of the EXO106 Score performance based on Gleason score subgroups is shown in FIG. 20.

Thus, the EXO106 score is useful in determining the prediction of a high grade prostate disease, e.g., a disease having a Gleason score greater than 6. Typically, samples from first biopsy and from repeat biopsy populations are very different and should be analyzed separately.

While the present invention has been disclosed with reference to certain embodiments, numerous modifications, alterations, and changes to the described embodiments are possible without departing from the spirit and scope of the present invention, as described above and in the appended claims. Accordingly, it is intended that the present invention not be limited to the specifically described embodiments, but that it be given the full scope to which it is entitled under the law.

TABLE 2a

Cohort 7 2 × 2 Analysis (V ≤ 100 mL, N = 236)
Model Cutoff 8.5

|  | BX POS | BX NEG |  |  |
|---|---|---|---|---|
| TEST POS | 72 | 69 | 51.1% | PPV |
| TEST NEG | 21 | 74 | 77.9% | NPV |
|  | 77.4% | 51.7% |  |  |
|  | SENS | SPEC |  |  |

TABLE 2b

Cohort 7 Gleason Score Analysis (V ≤ 100 mL, N = 236)

| Gleason* | # Missed | % Missed | Detected |
|---|---|---|---|
| 6 | 11 | 29% | 27 |
| 3 + 4 = 7 | 6 | 21% | 22 |
| 4 + 3 = 7 | 2 | 13% | 13 |
| 8 | 0 | 0% | 3 |
| 9 | 1 | 13% | 7 |
| 10 | 1 | 100% | 0 |

TABLE 2c

Cohort 7 Analysis (V ≤ 100 mL, N = 236)

| | |
|---|---|
| % TEST POS | 59.7% |
| % TEST NEG | 40.3% |

TABLE 2d

Cohort 7 Quartile Analysis (V ≤ 100 mL, N = 236)

| | % Biopsy Positive | | | | | | | |
|---|---|---|---|---|---|---|---|---|
| | Quartile 1 0.40 to 6.70 | | Quartile 2 6.70 to 8.20 | | Quartile 3 8.20 to 9.40 | | Quartile 4 9.40 to 13.60 | |
| Gleason Group | Percent | N | Percent | N | Percent | N | Percent | N |
| 6 | 39.5% | 15 | 26.3% | 10 | 21.1% | 8 | 13.2% | 5 |
| 3 + 4 = 7 | 35.7% | 10 | 39.3% | 11 | 7.1% | 2 | 17.9% | 5 |
| 4 + 3 = 7 | 60.0% | 9 | 26.7% | 4 | 6.7% | 1 | 6.7% | 1 |
| 8 | 0.0% | 0 | 66.7% | 2 | 33.3% | 1 | 0.0% | 0 |
| 9 | 62.5% | 5 | 0.0% | 0 | 25.0% | 2 | 12.5% | 1 |
| 10 | 0.0% | 0 | 0.0% | 0 | 0.0% | 0 | 100.0% | 1 |

TABLE 2e

Cohort 7 Quartile Analysis (V ≤ 100 mL, N = 236)

| Quartile 1 0.40 to 6.70 | | Quartile 2 6.70 to 8.20 | | Quartile 3 8.20 to 9.40 | | Quartile 4 9.40 to 13.60 | |
|---|---|---|---|---|---|---|---|
| % Bx POS | N | % Bx POS | N | % Bx POS | N | % Bx POS | N |
| 60.9% | 64 | 46.6% | 58 | 26.9% | 52 | 21.0% | 62 |

TABLE 3a

Cohort 7 2 × 2 Analysis (V ≤ 40 mL, N = 189)
Model Cutoff 8.5

| | BX POS | BX NEG | | |
|---|---|---|---|---|
| TEST POS | 61 | 52 | 54.0% | PPV |
| TEST NEG | 17 | 59 | 77.6% | NPV |
| | 78.2% | 53.2% | | |
| | SENS | SPEC | | |

TABLE 3b

Cohort 7 Gleason Score Analysis (V ≤ 40 mL, N = 189)

| Gleason | # Missed | % Missed | Detected |
|---|---|---|---|
| 6 | 8 | 26% | 23 |
| 3 + 4 = 7 | 6 | 24% | 19 |

TABLE 3b-continued

Cohort 7 Gleason Score Analysis (V ≤ 40 mL, N = 189)

| Gleason | # Missed | % Missed | Detected |
|---|---|---|---|
| 4 + 3 = 7 | 2 | 17% | 10 |
| 8 | 0 | 0% | 2 |
| 9 | 0 | 0% | 7 |
| 10 | 1 | 100% | 0 |

TABLE 3c

Cohort 7 Analysis (V ≤ 40 mL, N = 189)

| | |
|---|---|
| % TEST POS | 59.8% |
| % TEST NEG | 40.2% |

TABLE 3d

Cohort 7 Quartile Analysis (V ≤ 40 mL, N = 189)

| | % Biopsy Positive | | | | | | | |
|---|---|---|---|---|---|---|---|---|
| | Quartile 1 0.70 to 6.70 | | Quartile 2 6.70 to 8.20 | | Quartile 3 8.20 to 9.70 | | Quartile 4 9.70 to 13.60 | |
| Gleason Group | Percent | N | Percent | N | Percent | N | Percent | N |
| 6 | 38.7% | 12 | 29.0% | 9 | 19.4% | 6 | 12.9% | 4 |
| 3 + 4 = 7 | 32.0% | 8 | 40.0% | 10 | 8.0% | 2 | 20.0% | 5 |
| 4 + 3 = 7 | 58.3% | 7 | 25.0% | 3 | 8.3% | 1 | 8.3% | 1 |
| 8 | 0.0% | 0 | 50.0% | 1 | 50.0% | 1 | 0.0% | 0 |
| 9 | 71.4% | 5 | 0.0% | 0 | 28.6% | 2 | 0.0% | 0 |
| 10 | 0.0% | 0 | 0.0% | 0 | 0.0% | 0 | 100.0% | 1 |

TABLE 3e

Cohort 7 Quartile Analysis (V ≤ 40 mL, N = 189)

| Quartile 1 0.70 to 6.70 | | Quartile 2 6.70 to 8.20 | | Quartile 3 8.20 to 9.70 | | Quartile 4 9.70 to 13.60 | |
|---|---|---|---|---|---|---|---|
| % Bx POS | N | % Bx POS | N | % Bx POS | N | % Bx POS | N |
| 65.3% | 49 | 50.0% | 46 | 24.0% | 50 | 25.0% | 44 |

TABLE 4a

Cohort 7 2 × 2 Analysis (V ≤ 20 mL, N = 122)
Model Cutoff 8.5

| | BX POS | BX NEG | | |
|---|---|---|---|---|
| TEST POS | 42 | 26 | 61.8% | PPV |
| TEST NEG | 12 | 42 | 77.8% | NPV |
| | 77.8% | 61.8% | | |
| | SENS | SPEC | | |

TABLE 4b

Cohort 7 Gleason Score Analysis (V ≤ 20 mL, N = 122)

| Gleason | # Missed | % Missed | Detected |
|---|---|---|---|
| 6 | 7 | 28% | 18 |
| 3 + 4 = 7 | 3 | 20% | 12 |

TABLE 4b-continued

Cohort 7 Gleason Score Analysis (V ≤ 20 mL, N = 122)

| Gleason | # Missed | % Missed | Detected |
|---|---|---|---|
| 4 + 3 = 7 | 2 | 25% | 6 |
| 8 | 0 | 0% | 1 |
| 9 | 0 | 0% | 5 |
| 10 | 0 | #DIV/0! | 0 |

TABLE 4c

Cohort 7 Analysis (V ≤ 20 mL, N = 122)

| % TEST POS | 55.7% |
|---|---|
| % TEST NEG | 44.3% |

TABLE 4d

Cohort 7 Quartile Analysis (V ≤ 20 mL, N = 122)

| | % Biopsy Positive | | | | | | | |
|---|---|---|---|---|---|---|---|---|
| | Quartile 1 2.20 to 6.70 | | Quartile 2 6.70 to 8.20 | | Quartile 3 8.20 to 9.40 | | Quartile 4 9.40 to 13.60 | |
| Gleason Group | Percent | N | Percent | N | Percent | N | Percent | N |
| 6 | 40.0% | 10 | 28.0% | 7 | 20.0% | 5 | 12.0% | 3 |
| 3 + 4 = 7 | 26.7% | 4 | 46.7% | 7 | 13.3% | 2 | 13.3% | 2 |
| 4 + 3 = 7 | 62.5% | 5 | 12.5% | 1 | 12.5% | 1 | 12.5% | 1 |
| 8 | 0.0% | 0 | 0.0% | 0 | 100.0% | 1 | 0.0% | 0 |
| 9 | 80.0% | 4 | 0.0% | 0 | 20.0% | 1 | 0.0% | 0 |
| 10 | #DIV/0! | 0 | #DIV/0! | 0 | #DIV/0! | 0 | #DIV/0! | 0 |

TABLE 4e

Cohort 7 Quartile Analysis (V ≤ 20 mL, N = 122)

| Quartile 1 2.20 to 6.70 | | Quartile 2 6.70 to 8.20 | | Quartile 3 8.20 to 9.40 | | Quartile 4 9.40 to 13.60 | |
|---|---|---|---|---|---|---|---|
| % Bx POS | N | % Bx POS | N | % Bx POS | N | % Bx POS | N |
| 79.3% | 29 | 50.0% | 30 | 35.7% | 28 | 17.1% | 35 |

REFERENCES

Al-Nedawi, K., B. Meehan, J. Micallef, V. Lhotak, L. May, A. Guha, and J. Rak. 2008. Intercellular transfer of the oncogenic receptor EGFRvIII by microvesicles derived from tumour cells. Nat Cell Biol. 10:619-24.

Balzar, M., M. J. Winter. C. J. de Boer, and S. V. Litvinov. 1999. The biology of the 17-1A antigen (Ep-CAM). J Mol Med. 77:699-712.

Bossi, A., F. Bonini, A. P. Turner, and S. A. Piletsky. 2007. Molecularly imprinted polymers for the recognition of proteins: the state of the art. Biosens Bioelectron. 22:1131-7.

Bussemakers, M. J., A. van Bokhoven, G. W. Verhaegh, F. P. Smit, H. F. Karthaus, J. A. Schalken, F. M. Debruyne, N. Ru, and W. B. Isaacs. 1999. DD3: a new prostate-specific gene, highly overexpressed in prostate cancer. Cancer Res. 59:5975-9.

Chen, C., J. Skog, C. H. Hsu, R. T. Lessard, L. Balaj, T. Wurdinger, B. S. Carter, X. O. Breakefield, M. Toner, and D. Irimia. 2010. Microfluidic isolation and transcriptome analysis of serum microvesicles. Lab Chip. 10:505-11.

Cheruvanky. A., H. Zhou, T. Pisitkun, J. B. Kopp, M. A. Knepper, P. S. Yuen, and R. A. Star. 2007. Rapid isolation of urinary exosomal biomarkers using a nanomembrane ultrafiltration concentrator. Am J Physiol Renal Physiol. 292:F1657-61.

Cotton, R. G., N. R. Rodrigues, and R. D. Campbell. 1988. Reactivity of cytosine and thymine in single-base-pair mismatches with hydroxylamine and osmium tetroxide and its application to the study of mutations. Proc Natl Acad Sci USA. 85:4397-401.

Cowell, J. K., and K. C. Lo. 2009. Application of oligonucleotides arrays for coincident comparative genomic hybridization, ploidy status and loss of heterozygosity studies in human cancers. Methods Mol Biol. 556:47-65.

Deras, I. L., S. M. Aubin, A. Blase, J. R. Day, S. Koo, A. W. Partin, W. J. Ellis, L. S. Marks, Y. Fradet, H. Rittenhouse, and J. Groskopf. 2008. PCA3: a molecular urine assay for predicting prostate biopsy outcome. J Urol. 179:1587-92.

Furusato, B., C. L. Gao, L. Ravindranath, Y. Chen. J. Cullen, D. G. McLeod, A. Dobi, S. Srivastava, G. Petrovics, and I. A. Sesterhenn. 2008. Mapping of TMPRSS2-ERG fusions in the context of multi-focal prostate cancer. Mod Pathol. 21:67-75.

Guatelli, J. C., K. M. Whitfield, D. Y. Kwoh, K. J. Barringer, D. D. Richman, and T. R. Gingeras. 1990. Isothermal, in vitro amplification of nucleic acids by a multienzyme reaction modeled after retroviral replication. Proc Natl Acad Sci USA. 87:1874-8.

Hahn, P. J. 1993. Molecular biology of double-minute chromosomes. Bioessays. 15:477-84.

Hessels, D., F. P. Smit, G. W. Verhaegh, J. A. Witjes, E. B. Cornel, and J. A. Schalken. 2007. Detection of TMPRSS2-ERG fusion transcripts and prostate cancer antigen 3 in urinary sediments may improve diagnosis of prostate cancer. Clin Cancer Res. 13:5103-8.

Johnson, S., D. Evans, S. Laurenson, D. Paul, A. G. Davies, P. K. Ferrigno, and C. Walti. 2008. Surface-immobilized peptide aptamers as probe molecules for protein detection. Anal Chem. 80:978-83.

Kwoh, D. Y., G. R. Davis, K. M. Whitfield, H. L. Chappelle, L. J. DiMichele, and T. R. Gingeras. 1989. Transcription-based amplification system and detection of amplified human immunodeficiency virus type 1 with a bead-based sandwich hybridization format. Proc Natl Acad Sci USA. 86:1173-7.

Laxman, B., D. S. Morris, J. Yu, J. Siddiqui, J. Cao, R. Mehra, R. J. Lonigro, A. Tsodikov, J. T. Wei, S. A. Tomlins, and A. M. Chinnaiyan. 2008. A first-generation multiplex biomarker analysis of urine for the early detection of prostate cancer. Cancer Res. 68:645-9.

Laxman, B., S. A. Tomlins, R. Mehra, D. S. Morris, L. Wang, B. E. Helgeson, R. B. Shah, M. A. Rubin, J. T. Wei, and A. M. Chinnaiyan. 2006. Noninvasive detection of TMPRSS2:ERG fusion transcripts in the urine of men with prostate cancer. Neoplasia. 8:885-8.

Li, J., L. Wang, H. Mamon, M. H. Kulke, R. Berbeco, and G. M. Makrigiorgos. 2008. Replacing PCR with COLD-PCR enriches variant DNA sequences and redefines the sensitivity of genetic testing. Nat Med. 14:579-84.

Lipson, D., T. Raz, A. Kieu, D. R. Jones, E. Giladi, E. Thayer, J. F. Thompson, S. Letovsky, P. Milos, and M. Causey. 2009. Quantification of the yeast transcriptome by single-molecule sequencing. Nat Biotechnol. 27:652-8.

Mattick, J. S. 2004. RNA regulation: a new genetics?Nat Rev Genet. 5:316-23.

Miele. E. A., D. R. Mills, and F. R. Kramer. 1983. Autocatalytic replication of a recombinant RNA. J Mol Biol. 171:281-95.

Myers, R. M., Z. Larin, and T. Maniatis. 1985. Detection of single base substitutions by ribonuclease cleavage at mismatches in RNA:DNA duplexes. Science. 230:1242-6.

Nguyen, P. N., P. Violette, S. Chan, S. Tanguay, W. Kassouf, A. Aprikian, and J. Z. Chen. 2011. A panel of TMPRSS2:ERG fusion transcript markers for urine-based prostate cancer detection with high specificity and sensitivity. Eur Urol. 59:407-14.

Nilsson, J., J. Skog, A. Nordstrand, V. Baranov, L. Mincheva-Nilsson, X. O. Breakefield, and A. Widmark. 2009. Prostate cancer-derived urine exosomes: a novel approach to biomarkers for prostate cancer. Br J Cancer. 100:1603-7.

Orita, M., H. Iwahana, H. Kanazawa, K. Hayashi, and T. Sekiya. 1989. Detection of polymorphisms of human DNA by gel electrophoresis as single-strand conformation polymorphisms. Proc Natl Acad Sci USA. 86:2766-70.

Orozco, A. F., and D. E. Lewis. 2010. Flow cytometric analysis of circulating microparticles in plasma. Cytometry A. 77:502-14.

Palanisamy, N., B. Ateeq, S. Kalyana-Sundaram, D. Pflueger, K. Ramnarayanan, S. Shankar, B. Han, Q. Cao, X. Cao, K. Suleman, C. Kumar-Sinha, S. M. Dhanasekaran, Y. B. Chen, R. Esgueva, S. Banerjee, C. J. LaFargue, J. Siddiqui, F. Demichelis, P. Moeller, T. A. Bismar, R. Kuefer, D. R. Fullen, T. M. Johnson, J. K. Greenson, T. J. Giordano, P. Tan, S. A. Tomlins, S. Varambally, M. A. Rubin, C. A. Maher, and A. M. Chinnaiyan. 2010. Rearrangements of the RAF kinase pathway in prostate cancer, gastric cancer and melanoma. Nat Med. 16:793-8.

Petrovics, G., A. Liu, S. Shaheduzzaman, B. Furusato, C. Sun, Y. Chen, M. Nau, L. Ravindranath, A. Dobi, V. Srikantan, I. A. Sesterhenn, D. G. McLeod, M. Vahey, J. W. Moul, and S. Srivastava. 2005. Frequent overexpression of ETS-related gene-1 (ERG1) in prostate cancer transcriptome. Oncogene. 24:3847-52.

Raposo, G., H. W. Nijman, W. Stoorvogel, R. Liejendekker, C. V. Harding, C. J. Melief, and H. J. Geuze. 1996. B lymphocytes secrete antigen-presenting vesicles. J Exp Med. 183:1161-72.

Rice, K. R., Y. Chen, A. Ali, E. J. Whitman, A. Blase, M. Ibrahim, S. Elsamanoudi, S. Brassell, B. Furusato, N. Stingle, I. A. Sesterhenn, G. Petrovics, S. Miick, H. Rittenhouse, J. Groskopf, D. G. McLeod, and S. Srivastava. 2010. Evaluation of the ETS-related gene mRNA in urine for the detection of prostate cancer. Clin Cancer Res. 16:1572-6.

Rostad, K., O. J. Hellwinkel, S. A. Haukaas, O. J. Halvorsen, A. M. Oyan, A. Haese, L. Budaus, H. Albrecht, L. A. Akslen, T. Schlomm, and K. H. Kalland. 2009. TMPRSS2:ERG fusion transcripts in urine from prostate cancer patients correlate with a less favorable prognosis. APMIS. 117:575-82.

Salami, S. S., F. Schmidt, B. Laxman, M. M. Regan, D. S. Rickman, D. Scherr, G. Bueti, J. Siddiqui, S. A. Tomlins, J. T. Wei, A. M. Chinnaiyan, M. A. Rubin, and M. G. Sanda. 2011. Combining urinary detection of TMPRSS2:ERG and PCA3 with serum PSA to predict diagnosis of prostate cancer. Urol Oncol.

Skog, J., T. Wurdinger, S. van Rijn, D. H. Meijer, L. Gainche, M. Sena-Esteves, W. T. Curry. Jr., B. S. Carter. A. M. Krichevsky, and X. O. Breakefield. 2008. Glioblastoma microvesicles transport RNA and proteins that promote tumour growth and provide diagnostic biomarkers. Nat Cell Biol. 10:1470-6.

Steemers, F. J., W. Chang, G. Lee, D. L. Barker, R. Shen, and K. L. Gunderson. 2006. Whole-genome genotyping with the single-base extension assay. Nat Methods. 3:31-3.

Taylor. D. D., and C. Gercel-Taylor. 2008. MicroRNA signatures of tumor-derived exosomes as diagnostic biomarkers of ovarian cancer. Gynecol Oncol. 110:13-21.

Ting, D. T., D. Lipson, S. Paul, B. W. Brannigan, S. Akhavanfard, E. J. Coffman, G. Contino, V. Deshpande, A. J. Iafrate, S. Letovsky, M. N. Rivera, N. Bardeesy, S. Maheswaran, and D. A. Haber. 2011. Aberrant overexpression of satellite repeats in pancreatic and other epithelial cancers. Science. 331:593-6.

Tomlins, S. A., S. M. Aubin, J. Siddiqui, R. J. Lonigro, L. Sefton-Miller, S. Miick, S. Williamsen, P. Hodge, J. Meinke, A. Blase, Y. Penabella, J. R. Day, R. Varambally, B. Han, D. Wood, L. Wang, M. G. Sanda, M. A. Rubin, D. R. Rhodes, B. Hollenbeck, K. Sakamoto, J. L. Silberstein, Y. Fradet, J. B. Amberson, S. Meyers, N. Palanisamy, H. Rittenhouse, J. T. Wei, J. Groskopf, and A. M. Chinnaiyan. 2011. Urine TMPRSS2:ERG Fusion Transcript Stratifies Prostate Cancer Risk in Men with Elevated Serum PSA. Sci Transl Med. 3:94ra72.

Tomlins, S. A., D. R. Rhodes, S. Perner, S. M. Dhanasekaran, R. Mehra, X. W. Sun, S. Varambally, X. Cao, J. Tchinda, R. Kuefer, C. Lee, J. E. Montie, R. B. Shah, K. J. Pienta, M. A. Rubin, and A. M. Chinnaiyan. 2005. Recurrent fusion of TMPRSS2 and ETS transcription factor genes in prostate cancer. Science. 310:644-8.

Velculescu, V. E., L. Zhang, B. Vogelstein, and K. W. Kinzler. 1995. Serial analysis of gene expression. Science. 270:484-7.

Went, P. T., A. Lugli, S. Meier, M. Bundi, M. Mirlacher, G. Sauter, and S. Dirnhofer. 2004. Frequent EpCam protein expression in human carcinomas. Hum Pathol. 35:122-8.

Wong, M. L., and J. F. Medrano. 2005. Real-time PCR for mRNA quantitation. Biotechniques. 39:75-85.

Zhang, M., D. E. Latham, M. A. Delaney, and A. Chakravarti. 2005. Survivin mediates resistance to antiandrogen therapy in prostate cancer. Oncogene. 24:2474-82.

SEQUENCE LISTING

<160> NUMBER OF SEQ ID NOS: 44

<210> SEQ ID NO 1
<211> LENGTH: 543
<212> TYPE: DNA
<213> ORGANISM: Artificial Sequence
<220> FEATURE:
<223> OTHER INFORMATION: Chemically synthesized Q beta particle

<400> SEQUENCE: 1

```
aaacggttct tgtgacccat ccgttactcg ccaggcatat gctgacgtga ccttttcgtt    60
cacgcagtat agtaccgatg aggaacgagc ttttgttcgt acagagcttg ctgctctgct   120
cgctagtcct agcgtcctca gttagatcct tatcagattc ttggaccaac aagtagccgc   180
cttgcaaatc caggcagtgg ccagatccag ctttggcagt tcctcctgga gctcctgtcg   240
gacagctccc ggtcggatgt gctgctgag cccttccgcc gcggtgtcat ggagaaactc    300
cagctgggcc cagagattct gcagcgggaa aacctgtccg tgacgtggat tggtgctgca   360
cccctcatcc tgtctcggat tgtgggaggc tgggagtgcg agaagcattc caacccctgg   420
caggtgcttg tggcctctcg tggcagggca gtctgcggcg tgttctggt gcaccccag    480 tgggtcctca cagctgccca ctgcatcagg aacaaaagcg tgatcttgct gggtcggcac   540
agc                                                                543
```

<210> SEQ ID NO 2
<211> LENGTH: 300
<212> TYPE: DNA
<213> ORGANISM: Homo sapiens

<400> SEQUENCE: 2

```
cagtcgaaag ctgctcaacc atctccttcc acagtgccca aaactgaaga ccagcgtcct    60
cagttagatc cttatcagat tcttggacca acaagtagcc gccttgcaaa tccaggcagt   120
ggccagatcc agctttggca gttcctcctg gagctcctgt cggacagctc caactccagc   180
tgcatcacct gggaaggcac caacggggag ttcaagatga cggatcccga cgaggtggcc   240
cggcgctggg gagagcggaa gagcaaaccc aacatgaact acgataagct cagccgcgcc   300
```

<210> SEQ ID NO 3
<211> LENGTH: 386
<212> TYPE: RNA
<213> ORGANISM: Homo sapiens

<400> SEQUENCE: 3

```
gggagacgaa gggccccaga gcagccgagc ggccgccagg gaggaacgca gaacgcccag    60
ccccaggaca cagggcggac accacgacgg caccgagacc aggcagcaaa gaaagacaca   120
gacaccaagg caggggaga aaagaaagg cgcgacacca cgaggccaca cacgcgaaag    180
gagaaaaaca cacagaaaca gcaagagaca aaaagcaaga ggacaggcac accagcccca   240
aaaccacaca cacaggaagc acaaaaggaa gcacagagac ccgggagaaa gcccggccac   300
cgcggccgca gcggaccga accgggaaag accgccacaa ccacacaaca acgagccgga   360
agcaaaagga aagccggggg ccaaga                                       386
```

<210> SEQ ID NO 4
<211> LENGTH: 3352
<212> TYPE: DNA
<213> ORGANISM: Homo sapiens

<400> SEQUENCE: 4

```
ggggcgtggc gccggggatt gggagggctt cttgcaggct gctgggctgg ggctaagggc    60
tgctcagttt ccttcagcgg ggcactggga agcgccatgg cactgcaggg catctcggtc   120
gtggagctgt ccggcctggc cccggccccg ttctgtgcta tggtcctggc tgacttcggg   180
gcgcgtgtgg tacgcgtgga ccggcccggc tcccgctacg acgtgagccg cttgggccgg   240
```

```
ggcaagcgct cgctagtgct ggacctgaag cagccgcggg gagccgccgt gctgcggcgt      300
ctgtgcaagc ggtcggatgt gctgctggag cccttccgcc gcggtgtcat ggagaaactc      360
cagctgggcc cagagattct gcagcgggaa atccaaggc ttatttatgc caggctgagt       420
ggatttggcc agtcaggaag cttctgccgg ttagctggcc acgatatcaa ctatttggct      480
ttgtcaggtg ttctctcaaa aattggcaga agtggtgaga atccgtatgc cccgctgaat      540
ctcctggctg actttgctgg tggtggcctt atgtgtgcac tgggcattat aatggctctt      600
tttgaccgca cacgcactgg caagggtcag gtcattgatg caaatatggt ggaaggaaca      660
gcatatttaa gttctttct gtggaaaact cagaaattga gtctgtggga agcacctcga       720
ggacagaaca tgttggatgg tggagcacct ttctatacga cttacaggac agcagatggg      780
gaattcatgg ctgttggagc aatagaaccc cagttctacg agctgctgat caaaggactt      840
ggactaaagt ctgatgaact tcccaatcag atgagcatgg atgattggcc agaaatgaag      900
aagaagtttg cagatgtatt tgcagagaag acgaaggcag agtggtgtca aatctttgac      960
ggcacagatg cctgtgtgac tccggttctg acttttgagg aggttgttca tcatgatcac     1020
aacaaggaac ggggctcgtt tatcaccagt gaggagcagg acgtgagccc ccgccctgca     1080
cctctgctgt taaacacccc agccatccct tctttcaaaa gggatccttt cataggagaa     1140
cacactgagg agatacttga agaatttgga ttcagccgcg aagagattta tcagcttaac     1200
tcagataaaa tcattgaaag taataaggta aaagctagtc tctaacttcc aggcccacgg     1260
ctcaagtgaa tttgaatact gcatttacag tgtagagtaa cacataacat tgtatgcatg     1320
gaaacatgga ggaacagtat tacagtgtcc taccactcta atcaagaaaa gaattacaga     1380
ctctgattct acagtgatga ttgaattcta aaaatggtta tcattagggc ttttgattta     1440
taaaactttg ggtacttata ctaaattatg gtagttattc tgccttccag tttgcttgat     1500
atatttgttg atattaagat tcttgactta tattttgaat gggttctagt gaaaaggaa      1560 tgatatattc ttgaagacat cgatatacat ttatttacac tcttgattct acaatgtaga     1620
aaatgaggaa atgccacaaa ttgtatggtg ataaaagtca cgtgaaacag agtgattggt     1680
tgcatccagg cctttgtct tggtgttcat gatctccctc taagcacatt ccaaactta      1740 gcaacagtta tcacactttg taatttgcaa agaaaagttt cacctgtatt gaatcagaat     1800
gccttcaact gaaaaaaaca tatccaaaat aatgaggaaa tgtgttggct cactacgtag     1860
agtccagagg gacagtcagt tttagggttg cctgtatcca gtaactcggg gcctgtttcc     1920
ccgtgggtct ctgggctgtc agcttttcctt tctccatgtg tttgatttct cctcaggctg    1980
gtagcaagtt ctggatctta tacccaacac acagcaacat ccagaaataa agatctcagg     2040
accccccagc aagtcgtttt gtgtctcctt ggactgagtt aagttacaag cctttcttat     2100
acctgtcttt gacaaagaag acgggattgt ctttacataa aaccagcctg ctcctggagc     2160
ttccctggac tcaacttcct aaaggcatgt gaggaagggg tagattccac aatctaatcc     2220
gggtgccatc agagtagagg gagtagagaa tggatgttgg gtaggccatc aataaggtcc     2280
attctgcgca gtatctcaac tgccgttcaa caatcgcaag aggaaggtgg agcaggtttc     2340
ttcatcttac agttgagaaa acagagactc agaagggctt cttagttcat gtttccctta     2400
gcgcctcagt gattttttca tggtggctta ggccaaaaga aatatctaac cattcaattt     2460
ataaataatt aggtccccaa cgaattaaat attatgtcct accaactat tagctgcttg      2520 aaaaatataa tacacataaa taaaaaaata tattttcat ttctatttca ttgttaatca      2580
caactactta ctaaggagat gtatgcacct attggacact gtgcaacttc tcacctggaa     2640
```

```
tgagattgga cactgctgcc ctcatttct gctccatgtt ggtgtccata tagtacttga    2700 tttttatca gatggcctgg aaacccagt ctcacaaaaa tatgaaatta tcagaaggat    2760
tatagtgcaa tcttatgttg aaagaatgaa ctacctcact agtagttcac gtgatgtctg    2820
acagatgttg agtttcattg tgtttgtgtg ttcaaatttt taaatattct gagatactct    2880
tgtgaggtca ctctaatgcc ctgggtgcct tggcacagtt ttagaaatac cagttgaaaa    2940
tatttgctca ggaatatgca actaggaagg ggcagaatca gaatttaagc tttcatattc    3000
tagccttcag tcttgttctt caaccatttt taggaacttt cccataaggt tatgttttcc    3060
agcccaggca tggaggatca cttgaggcca agagttcgag accagcctgg ggaacttggc    3120
tggacctccg tttctacgaa ataaaaataa aaaaattatc caggtatggt ggtgtgtgcc    3180
tgtagtccta tctactcaag ggtggggcag gaggatcact tgagcccagg aatttgaggc    3240
cacagtgaat taggattgca ccactgcact ctagcccagg caacagaaca agaacctgtc    3300
tctaaataaa taaataaaaa taataataat aaaaagatg ttttccctac aa            3352
```

<210> SEQ ID NO 5
<211> LENGTH: 2655
<212> TYPE: DNA
<213> ORGANISM: Homo sapiens

<400> SEQUENCE: 5

```
cccagaaggc cgcgggggt ggaccgccta agagggcgtg cgctcccgac atgccccgcg      60
gcgcgccatt aaccgccaga tttgaatcgc gggacccgtt ggcagaggtg gcggcggcgg    120
catgggtgcc ccgacgttgc ccctgcctg gcagcccttt ctcaaggacc accgcatctc     180
tacattcaag aactggccct tcttggaggg ctgcgcctgc acccggagc ggatggccga     240 ggctggcttc atccactgcc ccactgagaa cgagccagac ttggcccagt gtttcttctg    300
cttcaaggag ctggaaggct gggagccaga tgacgacccc atagaggaac ataaaaagca    360
ttcgtccggt tgcgctttcc tttctgtcaa gaagcagttt gaagaattaa cccttggtga    420
atttttgaaa ctggacagag aaagagccaa gaacaaaatt gcaaaggaaa ccaacaataa    480
gaagaaagaa tttgaggaaa ctgcggagaa agtgcgccgt gccatcgagc agctggctgc    540
catggattga ggcctctggc cggagctgcc tggtcccaga gtggctgcac cacttccagg    600
gtttattccc tggtgccacc agccttcctg tgggcccctt agcaatgtct taggaaagga    660
gatcaacatt tcaaattag atgtttcaac tgtgctcttg ttttgtcttg aaagtggcac    720
cagaggtgct tctgcctgtg cagcgggtgc tgctggtaac agtggctgct tctctctctc    780 tctctcttt tgggggctc atttttgctg ttttgattcc cgggcttacc aggtgagaag    840
tgagggagga agaaggcagt gtccctttg ctagagctga cagcttttgtt cgcgtgggca    900 gagccttcca cagtgaatgt gtctggacct catgttgttg aggctgtcac agtcctgagt    960
gtggacttgg caggtgcctg ttgaatctga gctgcaggtt ccttatctgt cacacctgtg   1020
cctcctcaga ggacagtttt tttgttgttg tgtttttttg ttttttttt tttggtagat   1080 gcatgacttg tgtgtgatga gagaatggag acagagtccc tggctcctct actgtttaac   1140
aacatggctt tcttattttg tttgaattgt taattcacag aatagcacaa actacaatta   1200
aaactaagca caaagccatt ctaagtcatt ggggaaacgg ggtgaacttc aggtggatga   1260
ggagacagaa tagagtgata ggaagcgtct ggcagatact ccttttgcca ctgctgtgtg   1320
attagacagg cccagtgagc cgcggggcac atgctggccg ctcctccctc agaaaaaggc   1380
```

```
agtggcctaa atccttttta aatgacttgg ctcgatgctg tgggggactg gctgggctgc    1440
tgcaggccgt gtgtctgtca gcccaacctt cacatctgtc acgttctcca cacggggag     1500 agacgcagtc cgcccaggtc cccgctttct ttggaggcag cagctcccgc agggctgaag    1560
tctggcgtaa gatgatggat ttgattcgcc ctcctccctg tcatagagct gcagggtgga    1620
ttgttacagc ttcgctggaa acctctggag gtcatctcgg ctgttcctga gaaataaaaa    1680
gcctgtcatt tcaaacactg ctgtggaccc tactgggttt ttaaaatatt gtcagttttt    1740
catcgtcgtc cctagcctgc caacagccat ctgcccagac agccgcagtg aggatgagcg    1800
tcctggcaga gacgcagttg tctctgggcg cttgccagag ccacgaaccc cagacctgtt    1860
tgtatcatcc gggctccttc cgggcagaaa caactgaaaa tgcacttcag acccacttat    1920
ttctgccaca tctgagtcgg cctgagatag acttttccct ctaaactggg agaatatcac    1980
agtggttttt gttagcagaa aatgcactcc agcctctgta ctcatctaag ctgcttattt    2040
ttgatatttg tgtcagtctg taaatggata cttcacttta ataactgttg cttagtaatt    2100
ggctttgtag agaagctgga aaaaaatggt tttgtcttca actcctttgc atgccaggcg    2160
gtgatgtgga tctcggcttc tgtgagcctg tgctgtgggc agggctgagc tggagccgcc    2220
cctctcagcc cgcctgccac ggcctttcct taaaggccat ccttaaaacc agaccctcat    2280
ggctaccagc acctgaaagc ttcctcgaca tctgttaata aagccgtagg cccttgtcta    2340
agtgcaaccg cctagacttt cttcagata catgtccaca tgtccatttt tcaggttctc    2400
taagttggag tggagtctgg aagggttgt gaatgaggct tctgggctat gggtgaggtt    2460
ccaatggcag gttagagccc ctcgggccaa ctgccatcct ggaaagtaga cacagcagtg    2520
cccgctgccc agaagagacc agcaagccaa actggagccc ccattgcagg ctgtcgccat    2580 gtggaaaagag taactcacaa ttgccaataa agtctcatgt ggttttatct aaaaaaaaaa    2640
aaaaaaaaaa aaaaa                                                    2655

<210> SEQ ID NO 6
<211> LENGTH: 1681
<212> TYPE: DNA
<213> ORGANISM: Homo sapiens

<400> SEQUENCE: 6
ttttgtctgt cctggattgg agccgtccct ataaccatct agttccgagt acaaactgga     60
gacagaaata aatattaaag aaatcataga ccgaccaggt aaaggcaaag ggatgaattc    120
ctacttcact aacccttcct tatcctgcca cctcgccggg ggccaggacg tcctccccaa    180
cgtcgccctc aattccaccg cctatgatcc agtgaggcat ttctcgacct atggagcggc    240
cgttgcccag aaccggatct actcgactcc cttttattcg ccacaggaga atgtcgtgtt    300
cagttccagc cgggggccgt atgactatgg atctaattcc ttttaccagg agaaagacat    360
gctctcaaac tgcagacaaa acaccttagg acataacaca cagacctcaa tcgctcagga    420
ttttagttct gagcagggca ggactgcgcc ccaggaccag aaagccagta tccagattta    480
cccctggatg cagcgaatga attcgcacag tggggtcggc tacggagcgg accggaggcg    540
cggccgccag atctactcgc ggtaccagac cctggaactg gagaaggaat tcacttcaa    600 tcgctaccta acgcggcgcc ggcgcatcga gatcgccaac gcgctttgcc tgaccgagcg    660
acagatcaaa atctggttcc agaaccgccg gatgaagtgg aaaaaagaat ctaatctcac    720
atccactctc tcgggggggcg gcggagggggc caccgccgac agcctgggcg aaaagagga    780 aaagcgggaa gagacagaag aggagaagca gaaagagtga ccaggactgt ccctgccacc    840
```

```
cctctctccc tttctccctc gctccccacc aactctcccc taatcacaca ctctgtattt      900
atcactggca caattgatgt gttttgattc cctaaaacaa aattagggag tcaaacgtgg      960
acctgaaagt cagctctgga ccccctccct caccgcacaa ctctctttca ccacgcgcct     1020
cctcctcctc gctcccttgc tagctcgttc tcggcttgtc tacaggccct tttccccgtc     1080
caggccttgg gggctcggac cctgaactca gactctacag attgccctcc aagtgaggac     1140
ttggctcccc cactccttcg acgccccac ccccgccccc cgtgcagaga gccggctcct      1200
gggcctgctg gggcctctgc tccagggcct cagggcccgg cctggcagcc ggggagggcc     1260
ggaggcccaa ggagggcgcg ccttggcccc acaccaaccc ccagggcctc cccgcagtcc     1320
ctgcctagcc cctctgcccc agcaaatgcc cagcccaggc aaattgtatt taaagaatcc     1380
tgggggtcat tatggcattt tacaaactgt gaccgtttct gtgtgaagat ttttagctgt     1440
atttgtggtc tctgtattta tatttatgtt tagcaccgtc agtgttccta tccaatttca     1500
aaaaaggaaa aaaagagggg aaaattacaa aagagagaa aaaaagtgaa tgacgtttgt      1560
ttagccagta ggagaaaata aataaataaa taaatcccct cgtgttaccc tcctgtataa     1620
atccaacctc tgggtccgtt ctcgaatatt taataaaact gatattattt ttaaaacttt     1680
a                                                                    1681

<210> SEQ ID NO 7
<211> LENGTH: 3012
<212> TYPE: DNA
<213> ORGANISM: Homo sapiens

<400> SEQUENCE: 7
aaaaatgcat aaagagccaa gtgcttatat tctggccaag ttatgaggct ctgagaacaa       60
gagcttgagg ggaagactgt taaccccatc cacgccacca gaattagctc tttccctttt      120
ggtttgcaag cactgcctgt aaagccctcg catgagaggc cagcctgcta gggaaatcca      180
ggaatctgca acaaaaacga tgacagtctg aaatactctc tggtgccaac ctccaaattc      240
tcgtctgtca cttcagaccc ccactagttg acagagcagc agaatttcaa ctccagtaga      300
cttgaatatg cctctgggca agaagcagaa gctaacgagg aaagggatttt aaagagtttt     360 tcttgggtgt ttgtcaaact tttattccct gtctgtgtgc agaggggatt caacttcaat      420
ttttctgcag tggctctggg tccagcccct tacttaaagg ccataagatg ttttattgaa      480
agaaactttc aatatcaagt aatccaacca accttctaag ataagccttt tccttcaaca      540
caaagaagtg cattttgcca aatctggaaa gcatgagagc tgggcttttt ttcctatgtc      600
tcttgggaac tgcagctgca atcccgacaa atgcaagatt attatctgat cattccaaac      660
caactgctga acggtagca cctgacaaca ctgcaatccc cagtttaagg gctgaagctg       720
aagaaaatga aaagaaaca gcagtatcca cagaagacga ttcccaccat aaggctgaaa       780
aatcatcagt actaaagtca aaagaggaaa gccatgaaca gtcagcagaa cagggcaaga      840
gttctagcca agagctggga ttgaaggatc aagaggacag tgatggtcac ttaagtgtga      900
atttggagta tgcaccaact gaaggtacat tggacataaa agaagatatg agtgagcctc      960
aggagaaaaa actctcagag aacactgatt ttttggctcc tggtgttagt tccttcacag     1020
attctaacca acaagaaagt atcacaaaga gagggaaaa ccaagaacaa cctagaaatt      1080
attcacatca tcagttgaac aggagcagta aacatagcca aggcctaagg gatcaaggaa     1140
accaagagca ggatccaaat atttccaatg gagaagagga agaagaaaaa gagccaggtg     1200
```

| | |
|---|---|
| aagttggtac ccacaatgat aaccaagaaa gaaagacaga attgcccagg gagcatgcta | 1260 |
| acagcaagca ggaggaagac aatacccaat ctgatgatat tttggaagag tctgatcaac | 1320 |
| caactcaagt aagcaagatg caggaggatg aatttgatca gggtaaccaa gaacaagaag | 1380 |
| ataactccaa tgcagaaatg gaagaggaaa atgcatcgaa cgtcaataag cacattcaag | 1440 |
| aaactgaatg gcagagtcaa gagggtaaaa ctggcctaga agctatcagc aaccacaaag | 1500 |
| agacagaaga aaagactgtt tctgaggctc tgctcatgga acctactgat gatggtaata | 1560 |
| ccacgcccag aaatcatgga gttgatgatg atggcgatga tgatggcgat gatggcggca | 1620 |
| ctgatggccc caggcacagt gcaagtgatg actacttcat cccaagccag gcctttctgg | 1680 |
| aggccgagag agctcaatcc attgcctatc acctcaaaat tgaggagcaa agagaaaaag | 1740 |
| tacatgaaaa tgaaaatata ggtaccactg agcctggaga gcaccaagag gccaagaaag | 1800 |
| cagagaactc atcaaatgag gaggaaacgt caagtgaagg caacatgagg gtgcatgctg | 1860 |
| tggattcttg catgagcttc cagtgtaaaa gaggccacat ctgtaaggca gaccaacagg | 1920 |
| gaaaacctca ctgtgtctgc caggatccag tgacttgtcc tccaacaaaa ccccttgatc | 1980 |
| aagtttgtgg cactgacaat cagacctatg ctagttcctg tcatctattc gctactaaat | 2040 |
| gcagactgga ggggaccaaa aagggcatc aactccagct ggattatttt ggagcctgca | 2100 |
| aatctattcc tacttgtacg gactttgaag tgattcagtt tcctctacgg atgagagact | 2160 |
| ggctcaagaa tatcctcatg cagctttatg aagccaactc tgaacacgct ggttatctaa | 2220 |
| atgagaagca gagaaataaa gtcaagaaaa tttacctgga tgaaagagg cttttggctg | 2280 |
| gggaccatcc cattgatctt ctcttaaggg actttaagaa aaactaccac atgtatgtgt | 2340 |
| atcctgtgca ctggcagttt agtgaacttg accacacccc tatggataga gtcttgacac | 2400 |
| attctgaact tgctcctctg cgagcatctc tggtgcccat ggaacactgc ataacccgtt | 2460 |
| tctttgagga gtgtgacccc aacaaggata gcacatcac cctgaaggag tggggccact | 2520 |
| gctttggaat taaagaagag gacatagatg aaaatctctt gttttgaacg aagattttaa | 2580 |
| agaactcaac tttccagcat cctcctctgt tctaaccact tcagaaatat atgcagctgt | 2640 |
| gatacttgta gatttatatt tagcaaaatg ttagcatgta tgacaagaca atgagagtaa | 2700 |
| ttgcttgaca acaacctatg caccaggtat ttaacattaa ctttggaaac aaaaatgtac | 2760 |
| aattaagtaa agtcaacata tgcaaaatac tgtacattgt gaacagaagt ttaattcata | 2820 |
| gtaatttcac tctctgcatt gacttatgag ataattaatg attaaactat taatgataaa | 2880 |
| aataatgcat ttgtattgtt cataatatca tgtgcacttc aagaaaatgg aatgctactc | 2940 |
| ttttgtggtt tacgtgtatt attttcaata tcttaatacc ctaataaaga gtccataaaa | 3000 |
| atccaaatgc tt | 3012 |

<210> SEQ ID NO 8
<211> LENGTH: 300
<212> TYPE: DNA
<213> ORGANISM: Homo sapiens

<400> SEQUENCE: 8

| | |
|---|---|
| ttgtcttcct caccctgtcc gtgacgtgga ttggtgctgc acccctcatc ctgtctcgga | 60 |
| ttgtgggagg ctgggagtgc gagaagcatt cccaaccctg gcaggtgctt gtggcctctc | 120 |
| gtggcagggc agtctgcggc ggtgttctgg tgcaccccca gtgggtcctc acagctgccc | 180 |
| actgcatcag gaacaaaagc gtgatcttgc tgggtcggca cagcctgttt catcctgaag | 240 |
| acacaggcca ggtatttcag gtcagccaca gcttcccaca cccgctctac gatatgagcc | 300 |

<210> SEQ ID NO 9
<211> LENGTH: 586
<212> TYPE: RNA
<213> ORGANISM: Homo sapiens

<400> SEQUENCE: 9

```
gggagacgaa gggccccaga gcagccgagc ggccgccagg gaggaacgca gaacgcccaa      60
agaggacagg cacaccagcc ccaaaaccac acacacagga agcacaaaag gaagcacaga     120
gacccgggag aaagcccggc ccggggggga ggcgcacgcc caccggacac ggaagcagcg     180 gccgagaaa gagcggacca ccggggcgac acacaaacgg aaagcagaag acgggcccag     240
ccgggaacgc agcgcaaccc gacaaagcaa gaaacgacac caaaccaacg cgaaacggag     300
caccaggccc agaaacggac gaggacagca ccaagggcaa gacgaagacc aagaacgaaa     360
aggaagccac aaaccgaaac acagggcagg gacaggcaaa aggaccaccg caccacacaa     420
gaacggcccc ggagggcgcg ccgcaccccg gagcggaggc cgaggcggcc accacgcccc     480
acgagaacga gccagacgac cgcggccgca agcggaccga accgggaaag accgccacaa     540
ccacacaaca acgagccgga agcaaaagga aagccggggg ccaaga                   586
```

<210> SEQ ID NO 10
<211> LENGTH: 19
<212> TYPE: DNA
<213> ORGANISM: Artificial Sequence
<220> FEATURE:
<223> OTHER INFORMATION: Chemically synthesized primer sequence

<400> SEQUENCE: 10

```
ccacctggac atctggaag                                                  19
```

<210> SEQ ID NO 11
<211> LENGTH: 18
<212> TYPE: DNA
<213> ORGANISM: Artificial Sequence
<220> FEATURE:
<223> OTHER INFORMATION: Chemically synthesized primer sequence

<400> SEQUENCE: 11

```
aatcgcccca ggtgaagt                                                   18
```

<210> SEQ ID NO 12
<211> LENGTH: 19
<212> TYPE: DNA
<213> ORGANISM: Artificial Sequence
<220> FEATURE:
<223> OTHER INFORMATION: Chemically synthesized probe sequence
<220> FEATURE:
<221> NAME/KEY: misc_feature
<222> LOCATION: (1)..(1)
<223> OTHER INFORMATION: conjugated to 5' 6-FAM
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (19)..(19)
<223> OTHER INFORMATION: conjugated to 3' Iowa Black(r) FQ

<400> SEQUENCE: 12

```
cggcctggat gaaagagcg                                                  19
```

<210> SEQ ID NO 13

```
<211> LENGTH: 25
<212> TYPE: DNA
<213> ORGANISM: Artificial Sequence
<220> FEATURE:
<223> OTHER INFORMATION: Chemically synthesized primer sequence

<400> SEQUENCE: 13
gcgtcctcag ttagatcctt atcag                                          25

<210> SEQ ID NO 14
<211> LENGTH: 18
<212> TYPE: DNA
<213> ORGANISM: Artificial Sequence
<220> FEATURE:
<223> OTHER INFORMATION: Chemically synthesized primer sequence

<400> SEQUENCE: 14
ctggccactg cctggatt                                                  18

<210> SEQ ID NO 15
<211> LENGTH: 26
<212> TYPE: DNA
<213> ORGANISM: Artificial Sequence
<220> FEATURE:
<223> OTHER INFORMATION: Chemically synthesized probe sequence
<220> FEATURE:
<221> NAME/KEY: misc_feature
<222> LOCATION: (1)..(1)
<223> OTHER INFORMATION: conjugated to 5' 6-FAM
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (26)..(26)
<223> OTHER INFORMATION: conjugated to 3' Iowa Black(r) FQ

<400> SEQUENCE: 15
cttggaccaa caagtagccg ccttgc                                         26

<210> SEQ ID NO 16
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 16
gcacatttcc agccccttta                                                20

<210> SEQ ID NO 17
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 17
ggcatttctc ccagggatct                                                20

<210> SEQ ID NO 18
<211> LENGTH: 24
<212> TYPE: DNA
<213> ORGANISM: Artificial Sequence
<220> FEATURE:
<223> OTHER INFORMATION: Chemically synthesized probe sequence
<220> FEATURE:
<221> NAME/KEY: misc_feature
```

```
<222> LOCATION: (1)..(1)
<223> OTHER INFORMATION: conjugated to 5' 6-FAM
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (24)..(24)
<223> OTHER INFORMATION: conjugated to 3' Iowa Black(r) FQ

<400> SEQUENCE: 18
cacacaggaa gcacaaaagg aagc                                        24

<210> SEQ ID NO 19
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 19
aacggttctt gtgacccatc                                             20

<210> SEQ ID NO 20
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 20
cgaacaaaag ctcgttcctc                                             20

<210> SEQ ID NO 21
<211> LENGTH: 21
<212> TYPE: DNA
<213> ORGANISM: Artificial Sequence
<220> FEATURE:
<223> OTHER INFORMATION: Chemically synthesized probe sequence
<220> FEATURE:
<221> NAME/KEY: misc_feature
<222> LOCATION: (1)..(1)
<223> OTHER INFORMATION: conjugated to 5' 6-FAM
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (21)..(21)
<223> OTHER INFORMATION: conjugated to 3' Iowa Black(r) FQ

<400> SEQUENCE: 21
cgccaggcat atgctgacgt g                                           21

<210> SEQ ID NO 22
<211> LENGTH: 18
<212> TYPE: DNA
<213> ORGANISM: Artificial Sequence
<220> FEATURE:
<223> OTHER INFORMATION: Chemically synthesized primer sequence

<400> SEQUENCE: 22
cctgtccgtg acgtggat                                               18

<210> SEQ ID NO 23
<211> LENGTH: 19
<212> TYPE: DNA
```

```
<213> ORGANISM: Artificial Sequence
<220> FEATURE:
<223> OTHER INFORMATION: Chemically synthesized primer sequence

<400> SEQUENCE: 23
cagggttggg aatgcttct                                                    19

<210> SEQ ID NO 24
<211> LENGTH: 20
<212> TYPE: DNA
<213> ORGANISM: Artificial Sequence
<220> FEATURE:
<223> OTHER INFORMATION: Chemically synthesized probe sequence
<220> FEATURE:
<221> NAME/KEY: misc_feature
<222> LOCATION: (1)..(1)
<223> OTHER INFORMATION: conjugated to 5' 6-FAM
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (20)..(20)
<223> OTHER INFORMATION: conjugated to 3' Iowa Black(r) FQ

<400> SEQUENCE: 24
cggattgtgg gaggctggga                                                   20

<210> SEQ ID NO 25
<211> LENGTH: 16
<212> TYPE: DNA
<213> ORGANISM: Artificial Sequence
<220> FEATURE:
<223> OTHER INFORMATION: Chemically synthesized primer sequence

<400> SEQUENCE: 25
gcctggagcg cggcag                                                       16

<210> SEQ ID NO 26
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 26
gcacactcaa acaacgactg                                                   20

<210> SEQ ID NO 27
<211> LENGTH: 25
<212> TYPE: DNA
<213> ORGANISM: Artificial Sequence
<220> FEATURE:
<223> OTHER INFORMATION: Chemically synthesized probe sequence
<220> FEATURE:
<221> NAME/KEY: misc_feature
<222> LOCATION: (1)..(1)
<223> OTHER INFORMATION: conjugated to 5' 6-FAM
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (25)..(25)
<223> OTHER INFORMATION: conjugated to 3' Iowa Black(r) FQ

<400> SEQUENCE: 27
agccttatca gttgtgagtg aggac                                             25
```

```
<210> SEQ ID NO 28
<211> LENGTH: 15
<212> TYPE: DNA
<213> ORGANISM: Artificial Sequence
<220> FEATURE:
<223> OTHER INFORMATION: Chemically synthesized primer sequence

<400> SEQUENCE: 28
gccgcggtgt catgg                                                15

<210> SEQ ID NO 29
<211> LENGTH: 19
<212> TYPE: DNA
<213> ORGANISM: Artificial Sequence
<220> FEATURE:
<223> OTHER INFORMATION: Chemically synthesized primer sequence

<400> SEQUENCE: 29
tttcccgctg cagaatctc                                            19

<210> SEQ ID NO 30
<211> LENGTH: 20
<212> TYPE: DNA
<213> ORGANISM: Artificial Sequence
<220> FEATURE:
<223> OTHER INFORMATION: Chemically synthesized probe sequence
<220> FEATURE:
<221> NAME/KEY: misc_feature
<222> LOCATION: (1)..(1)
<223> OTHER INFORMATION: conjugated to 5' 6-FAM
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (9)..(10)
<223> OTHER INFORMATION: internal ZEN quencher

<400> SEQUENCE: 30
agaaactcca gctgggccca                                           20

<210> SEQ ID NO 31
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 31
ggaccaccgc atctctacat                                           20

<210> SEQ ID NO 32
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 32
gtctggctcg ttctcagtgg                                           20

<210> SEQ ID NO 33
<211> LENGTH: 20
<212> TYPE: DNA
<213> ORGANISM: Artificial Sequence
<220> FEATURE:
```

```
<223> OTHER INFORMATION: Chemically synthesized probe sequence
<220> FEATURE:
<221> NAME/KEY: misc_feature
<222> LOCATION: (1)..(1)
<223> OTHER INFORMATION: conjugated to 5' 6-FAM
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (20)..(20)
<223> OTHER INFORMATION: conjugated to 3' Iowa Black(r) FQ

<400> SEQUENCE: 33
cttcttggag ggctgcgcct                                            20

<210> SEQ ID NO 34
<211> LENGTH: 21
<212> TYPE: DNA
<213> ORGANISM: Artificial Sequence
<220> FEATURE:
<223> OTHER INFORMATION: Chemically synthesized primer sequence

<400> SEQUENCE: 34
tctggaaagc atgaagactg g                                          21

<210> SEQ ID NO 35
<211> LENGTH: 20
<212> TYPE: DNA
<213> ORGANISM: Artificial Sequence
<220> FEATURE:
<223> OTHER INFORMATION: Chemically synthesized primer sequence

<400> SEQUENCE: 35
tgctaccgtt tcagcagttg                                            20

<210> SEQ ID NO 36
<211> LENGTH: 20
<212> TYPE: DNA
<213> ORGANISM: Artificial Sequence
<220> FEATURE:
<223> OTHER INFORMATION: Chemically synthesized probe sequence
<220> FEATURE:
<221> NAME/KEY: misc_feature
<222> LOCATION: (1)..(1)
<223> OTHER INFORMATION: conjugated to 5' 6-FAM
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (20)..(20)
<223> OTHER INFORMATION: conjugated to 3' Iowa Black(r) FQ

<400> SEQUENCE: 36
ctgcagctgc aatcccgaca                                            20

<210> SEQ ID NO 37
<211> LENGTH: 3191
<212> TYPE: DNA
<213> ORGANISM: Homo sapiens

<400> SEQUENCE: 37
ggggcgtggc gccggggatt gggagggctt cttgcaggct gctgggctgg ggctaagggc    60
tgctcagttt ccttcagcgg ggcactggga agcgccatgg cactgcaggg catctcggtc   120
gtggagctgt ccggcctggc cccgggcccg ttctgtgcta tggtcctggc tgacttcggg   180
```

```
gcgcgtgtgg tacgcgtgga ccggcccggc tcccgctacg acgtgagccg cttgggccgg      240
ggcaagcgct cgctagtgct ggacctgaag cagccgcggg gagccgccgt gctgcggcgt      300
ctgtgcaagc ggtcggatgt gctgctggag cccttccgcc gcggtgtcat ggagaaactc      360
cagctgggcc cagagattct gcagcgggaa atccaaggc ttatttatgc caggctgagt       420
ggatttggcc agtcaggaag cttctgccgg ttagctggcc acgatatcaa ctatttggct      480
ttgtcaggtg aaggaacag catatttaag ttcttttctg tggaaaactc agaaattgag       540
tctgtgggaa gcacctcgag gacagaacat gttggatggt ggagcacctt tctatacgac     600
ttacaggaca gcagatgggg aattcatggc tgttggagca atagaacccc agttctacga     660
gctgctgatc aaaggacttg gactaaagtc tgatgaactt cccaatcaga tgagcatgga    720
tgattggcca gaaatgaaga agaagtttgc agatgtattt gcagagaaga cgaaggcaga    780
gtggtgtcaa atctttgacg gcacagatgc ctgtgtgact ccggttctga cttttgagga    840
ggttgttcat catgatcaca acaaggaacg gggctcgttt atcaccagtg aggagcagga   900
cgtgagcccc cgccctgcac ctctgctgtt aaacaccca gccatccctt ctttcaaaag     960 ggatccttc ataggagaac acactgagga gatacttgaa gaatttggat tcagccgcga    1020
agagatttat cagcttaact cagataaaat cattgaaagt aataaggtaa aagctagtct    1080
ctaacttcca ggcccacggc tcaagtgaat ttgaatactg catttacagt gtagagtaac    1140
acataacatt gtatgcatgg aaacatggag gaacagtatt acagtgtcct accactctaa    1200
tcaagaaaag aattcagac tctgattcta cagtgatgat tgaattctaa aaatggttat     1260 cattgggct tttgatttat aaaactttgg gtacttatac taaattatgg tagttattct     1320
gccttccagt ttgcttgata tatttgttga tattaagatt cttgacttat attttgaatg    1380
ggttctagtg aaaaaggaat gatatattct tgaagacatc gatatacatt tatttacact    1440
cttgattcta caatgtagaa aatgaggaaa tgccacaaat tgtatggtga taaaagtcac     1500
gtgaaacaga gtgattggtt gcatccaggc cttttgtctt ggtgttcatg atctccctct    1560
aagcacattc caaactttag caacagttat cacactttgt aatttgcaaa gaaagtttc     1620 acctgtattg aatcagaatg ccttcaactg aaaaaaacat atccaaaata atgaggaaat    1680
gtgttggctc actacgtaga gtccagaggg acagtcagtt ttaggggttgc ctgtatccag    1740 taactcgggg cctgtttccc cgtgggtctc tgggctgtca gctttccttt ctccatgtgt    1800
ttgatttctc ctcaggctgg tagcaagttc tggatcttat acccaacaca cagcaacatc    1860
cagaaataaa gatctcagga cccccagca agtcgtttg tgtctccttg gactgagtta       1920
agttacaagc ctttcttata cctgtctttg acaagaaga cgggattgtc tttacataaa      1980
accagcctgc tcctggagct tccctggact caacttccta aaggcatgtg aggaaggggt    2040
agattccaca atctaatccg ggtgccatca gagtagaggg agtagagaat ggatgttggg     2100
taggccatca ataaggtcca ttctgcgcag tatctcaact gccgttcaac aatcgcaaga   2160
ggaaggtgga gcaggtttct tcatcttaca gttgagaaaa cagagactca aagggcttc     2220 ttagttcatg tttcccttag cgcctcagtg atttttttcat ggtggcttag gccaaaagaa    2280
atatctaacc attcaattta taataatta ggtccccaac gaattaaata ttatgtccta     2340
ccaacttatt agctgcttga aaatataat acacataaat aaaaaaatat atttttcatt     2400
tctatttcat tgttaatcac aactactac taaggagatg tatgcaccta ttggacactg    2460
tgcaacttct cacctggaat gagattggac actgctgccc tcatttctg ctccatgttg     2520
```

| | |
|---|---|
| gtgtccatat agtacttgat tttttatcag atggcctgga aaacccagtc tcacaaaaat | 2580 |
| atgaaattat cagaaggatt atagtgcaat cttatgttga agaatgaac tacctcacta | 2640 |
| gtagttcacg tgatgtctga cagatgttga gtttcattgt gtttgtgtgt tcaaatttt | 2700 |
| aaatattctg agatactctt gtgaggtcac tctaatgccc tgggtgcctt ggcacagttt | 2760 |
| tagaaatacc agttgaaaat atttgctcag gaatatgcaa ctaggaaggg gcagaatcag | 2820 |
| aatttaagct ttcatattct agccttcagt cttgttcttc aaccatttt aggaactttc | 2880 |
| ccataaggtt atgttttcca gcccaggcat ggaggatcac ttgaggccaa gagttcgaga | 2940 |
| ccagcctggg gaacttggct ggacctccgt ttctacgaaa taaaaataaa aaaattatcc | 3000 |
| aggtatggtg gtgtgtgcct gtagtcctat ctactcaagg gtggggcagg aggatcactt | 3060 |
| gagcccagga atttgaggcc acagtgaatt aggattgcac cactgcactc tagcccaggc | 3120 |
| aacagaacaa gaacctgtct ctaaataaat aaataaaaat aataataata aaaagatgt | 3180 |
| tttccctaca a | 3191 |

<210> SEQ ID NO 38
<211> LENGTH: 2603
<212> TYPE: DNA
<213> ORGANISM: Homo sapiens

<400> SEQUENCE: 38

| | |
|---|---|
| ggggcgtggc gccggggatt gggagggctt cttgcaggct gctgggctgg ggctaagggc | 60 |
| tgctcagttt ccttcagcgg ggcactggga agcgccatgg cactgcaggg catctcggtc | 120 |
| gtggagctgt ccggcctggc cccgggcccg ttctgtgcta tggtcctggc tgacttcggg | 180 |
| gcgcgtgtgg tacgcgtgga ccggcccggc tcccgctacg acgtgagccg cttgggccgg | 240 |
| ggcaagcgct cgctagtgct ggacctgaag cagccgcggg gagccgccgt gctgcggcgt | 300 |
| ctgtgcaagc ggtcggatgt gctgctggag cccttccgcc gcggtgtcat ggagaaactc | 360 |
| cagctgggcc cagagattct gcagcgggaa atccaaggc ttatttatgc caggctgagt | 420 |
| ggatttggcc agtcaggaag cttctgccgg ttagctggcc acgatatcaa ctatttggct | 480 |
| ttgtcaggtt ttctctcaaa aattggcaga agtggtgaga atccgtatgc cccgctgaat | 540 |
| ctcctggctg actttgctgg tggtggcctt atgtgtgcac tgggcattat aatggctctt | 600 |
| tttgaccgca cacgcactgg caagggtcag gtcattgatg caaatatggt ggaaggaaca | 660 |
| gcatatttaa gttctttct gtggaaaact cagaaattga gtctgtggga agcacctcga | 720 |
| ggacagaaca tgttggatgg tggagcaccct ttctatacga cttacaggac agcagatggg | 780 |
| gaattcatgg ctgttggagc aatagaaccc cagttctacg agctgctgat caaaggactt | 840 |
| ggactaaagt ctgatgaact tcccaatcag atgagcatgg atgattggcc agaaatgaag | 900 |
| aagaagtttg cagatgtatt tgcagagaag acgaaggcag agtggtgtca aatctttgac | 960 |
| ggcacagatg cctgtgtgac tccggttctg acttttgagg aggttgttca tcatgatcac | 1020 |
| aacaaggaac ggggctcgtt tatcaccagt gaggagcagg acgtgagccc ccgccctgca | 1080 |
| cctctgctgt taaacacccc agccatccct tctttcaaaa gggatccttt cataggagaa | 1140 |
| cacactgagg agatacttga agaatttgga ttcagccgcg aagagattta tcagcttaac | 1200 |
| tcagataaaa tcattgaaag taataaggct ggtagcaagt tctggatctt atacccaaca | 1260 |
| cacagcaaca tccagaaaata aagatctcag gaccccccag caagtcgttt tgtgtctcct | 1320 |
| tggactgagt taagttacaa gccttttctta tacctgtctt tgacaaagaa gacgggattg | 1380 |
| tcttttacata aaaccagcct gctcctggag cttccctgga ctcaacttcc taaaggcatg | 1440 |

```
tgaggaaggg gtagattcca caatctaatc cgggtgccat cagagtagag ggagtagaga     1500
atggatgttg ggtaggccat caataaggtc cattctgcgc agtatctcaa ctgccgttca     1560
acaatcgcaa gaggaaggtg gagcaggttt cttcatctta cagttgagaa aacagagact     1620
cagaagggct tcttagttca tgtttccctt agcgcctcag tgattttttc atggtggctt     1680
aggccaaaag aaatatctaa ccattcaatt tataaataat taggtcccca acgaattaaa     1740
tattatgtcc taccaactta ttagctgctt gaaaaatata atacacataa ataaaaaaat     1800
atatttttca tttctatttc attgttaatc acaactactt actaaggaga tgtatgcacc     1860
tattggacac tgtgcaactt ctcacctgga atgagattgg acactgctgc cctcattttc     1920
tgctccatgt tggtgtccat atagtacttg attttttatc agatggcctg gaaaacccag     1980
tctcacaaaa atatgaaatt atcagaagga ttatagtgca atcttatgtt gaaagaatga     2040
actacctcac tagtagttca cgtgatgtct gacagatgtt gagtttcatt gtgtttgtgt     2100
gttcaaattt ttaaatattc tgagatactc ttgtgaggtc actctaatgc cctgggtgcc     2160
ttggcacagt tttagaaata ccagttgaaa atatttgctc aggaatatgc aactaggaag     2220
gggcagaatc agaatttaag ctttcatatt ctagccttca gtcttgttct tcaaccattt     2280
ttaggaactt tcccataagg ttatgttttc cagcccaggc atggaggatc acttgaggcc     2340
aagagttcga gaccagcctg ggaacttgg ctggacctcc gtttctacga aataaaaata     2400
aaaaaattat ccaggtatgg tggtgtgtgc ctgtagtcct atctactcaa gggtggggca     2460
ggaggatcac ttgagcccag gaatttgagg ccacagtgaa ttaggattgc accactgcac     2520
tctagcccag gcaacagaac aagaacctgt ctctaaataa ataaataaaa ataataataa     2580
taaaaaagat gttttcccta caa                                            2603

<210> SEQ ID NO 39
<211> LENGTH: 2537
<212> TYPE: DNA
<213> ORGANISM: Homo sapiens

<400> SEQUENCE: 39
cccagaaggc cgcgggggt ggaccgccta agagggcgtg cgctcccgac atgccccgcg       60
gcgcgccatt aaccgccaga tttgaatcgc gggacccgtt ggcagaggtg gcggcggcgg     120
catgggtgcc ccgacgttgc cccctgcctg gcagcccttt ctcaaggacc accgcatctc     180
tacattcaag aactggccct tcttggaggg ctgcgcctgc accccggagc ggatggccga     240
ggctggcttc atccactgcc ccactgagaa cgagccagac ttggcccagt gtttcttctg     300
cttcaaggag ctggaaggct gggagccaga tgacgacccc atgcaaagga aaccaacaat     360
aagaagaaag aatttgagga aactgcggag aaagtgcgcc gtgccatcga gcagctggct     420
gccatggatt gaggcctctg gccggagctg cctggtccca gagtggctgc accacttcca     480
gggtttattc cctggtgcca ccagccttcc tgtgggcccc ttagcaatgt cttaggaaag     540
gagatcaaca ttttcaaatt agatgtttca actgtgctct tgttttgtct tgaaagtggc     600
accagaggtg cttctgcctg tgcagcgggt gctgctggta acagtggctg cttctctctc     660
tctctctctt ttttggggc tcattttttgc tgttttgatt cccgggctta ccaggtgaga     720
agtgagggag gaagaaggca gtgtcccttt tgctagagct gacagctttg ttcgcgtggg     780
cagagccttc cacagtgaat gtgtctggac ctcatgttgt tgaggctgtc acagtcctga     840
gtgtggactt ggcaggtgcc tgttgaatct gagctgcagg ttccttatct gtcacacctg     900
```

```
tgcctcctca gaggacagtt tttttgttgt tgtgttttt tgtttttttt tttttggtag    960
atgcatgact tgtgtgtgat gagagaatgg agacagagtc cctggctcct ctactgttta   1020
acaacatggc tttcttattt tgtttgaatt gttaattcac agaatagcac aaactacaat   1080
taaaactaag cacaaagcca ttctaagtca ttggggaaac ggggtgaact tcaggtggat   1140
gaggagacag aatagagtga taggaagcgt ctggcagata ctccttttgc cactgctgtg   1200
tgattagaca ggcccagtga gccgcggggc acatgctggc cgctcctccc tcagaaaaag   1260
gcagtggcct aaatcctttt taaatgactt ggctcgatgc tgtggggac tggctgggct    1320
gctgcaggcc gtgtgtctgt cagcccaacc ttcacatctg tcacgttctc cacacgggg    1380
agagacgcag tccgcccagg tccccgcttt ctttggaggc agcagctccc gcagggctga   1440
agtctggcgt aagatgatgg atttgattcg ccctcctccc tgtcatagag ctgcagggtg   1500
gattgttaca gcttcgctgg aaacctctgg aggtcatctc ggctgttcct gagaaataaa   1560
aagcctgtca tttcaaacac tgctgtggac cctactgggt ttttaaaata ttgtcagttt   1620
ttcatcgtcg tccctagcct gccaacagcc atctgcccag acagccgcag tgaggatgag   1680
cgtcctggca gagacgcagt tgtctctggg cgcttgccag agccacgaac cccagacctg   1740
tttgtatcat ccgggctcct tccgggcaga acaactgaa aatgcacttc agacccactt    1800
atttctgcca catctgagtc ggcctgagat agacttttcc ctctaaactg ggagaatatc   1860
acagtggttt ttgttagcag aaaatgcact ccagcctctg tactcatcta agctgcttat   1920
ttttgatatt tgtgtcagtc tgtaaatgga tacttcactt taataactgt tgcttagtaa   1980
ttggctttgt agagaagctg gaaaaaaatg gttttgtctt caactccttt gcatgccagg   2040
cggtgatgtg gatctcggct tctgtgagcc tgtgctgtgg gcagggctga gctggagccg   2100
cccctctcag cccgcctgcc acggccttc cttaaaggcc atccttaaaa ccagaccctc     2160
atggctacca gcacctgaaa gcttcctcga catctgttaa taaagccgta ggcccttgtc   2220
taagtgcaac cgcctagact ttcttcaga tacatgtcca catgtccatt tttcaggttc     2280
tctaagttgg agtggagtct gggaagggtt gtgaatgagg cttctgggct atgggtgagg   2340
ttccaatggc aggttagagc ccctcgggcc aactgccatc ctggaaagta gagacagcag   2400
tgcccgctgc ccagaagaga ccagcaagcc aaactggagc ccccattgca ggctgtcgcc   2460
atgtggaaag agtaactcac aattgccaat aaagtctcat gtggttttat ctaaaaaaaa   2520
aaaaaaaaaa aaaaaaa                                                  2537

<210> SEQ ID NO 40
<211> LENGTH: 2724
<212> TYPE: DNA
<213> ORGANISM: Homo sapiens

<400> SEQUENCE: 40
cccagaaggc cgcgggggt ggaccgccta agagggcgtg cgctcccgac atgccccgcg      60
gcgcgccatt aaccgccaga tttgaatcgc gggacccgtt ggcagaggtg gcggcggcgg    120
catgggtgcc ccgacgttgc cccctgcctg gcagcccttt ctcaaggacc accgcatctc    180
tacattcaag aactggccct tcttggaggg ctgcgcctgc accccggagc ggatggccga    240
ggctggcttc atccactgcc ccactgagaa cgagccagac ttggcccagt gtttcttctg    300
cttcaaggag ctggaaggct gggagccaga tgacgacccc attgggccgg gcacggtggc    360
ttacgcctgt aataccagca ctttgggagg ccgaggcggg cggatcacga gagaggaaca    420
taaaaagcat tcgtccggtt gcgctttcct ttctgtcaag aagcagtttg aagaattaac    480
```

```
ccttggtgaa ttttgaaac tggacagaga aagagccaag aacaaaattg caaaggaaac    540
caacaataag aagaaagaat ttgaggaaac tgcggagaaa gtgcgccgtg ccatcgagca    600
gctggctgcc atggattgag gcctctggcc ggagctgcct ggtcccagag tggctgcacc    660
acttccaggg tttattccct ggtgccacca gccttcctgt gggcccctta gcaatgtctt    720
aggaaaggag atcaacattt tcaaattaga tgtttcaact gtgctcttgt tttgtcttga    780
aagtggcacc agaggtgctt ctgcctgtgc agcgggtgct gctggtaaca gtggctgctt    840
ctctctctct ctctcttttt tgggggctca ttttgctgt tttgattccc gggcttacca     900
ggtgagaagt gagggaggaa gaaggcagtg tcccttttgc tagagctgac agctttgttc    960
gcgtgggcag agccttccac agtgaatgtg tctggacctc atgttgttga ggctgtcaca   1020
gtcctgagtg tggacttggc aggtgcctgt tgaatctgag ctgcaggttc cttatctgtc   1080
acacctgtgc ctcctcagag gacagttttt tgttgttgt gttttttgt tttttttttt     1140 ttggtagatg catgacttgt gtgtgatgag agaatggaga cagagtccct ggctcctcta   1200
ctgtttaaca acatggcttt cttattttgt ttgaattgtt aattcacaga atagcacaaa   1260
ctacaattaa aactaagcac aaagccattc taagtcattg gggaaacggg gtgaacttca   1320
ggtggatgag gagacagaat agagtgatag gaagcgtctg gcagatactc cttttgccac   1380
tgctgtgtga ttagacaggc ccagtgagcc gcggggcaca tgctggccgc tcctccctca   1440 gaaaaggca gtggcctaaa tccttttaa atgacttggc tcgatgctgt gggggactgg      1500
ctgggctgct gcaggccgtg tgtctgtcag cccaaccttc acatctgtca cgttctccac   1560 acggggaga gacgcagtcc gcccaggtcc ccgctttctt tggaggcagc agctcccgca    1620
gggctgaagt ctggcgtaag atgatggatt tgattcgccc tcctccctgt catagagctg   1680
cagggtggat tgttacagct tcgctggaaa cctctggagg tcatctcggc tgttcctgag   1740
aaataaaaag cctgtcattt caaacactgc tgtggaccct actgggtttt taaaatattg   1800 tcagttttc atcgtcgtcc ctagcctgcc aacagccatc tgcccagaca gccgcagtga    1860
ggatgagcgt cctggcagag acgcagttgt ctctgggcgc ttgccagagc cacgaacccc   1920
agacctgttt gtatcatccg ggctccttcc gggcagaaac aactgaaaat gcacttcaga   1980
cccacttatt tctgccacat ctgagtcggc ctgagataga cttttccctc taaactggga   2040
gaatatcaca gtggttttg ttagcagaaa atgcactcca gcctctgtac tcatctaagc    2100
tgcttatttt tgatatttgt gtcagtctgt aaatggatac ttcactttaa taactgttgc   2160
ttagtaattg gctttgtaga gaagctggaa aaaatggtt ttgtcttcaa ctcctttgca    2220
tgccaggcgg tgatgtggat ctcggcttct gtgagcctgt gctgtgggca gggctgagct   2280
ggagccgccc ctctcagccc gcctgccacg gcctttcctt aaaggccatc cttaaaacca   2340
gaccctcatg gctaccagca cctgaaagct tcctcgacat ctgttaataa agccgtaggc   2400
ccttgtctaa gtgcaaccgc ctagactttc tttcagatac atgtccacat gtccattttt   2460
caggttctct aagttggagt ggagtctggg aagggttgtg aatgaggctt ctgggctatg   2520
ggtgaggttc caatggcagg ttagagcccc tcgggccaac tgccatcctg gaaagtagag   2580
acagcagtgc ccgctgccca gaagagacca gcaagccaaa ctggagcccc cattgcaggc   2640
tgtcgccatg tggaaagagt aactcacaat tgccaataaa gtctcatgtg gttttatcta   2700
aaaaaaaaaa aaaaaaaaaa aaaa                                         2724
```

<210> SEQ ID NO 41

<211> LENGTH: 2081
<212> TYPE: DNA
<213> ORGANISM: Homo sapiens

<400> SEQUENCE: 41

```
aactttttat tgtggtttgt ccgttccgag cgctccgcag aacagtcctc cctgtaagag      60
cctaaccatt gccagggaaa cctgccctgg gcgctccctt cattagcagt attttttta     120
aattaatctg attaataatt attttccc catttaattt tttttcctcc caggtggagt     180
tgccgaagct gggggcagct ggggagggtg gggatgggag gggagagaca gaagttgagg     240
gcatctctct cttccttccc gaccctctgg cccccaaggg gcaggaggaa tgcaggagca     300
ggagttgagc ttgggagctg cagatgcctc cgcccctcct ctctcccagg ctcttcctcc     360
tgcccccttc ttgcaactct ccttaatttt gtttggcttt tggatgatta taattatttt     420
tattttgaa tttatataaa gtatatgtgt gtgtgtgtgg agctgagaca ggctcggcag     480
cggcacagaa tgagggaaga cgagaaagag agtgggagag agagaggcag agagggagag     540
agggagagtg acagcagcgc tcggacgtcc tccccaacgt cgccctcaat tccaccgcct     600
atgatccagt gaggcatttc tcgacctatg gagcggccgt tgcccagaac cggatctact     660
cgactccctt ttattcgcca caggagaatg tcgtgttcag ttccagccgg gggccgtatg     720
actatggatc taattccttt taccaggaga aagacatgct ctcaaactgc agacaaaaca     780
ccttaggaca taacacacag acctcaatcg ctcaggattt tagttctgag cagggcagga     840
ctgcgcccca ggaccagaaa gccagtatcc agatttaccc ctggatgcag cgaatgaatt     900
cgcacagtgg ggtcggctac ggagcggacc ggaggcgcgg ccgccagatc tactcgcggt     960
accagaccct ggaactggag aaggaatttc acttcaatcg ctacctaacg cggcgccggc    1020
gcatcgagat cgccaacgcg ctttgcctga ccgagcgaca gatcaaaatc tggttccaga    1080
accgccggat gaagtggaaa aaagaatcta atctcacatc cactctctcg gggggcggcg    1140
gaggggccac cgccgacagc ctgggcggaa aagaggaaaa gcgggaagag acagaagagg    1200
agaagcagaa agagtgacca ggactgtccc tgccacccct ctctcccttt ctccctcgct    1260
ccccaccaac tctcccctaa tcacacactc tgtatttatc actggcacaa ttgatgtgtt    1320
ttgattccct aaaacaaaat tagggagtca aacgtggacc tgaaagtcag ctctggaccc    1380
cctccctcac cgcacaactc tctttcacca cgcgcctcct cctcctcgct cccttgctag    1440
ctcgttctcg gcttgtctac aggcccttttt ccccgtccag gccttggggg ctcggaccct    1500
gaactcagac tctacagatt gccctccaag tgaggacttg gctcccccac tccttcgacg    1560
cccccacccc cgccccccgt gcagagagcc ggctcctggg cctgctgggg cctctgctcc    1620
agggcctcag ggcccggcct ggcagccggg gagggccgga ggcccaagga gggcgcgcct    1680
tggccccaca ccaaccccca gggcctcccc gcagtccctg cctagcccct ctgccccagc    1740
aaatgcccag cccaggcaaa ttgtatttaa agaatcctgg gggtcattat ggcattttac    1800
aaactgtgac cgtttctgtg tgaagatttt tagctgtatt tgtggtctct gtatttatat    1860
ttatgtttag caccgtcagt gttcctatcc aatttcaaaa aaggaaaaaa aagagggaaa    1920
attacaaaaa gagagaaaaa aagtgaatga cgtttgttta gccagtagga gaaaataaat    1980
aaataaataa atcccttcgt gttaccctcc tgtataaatc caacctctgg gtccgttctc    2040
gaatatttaa taaaactgat attattttta aactttaaa a                         2081
```

<210> SEQ ID NO 42
<211> LENGTH: 2910

```
<212> TYPE: DNA
<213> ORGANISM: Homo sapiens

<400> SEQUENCE: 42
aaaaatgcat aaagagccaa gtgcttatat tctggccaag ttatgaggct ctgagaacaa      60
gagcttgagg ggaagactgt taaccccatc cacgccacca gaattagctc tttcccttt     120
ggtttgcaag cactgcctgt aaagccctcg catgagaggc cagcctgcta gggaaatcca    180
ggaatctgca acaaaaacga tgacagtctg aaatactctc tggtgccaac ctccaaattc    240
tcgtctgtca cttcagaccc ccactagttg acagagcagc agaatttcaa ctccagtaga    300
cttgaatatg cctctgggca agaagcagaa gctaacgagg aaagggattt aaagagtttt    360
tcttgggtgt ttgtcaaact tttattccct gtctgtgtgc agaggggatt caacttcaat    420
tttctgcag tggctctggg tccagcccct tacttaaaga tctggaaagc atgaagactg     480
ggctttttt cctatgtctc ttgggaactg cagctgcaat cccgacaaat gcaagattat     540
tatctgatca ttccaaacca actgctgaaa cggtagcacc tgacaacact gcaatcccca    600
gtttaagggc tgaagctgaa gaaaatgaaa agaaacagc agtatccaca gaagacgatt    660
cccaccataa ggctgaaaaa tcatcagtac taaagtcaaa agaggaaagc catgaacagt    720
cagcagaaca gggcaagagt tctagccaag agctgggatt gaaggatcaa gaggacagtg    780
atggtcactt aagtgtgaat ttggagtatg caccaactga aggtacattg gacataaaag    840
aagatatgag tgagcctcag gagaaaaaac tctcagagaa cactgatttt ttggctcctg    900
gtgttagttc cttcacagat tctaaccaac aagaaagtat cacaaagaga gaggaaaacc    960
aagaacaacc tagaaattat tcacatcatc agttgaacag gagcagtaaa catagccaag   1020
gcctaaggga tcaaggaaac caagagcagg atccaaatat ttccaatgga gaagaggaag   1080
aagaaaaaga gccaggtgaa gttggtaccc acaatgataa ccaagaaaga aagacagaat   1140
tgcccaggga gcatgctaac agcaagcagg aggaagacaa tacccaatct gatgatattt   1200
tggaagagtc tgatcaacca actcaagtaa gcaagatgca ggaggatgaa tttgatcagg   1260
gtaaccaaga acaagaagat aactccaatg cagaaatgga agaggaaaat gcatcgaacg   1320
tcaataagca cattcaagaa actgaatggc agagtcaaga gggtaaaact ggcctagaag   1380
ctatcagcaa ccacaaagag acagaagaaa agactgtttc tgaggctctg ctcatggaac   1440
ctactgatga tggtaatacc acgcccagaa atcatggagt tgatgatgat ggcgatgatg   1500
atggcgatga tggcggcact gatggccca ggcacagtgc aagtgatgac tacttcatcc     1560
caagccaggc ctttctggag gccgagagag ctcaatccat tgcctatcac ctcaaaattg   1620
aggagcaaag agaaaagta catgaaaatg aaaatatagg taccactgag cctggagagc    1680
accaagaggc caagaaagca gagaactcat caaatgagga ggaaacgtca agtgaaggca    1740
acatgagggt gcatgctgtg gattcttgca tgagcttcca gtgtaaaaga ggccacatct   1800
gtaaggcaga ccaacaggga aaacctcact gtgtctgcca ggatccagtg acttgtcctc   1860
caacaaaacc ccttgatcaa gtttgtggca ctgacaatca gacctatgct agttcctgtc   1920
atctattcgc tactaaatgc agactggagg ggaccaaaaa ggggcatcaa ctccagctgg   1980
attattttgg agcctgcaaa tctattccta cttgtacgga ctttgaagtg attcagtttc   2040
ctctacggat gagagactgg ctcaagaata tcctcatgca gctttatgaa gccaactctg   2100
aacacgctgg ttatctaaat gagaagcaga gaaataaagt caagaaaatt tacctggatg   2160
aaaagagggct tttggctggg gaccatccca ttgatcttct cttaagggac tttaagaaaa   2220
```

-continued

| | | | | | |
|---|---|---|---|---|---|
| actaccacat | gtatgtgtat | cctgtgcact | ggcagtttag | tgaacttgac | caacaccta | 2280 |
| tggatagagt | cttgacacat | tctgaacttg | ctcctctgcg | agcatctctg | gtgcccatgg | 2340 |
| aacactgcat | aacccgtttc | tttgaggagt | gtgaccccaa | caaggataag | cacatcaccc | 2400 |
| tgaaggagtg | gggccactgc | tttggaatta | aagaagagga | catagatgaa | aatctcttgt | 2460 |
| tttgaacgaa | gattttaaag | aactcaactt | tccagcatcc | tcctctgttc | taaccacttc | 2520 |
| agaaatatat | gcagctgtga | tacttgtaga | tttatattta | gcaaaatgtt | agcatgtatg | 2580 |
| acaagacaat | gagagtaatt | gcttgacaac | aacctatgca | ccaggtattt | aacattaact | 2640 |
| ttggaaacaa | aaatgtacaa | ttaagtaaag | tcaacatatg | caaaatactg | tacattgtga | 2700 |
| acagaagttt | aatttcatagt | aatttcactc | tctgcattga | cttatgagat | aattaatgat | 2760 |
| taaactatta | atgataaaaa | taatgcattt | gtattgttca | taatatcatg | tgcacttcaa | 2820 |
| gaaaatggaa | tgctactctt | ttgtggttta | cgtgtattat | tttcaatatc | ttaataccct | 2880 |
| aataaagagt | ccataaaaat | ccaaatgctt | | | | 2910 |

```
<210> SEQ ID NO 43
<211> LENGTH: 3019
<212> TYPE: DNA
<213> ORGANISM: Homo sapiens

<400> SEQUENCE: 43
```

| | | | | | |
|---|---|---|---|---|---|
| aaaaatgcat | aaagagccaa | gtgcttatat | tctggccaag | ttatgaggct | ctgagaacaa | 60 |
| gagcttgagg | ggaagactgt | taaccccatc | cacgccacca | gaattagctc | tttcccttt | 120 |
| ggtttgcaag | cactgcctgt | aaagccctcg | catgagaggc | cagcctgcta | gggaaatcca | 180 |
| ggaatctgca | acaaaaacga | tgacagtctg | aaatactctc | tggtgccaac | ctccaaattc | 240 |
| tcgtctgtca | cttcagaccc | ccactagttg | acagagcagc | agaatttcaa | ctccagtaga | 300 |
| cttgaatatg | cctctgggca | agaagcaga | gctaacgagg | aaagggattt | aaagagtttt | 360 |
| tcttgggtgt | ttgtcaaact | tttattccct | gtctgtgtgc | agagggggatt | caacttcaat | 420 |
| ttttctgcag | tggctctggg | tccagcccct | tacttaaaga | tctggaaagc | atgaagactg | 480 |
| ggcttttttt | cctatgtctc | ttgggaactg | cagctgcaat | cccggtgaaa | aggagataag | 540 |
| aagcaaagga | gcaaaccaaa | cctaatatga | atcctgtact | ttggccagaa | gccgtggctc | 600 |
| acatctgtaa | tcccagcact | ttgggaggcc | aagacaaatg | caagattatt | atctgatcat | 660 |
| tccaaaccaa | ctgctgaaac | ggtagcacct | gacaacactg | caatccccag | tttaagggct | 720 |
| gaagctgaag | aaaatgaaaa | agaaacagca | gtatccacag | aagacgattc | ccaccataag | 780 |
| gctgaaaaat | catcagtact | aaagtcaaaa | gaggaaagcc | atgaacagtc | agcagaacag | 840 |
| ggcaagagtt | ctagccaaga | gctgggattg | aaggatcaag | aggacagtga | tggtcactta | 900 |
| agtgtgaatt | tggagtatgc | accaactgaa | ggtacattgg | acataaaaga | agatatgagt | 960 |
| gagcctcagg | agaaaaaact | ctcagagaac | actgattttt | tggctcctgg | tgttagttcc | 1020 |
| ttcacagatt | ctaaccaaca | agaaagtatc | acaaagagag | aggaaaacca | agaacaacct | 1080 |
| agaaattatt | cacatcatca | gttgaacagg | agcagtaaac | atagccaagg | cctaagggat | 1140 |
| caaggaaacc | aagagcagga | tccaaatatt | tccaatggag | aagaggaaga | agaaaaagag | 1200 |
| ccaggtgaag | ttggtaccca | caatgataac | caagaaagaa | agacagaatt | gcccagggag | 1260 |
| catgctaaca | gcaagcagga | ggaagacaat | acccaatctg | atgatatttt | ggaagagtct | 1320 |
| gatcaaccaa | ctcaagtaag | caagatgcag | gaggatgaat | ttgatcaggg | taaccaagaa | 1380 |
| caagaagata | actccaatgc | agaaatggaa | gaggaaaatg | catcgaacgt | caataagcac | 1440 |

```
attcaagaaa ctgaatggca gagtcaagag ggtaaaactg gcctagaagc tatcagcaac   1500
cacaaagaga cagaagaaaa gactgtttct gaggctctgc tcatggaacc tactgatgat   1560
ggtaatacca cgcccagaaa tcatggagtt gatgatgatg cgatgatga tggcgatgat    1620 ggcggcactg atggcccag gcacagtgca agtgatgact acttcatccc aagccaggcc    1680
tttctggagg ccgagagagc tcaatccatt gcctatacc tcaaaattga ggagcaaaga    1740 gaaaagtac atgaaaatga aaatataggt accactgagc ctggagagca ccaagaggcc    1800
aagaaagcag agaactcatc aaatgaggag gaaacgtcaa gtgaaggcaa catgagggtg    1860
catgctgtgg attcttgcat gagcttccag tgtaaaagag gccacatctg taaggcagac    1920
caacagggaa aacctcactg tgtctgccag gatccagtga cttgtcctcc aacaaaaccc    1980
cttgatcaag tttgtggcac tgacaatcag acctatgcta gttcctgtca tctattcgct    2040
actaaatgca gactggaggg gaccaaaaag gggcatcaac tccagctgga ttattttgga    2100
gcctgcaaat ctattcctac ttgtacggac tttgaagtga ttcagtttcc tctacggatg    2160
agagactggc tcaagaatat cctcatgcag ctttatgaag ccaactctga cacgctggt    2220 tatctaaatg agaagcagag aaataaagtc aagaaaattt acctggatga aaagaggctt    2280
ttggctgggg accatcccat tgatcttctc ttaagggact ttaagaaaaa ctaccacatg    2340
tatgtgtatc ctgtgcactg gcagtttagt gaacttgacc aacacccat ggatagagtc    2400 ttgacacatt ctgaacttgc tcctctgcga gcatctctgg tgcccatgga acactgcata    2460
acccgtttct ttgaggagtg tgaccccaac aaggataagc acatcaccct gaaggagtgg    2520
ggccactgct ttgaattaa agaagaggac atagatgaaa atctcttgtt ttgaacgaag    2580
attttaaaga actcaacttt ccagcatcct cctctgttct aaccacttca gaaatatatg    2640
cagctgtgat acttgtagat ttatatttag caaaatgtta gcatgtatga caagacaatg    2700
agagtaattg cttgacaaca acctatgcac caggtattta acattaactt tggaaacaaa    2760
aatgtacaat taagtaaagt caacatatgc aaaatactgt acattgtgaa cagaagttta    2820
attcatagta atttcactct ctgcattgac ttatgagata attaatgatt aaactattaa    2880
tgataaaaat aatgcatttg tattgttcat aatatcatgt gcacttcaag aaaatggaat    2940
gctactcttt tgtggtttac gtgtattatt ttcaatatct taatacccta ataaagagtc    3000
cataaaaatc caaatgctt                                                 3019
```

<210> SEQ ID NO 44
<211> LENGTH: 2670
<212> TYPE: DNA
<213> ORGANISM: Homo sapiens

<400> SEQUENCE: 44

```
aaaaatgcat aaagagccaa gtgcttatat tctggccaag ttatgaggct ctgagaacaa     60
gagcttgagg ggaagactgt taaccccatc cacgccacca gaattagctc tttcccttt    120 ggtttgcaag cactgcctgt aaagccctcg catgagaggc cagcctgcta gggaaatcca    180
ggaatctgca acaaaaacga tgacagtctg aaatactctc tggtgccaac ctccaaattc    240
tcgtctgtca cttcagaccc ccactagttg acagagcagc agaatttcaa ctccagtaga    300
cttgaatatg cctctgggca agaagcagaa gctaacgagg aaagggatt aaagagtttt     360 tcttgggtgt ttgtcaaact tttattccct gtctgtgtgc agaggggatt caacttcaat    420
ttttctgcag tggctctggg tccagcccct tacttaaaga tctggaaagc catgaacagt    480
```

```
cagcagaaca gggcaagagt tctagccaag agctgggatt gaaggatcaa gaggacagtg    540
atggtcactt aagtgtgaat ttggagtatg caccaactga aggtacattg acataaaaag    600
aagatatgag tgagcctcag gagaaaaaac tctcagagaa cactgatttt ttggctcctg    660
gtgttagttc cttcacagat tctaaccaac aagaaagtat cacaaagaga gaggaaaacc    720
aagaacaacc tagaaattat tcacatcatc agttgaacag gagcagtaaa catagccaag    780
gcctaaggga tcaaggaaac caagagcagg atccaaatat ttccaatgga gaagaggaag    840
aagaaaaaga gccaggtgaa gttggtaccc acaatgataa ccaagaaaga aagacagaat    900
tgcccaggga gcatgctaac agcaagcagg aggaagacaa tacccaatct gatgatattt    960
tggaagagtc tgatcaacca actcaagtaa gcaagatgca ggaggatgaa tttgatcagg    1020
gtaaccaaga caagaagat aactccaatg cagaaatgga agaggaaaat gcatcgaacg    1080
tcaataagca cattcaagaa actgaatggc agagtcaaga gggtaaaact ggcctagaag    1140
ctatcagcaa ccacaaagag acagaagaaa agactgtttc tgaggctctg ctcatggaac    1200
ctactgatga tggtaatacc acgcccagaa atcatggagt tgatgatgat ggcgatgatg    1260
atggcgatga tggcggcact gatggcccca ggcacagtgc aagtgatgac tacttcatcc    1320
caagccaggc ctttctggag gccgagagag ctcaatccat tgcctatcac ctcaaaattg    1380
aggagcaaag agaaaagta catgaaaatg aaaatatagg taccactgag cctggagagc    1440
accaagaggc caagaaagca gagaactcat caaatgagga ggaaacgtca agtgaaggca    1500
acatgagggt gcatgctgtg gattcttgca tgagcttcca gtgtaaaaga ggccacatct    1560
gtaaggcaga ccaacaggga aaacctcact gtgtctgcca ggatccagtg acttgtcctc    1620
caacaaaacc ccttgatcaa gtttgtggca ctgacaatca gacctatgct agttcctgtc    1680
atctattcgc tactaaatgc agactggagg ggaccaaaaa ggggcatcaa ctccagctgg    1740
attattttgg agcctgcaaa tctattccta cttgtacgga ctttgaagtg attcagtttc    1800
ctctacggat gagagactgg ctcaagaata tcctcatgca gctttatgaa gccaactctg    1860
aacacgctgg ttatctaaat gagaagcaga gaaataaagt caagaaaatt tacctggatg    1920
aaaagaggct tttggctggg gaccatccca ttgatcttct cttaagggac tttaagaaaa    1980
actaccacat gtatgtgtat cctgtgcact ggcagtttag tgaacttgac caacacccta    2040
tggatagagt cttgacacat tctgaacttg ctcctctgcg agcatctctg gtgcccatgg    2100
aacactgcat aacccgtttc tttgaggagt gtgaccccaa caaggataag cacatcaccc    2160
tgaaggagtg gggccactgc tttggaatta agaagagga catagatgaa aatctcttgt    2220
tttgaacgaa gattttaaag aactcaactt tccagcatcc tcctctgttc taaccacttc    2280
agaaatatat gcagctgtga tacttgtaga tttatattta gcaaaatgtt agcatgtatg    2340
acaagacaat gagagtaatt gcttgacaac aacctatgca ccaggtattt aacattaact    2400
ttggaaacaa aaatgtacaa ttaagtaaag tcaacatatg caaaatactg tacattgtga    2460
acagaagttt aattcatagt aatttcactc tctgcattga cttatgagat aattaatgat    2520
taaactatta atgataaaaa taatgcattt gtattgttca taatatcatg tgcacttcaa    2580
gaaaatggaa tgctactctt ttgtggtttta cgtgtattat tttcaatatc ttaatacoct    2640 aataaagagt ccataaaaat ccaaatgctt                                    2670
```

What is claimed is:

1. A method of treating a subject with a high risk for a high Gleason score prostate cancer, wherein the high Gleason score prostate cancer has a Gleason score of greater than 6, the method comprising the steps of:
   a. extracting one or more mRNAs from a urine sample from the subject;
   b. detecting the level of mRNA expression of PCA3, ERG and SPDEF;
   c. normalizing the level of mRNA expression of PCA3 and ERG to SPDEF;
   d. computing an EXO106 score using the formula:

$$\left( \log_2 \frac{\max(1, ERG \text{ copies})}{SPDEF \text{ copies}} + \log_2 \frac{\max(1, PCA3 \text{ copies})}{SPDEF \text{ copies}} + 16.92 \right) * 1.83,$$

wherein ERG copies is the level of mRNA expression of ERG, PCA3 copies is the level of mRNA expression of PCA3 and SPDEF copies is the level of SPDEF mRNA expression;
   e. comparing the EXO106 Score to a predetermined cutoff value; and
   f. treating the subject at a high risk for a high Gleason score prostate cancer when the EXO106 score is greater than the predetermined cutoff value.

2. The method of claim 1, wherein the urine sample is the first 40 mL voided from the bladder of the subject.

3. The method of claim 1, wherein the urine sample is the first 20 mL voided from the bladder of the subject.

4. The method of claim 1, wherein the predetermined cutoff value is 10.

5. The method of claim 1, wherein extracting one or more mRNAs in step (a) comprises:
   a. isolating a microvesicle fraction from the urine sample; and
   b. extracting one or more mRNAs from the microvesicle fraction.

6. The method of claim 5, wherein the step of isolating the microvesicle fraction comprises processing the sample to remove cells and cell debris and concentrating the microvesicle fraction by exposing the microvesicle fraction to ultrafiltration or a filtration concentrator, and washing the microvesicle fraction prior to extracting the one or more nucleic acids from the microvesicle fraction.

7. The method of claim 6, wherein the method further comprises adding an RNase inhibitor to the microvesicle fraction prior to extracting the one or more nucleic acids from the microvesicle fraction.

* * * * *